(12) United States Patent
Mather et al.

(10) Patent No.: US 8,404,484 B2
(45) Date of Patent: Mar. 26, 2013

(54) ACTIVE CELL CULTURE VIA SHAPE MEMORY

(75) Inventors: Patrick Mather, Manlius, NY (US); James Henderson, Syracuse, NY (US); Kelly Burke, Chelsea, MA (US); Kevin Davis, Chelsea, MA (US); Xiuling Xu, Albuquerque, NM (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 12/837,285

(22) Filed: Jul. 15, 2010

(65) Prior Publication Data

US 2011/0059527 A1   Mar. 10, 2011

Related U.S. Application Data

(60) Provisional application No. 61/225,700, filed on Jul. 15, 2009.

(51) Int. Cl.
*C12N 5/02* (2006.01)
(52) U.S. Cl. .......... 435/395; 435/397; 435/402
(58) Field of Classification Search .......... 435/395, 435/397, 402
See application file for complete search history.

(56) References Cited

U.S. PATENT DOCUMENTS

| 6,160,084 | A | 12/2000 | Langer et al. |
| 6,592,995 | B2 | 7/2003 | Topolkaraev et al. |
| 6,720,402 | B2 | 4/2004 | Langer et al. |
| 6,858,680 | B2 | 2/2005 | Gunatillake et al. |
| 2004/0110285 | A1* | 6/2004 | Lendlein et al. ........ 435/366 |
| 2005/0245719 | A1* | 11/2005 | Mather et al. .......... 528/60 |

FOREIGN PATENT DOCUMENTS

WO   WO 2008130650 A1 * 10/2008

OTHER PUBLICATIONS

Taniguchi et al.; Functional modification of biodegradable polyesters through a chemoselective approach: application to biomaterial surfaces; Polymer International; vol. 55; pp. 1385-1397; published online Oct. 20, 2006.*
Knight, P. T., K. M. Lee, H. Qin and P. T. Mather (2008). "Biodegradable thermoplastic polyurethanes incorporating polyhedral oligosilsesquioxane." Biomacromolecules 9(9): 2458-2467.

* cited by examiner

*Primary Examiner* — Michele K Joike
*Assistant Examiner* — Antonio Galisteo Gonzalez
(74) *Attorney, Agent, or Firm* — David L. Nocilly; Bond Schoeneck & King

(57) ABSTRACT

Substrates for cell culture and tissue engineering bioreactors consisting of polymers that change their shape over time under stimulation by temperature change, hydration, degradation, or other means. A method of controlling cell culture using a biodegradable shape memory polymer, wherein shape changes can transfer stresses, strains, or both to adherent or otherwise connected cells such that the mechanical stimulus impacts cell development and the resulting properties of tissues.

13 Claims, 40 Drawing Sheets

(a)

(b)

24 h  48 h  72 h 24 h 48 h 72 h

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: commercially available peptide fragment

<400> SEQUENCE: 1

Gly Arg Gly Asp Ser
1               5

ACTIVE CELL CULTURE VIA SHAPE MEMORY

CROSS-REFERENCE TO RELATED APPLICATIONS

The present application claims the priority of U.S. Provisional Application No. 61/225,700 entitled "Active Cell Culture Via Shape Memory" filed Jul. 15, 2009, the entire contents of which are incorporated herein by reference.

BACKGROUND OF THE INVENTION

1. Field of the Invention

The present invention relates to cell cultures and, more specifically, shape-memory polymers for use in cell culture.

2. Description of the Related Art

Living cells are remarkably complex, dynamic, and versatile systems, but the material substrates currently used to culture them are not. Although properties of the material substrate, such as surface geometry and stiffness, can direct cell lineage specification, cell-growth kinetics, cell orientation, cell migration, and cell traction, the polymeric materials commonly used in cell culture and tissue engineering only offer attached cells surfaces and structures of unchanging properties. This physical stasis of current cell culture and tissue engineering materials severely limits our ability to control cell-material interactions during cell culture and tissue engineering and, therefore, our ability to advance understanding and application of fundamental cell processes.

During tissue formation and repair, the extracellular matrix (ECM) undergoes continual biochemical turnover with corresponding architectural changes that affect structural and mechanical properties. Through cell-matrix interactions, this dynamic ECM behavior supports and regulates morphogenesis. Recent in vitro studies have begun to elucidate the principles through which this support and regulation occurs. Notably, both ECM-dependent changes of cell shape and ECM mechanical stiffness can regulate progenitor cell differentiation. As the fundamental understanding of these principles improves, there is the potential to use biomimetic scaffolds to apply these principles in regenerative medicine strategies. But the development of new scaffolds that incorporate these principles and mimic the dynamic behavior of natural ECMs has lagged behind advances in the understanding of the principles themselves. On the one hand, polymer scaffolds of controlled pore architecture provide tailored mechanical function and mass transport properties within complex 3D anatomical shapes but are fundamentally static structures. On the other hand, hydro gels can be programmed to undergo changes in structure, such as gelation following injection or controlled swelling, but sacrifice many of the benefits of a controlled architecture. Therefore, there is a need to develop advanced biomimetic scaffolds that combine the benefits of a controlled pore architecture with the ability to undergo programmed changes in architecture.

Regenerative medicine has the potential to develop therapies for previously untreatable diseases and conditions while providing technology recognized as critical to combating rising healthcare costs. The processes of tissue formation during embryogenesis and tissue repair following injury provide the blueprints for regenerative medicine. During tissue formation and repair, the architecture of the natural extracellular matrix and dynamic changes in that architecture are central to many key morphogenetic processes. Matrix architecture has profound effects on the shape of cells in the matrix, and recent studies elegantly demonstrate that cell shape regulates cell differentiation. Yet, scaffolds, the matrices of tissue engineering, currently have little or no ability to undergo programmed changes in architecture. Therefore, there is a critical need to develop advanced biomimetic scaffolds with the ability to undergo programmed changes in architecture.

Shape-memory polymers ("SMPs") are a class of smart materials that offer mechanical action triggered by an external stimulus such as temperature change, as shown in FIG. 1, which may be useful as cell culture scaffolds. More specifically, SMPs are able to 'remember' one or more shapes, each determined by network elasticity, but can be stored in temporary shapes by virtue of material immobilization, commonly by vitrification or crystallization. As a simple example, a complex three-dimensional SMP shape can be compacted into a slender form (suitable for catheter delivery to the body, or to fit into an otherwise compact space) by a cycle of heating, deforming, cooling, and unloading. 'Good' SMPs will be those that feature elasticity during deformation and solidification (strain "fixing") during cooling. In those cases, application of heat, light, or solvent exposure can trigger near-complete return to the equilibrium, complex shape through network chain mobilization.

Several review articles have been written on SMPs and these indicate a diversity of synthetic approaches and applications areas, the latter ranging from mechanical mechanisms to deployable space devices to surgical implements. Despite an accelerated publication frequency on SMPs exceeding 300/yr, particularly for medical applications, there are so far no reports on the utilization of SMPs in cell culture or tissue engineering.

On the other hand, numerous accounts of biodegradable SMPs have appeared that are exploited in the current application. These are: (i) polyurethanes with biodegradable soft and hard blocks; and (ii) photocured, end-linked networks with biodegradable network chains. For case (i), shape memory is possible through the elasticity of physical cross linking and strain fixing by vitrification of the soft segments. For case (ii), shape memory is possible through covalent network junctions that yield elasticity and the crystallizable network chains that can temporarily fix strains. Biodegradability and shape memory are necessary, but not sufficient, characteristics. In addition, processing into a proper form and control over cell-surface interactions are needed.

One category of materials with excellent shape-memory properties are hydro gels. Hydro gels from both natural and synthetic polymers are excellent biomaterial scaffolds for repairing and regenerating a variety of tissues and organs, such as bone, cartilage, skin, vasculature and nerves. They are attractive because: (i) they can provide a three-dimensional (3D) environment similar to the extracellular matrix (ECM), which allows diffusion of oxygen, nutrients and metabolic waste through the elastic network; and (ii) the cross-linked polymer networks are capable of absorbing water to swell, but are insoluble, to make these materials "soft" and "wet", which improve their compatibility with biological tissues. A hydrogel will exhibit shape memory functionality if it can be stabilized in the deformed state in a temperature range that is relevant for the particular application. A typical shape memory hydrogel is a cross-linked material having a hydrophilic fraction that will swell in water and hydrophobic sections with reversible order-disorder structures controlled by temperature. While cross linking sets the permanent shape (high temperature), the ordered structure that forms at a temperature, $T < T_{trans}$ (switching transition temperature) can be used to fix secondary shapes established by deformations at a higher temperature, $T>T_{trans}$. Heating above $T_{trans}$ triggers complete shape recovery.

Beside shape memory properties, hydro gels employed as implantable biomedical devices should also have good biocompatibility and bioactivity to facilitate cell-polymer interactions and avoid adverse physiological reactions between plants and surrounding host tissues. However, most synthetic hydro gels typically exhibit minimal or no intrinsic biological activity, which may not provide an ideal environment for culturing anchorage-dependent cells, such as endothelial cells (ECs), smooth muscle cells (SMCs), fibroblast and osteoblasts. These drawbacks prevent them from being used directly for tissue repair. Consequently, much work has been done both physically and chemically to incorporate bioactive factors and peptides into these scaffolds in order to provide them with signaling domains that have specific interactions with surrounding cells by molecular recognition. Among these functional biosignal molecules, Arg-Gly-Asp (RGD) peptide sequences derived from ECM proteins are the most widely studied cell-binding domains for the bioactive modification of scaffolds. Cells adhere to the hydro gels modified with RGD peptide sequences via particular interactions between the grafted adhesion ligands and the integrin receptors on the cell membrane.

To maintain the biological activity of the peptide upon modification, the bioactive ligand must be flexible and experience minimal steric hindrance. It has been shown that RGD sequences covalently immobilized to a hydrogel scaffold via poly(ethylene glycol) ("PEG") spacer arms can promote cell adhesion and spreading compared with those without the PEG arms. It is hypothesized that flexible PEG arms permit biospecific receptor-ligand interactions between the peptide and cells that leads to cells behaving in response to the RGD sequences incorporated in the scaffold, while cell adhesion on the scaffold without a PEG spacer is principally nonspecific due to the sterical unavailability of the peptide incorporated in the scaffold. In addition, peptide incorporated without a PEG spacer causes more undesired protein adsorption than an equivalent amount of peptide incorporated via a PEG spacer.

Despite many recent advancements in hydrogel shape memory, there is a continued need for a biodegradable and biocompatible hydrogel based scaffold with tailored shape memory effect and good bioactivity as well as desirable mechanical property for soft-tissue applications.

BRIEF SUMMARY OF THE INVENTION

It is therefore a principal object and advantage of the present invention to provide shape memory polymers useful for cell culture.

It is another principal object and advantage of the present invention to provide a method of cell culture using a biodegradable shape memory polymer.

It is a further object and advantage of the present invention to provide cell culture scaffolds composed of a biodegradable shape memory polymer.

In accordance with the foregoing objects and advantages, the present invention provides a cell culture scaffold comprising a biodegradable thermoplastic shape memory polymer with a first configuration. The shape memory polymer comprises: (i) a hard segment, made of polyhedral oligosilsesquioxane; and (ii) a soft segment made of poly(D,L-lactide), polyethylene glycol, hexane diol, epsilon-caprolactone, a polyol (including but not limited to poyl(epsilon-caprolactone), a diisocyanate, or a combination thereof. Upon application of a stimulus, the shape memory polymer assumes a second configuration.

According to a second aspect of the present invention is provided a cell culture scaffold comprising a biodegradable thermoplastic shape memory polymer with a first configuration. The shape memory polymer comprises: (i) an end-linked poly($\in$-caprolactone)/poly(ethylene oxide) ("PCL/PEO") copolymer; and (ii) a peptide. Upon application of a stimulus, the shape memory polymer assumes a second configuration. The peptide is preferably comprised of at least the sequence Arginine-Glycine-Aspartic acid ("RGD"), although it can be any sequence that promotes adhesion of cells to the scaffold.

According to a third aspect of the present invention is provided a cell culture scaffold comprising a biodegradable thermoplastic shape memory polymer with a first configuration. The shape memory polymer comprises a poly($\in$-caprolactone)/polyethylene glycol/peptide network. Upon application of a stimulus, the shape memory polymer assumes a second configuration. The poly($\in$-caprolactone) preferably has an average molecular weight of 3,000 g/mol, and the polyethylene glycol preferably has an average molecular weight of 2,000 g/mol, although the average molecular weight of either can vary depending on the desired characteristics of the polymer. The peptide is preferably comprised of at least the sequence Arginine-Glycine-Aspartic acid ("RGD"), although it can be any sequence that promotes adhesion of cells to the scaffold. Further, the shape memory polymer preferably possesses a transition temperature between 30° C. and 45° C., and the poly($\in$-caprolactone) typically comprises from about 60 to 85 weight percent of said polymer. Also provided is a method of preparing the above shape memory polymer via the steps of: (i) polymerizing the poly($\in$-caprolactone) into a macromer; (ii) conjugating the peptide to a polyethylene glycol monoacrylate to produce an acrylate-polyethylene glycol-peptide; and (iii) cross linking the poly($\in$-caprolactone) macromer with the acrylate-polyethylene glycol-peptide using a crosslinker, wherein the crosslinker can be a tetrathiol.

According to a fifth aspect of the present invention is provided a method of cell culture using one of the above shape memory polymers. According to one embodiment, the method comprises the steps of: (i) forming a cell culture scaffold using one of the polymers described herein; (ii) seeding the cell culture scaffold with a cell; (iii) promoting the proliferation or growth of the cell; and (iv) applying a stimulus through a confirmation change of the shape memory polymer.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 17A:
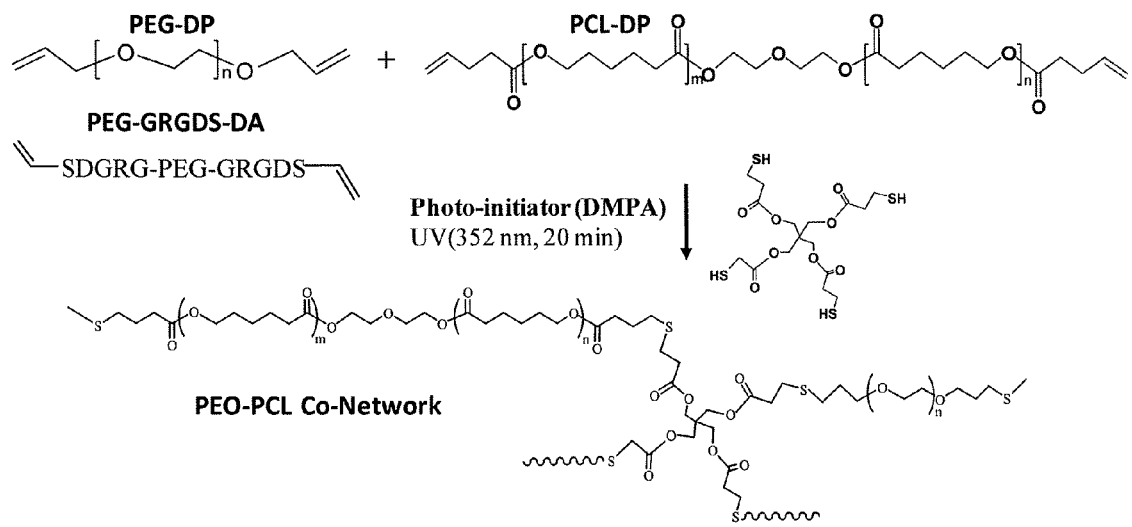
Figure 18:
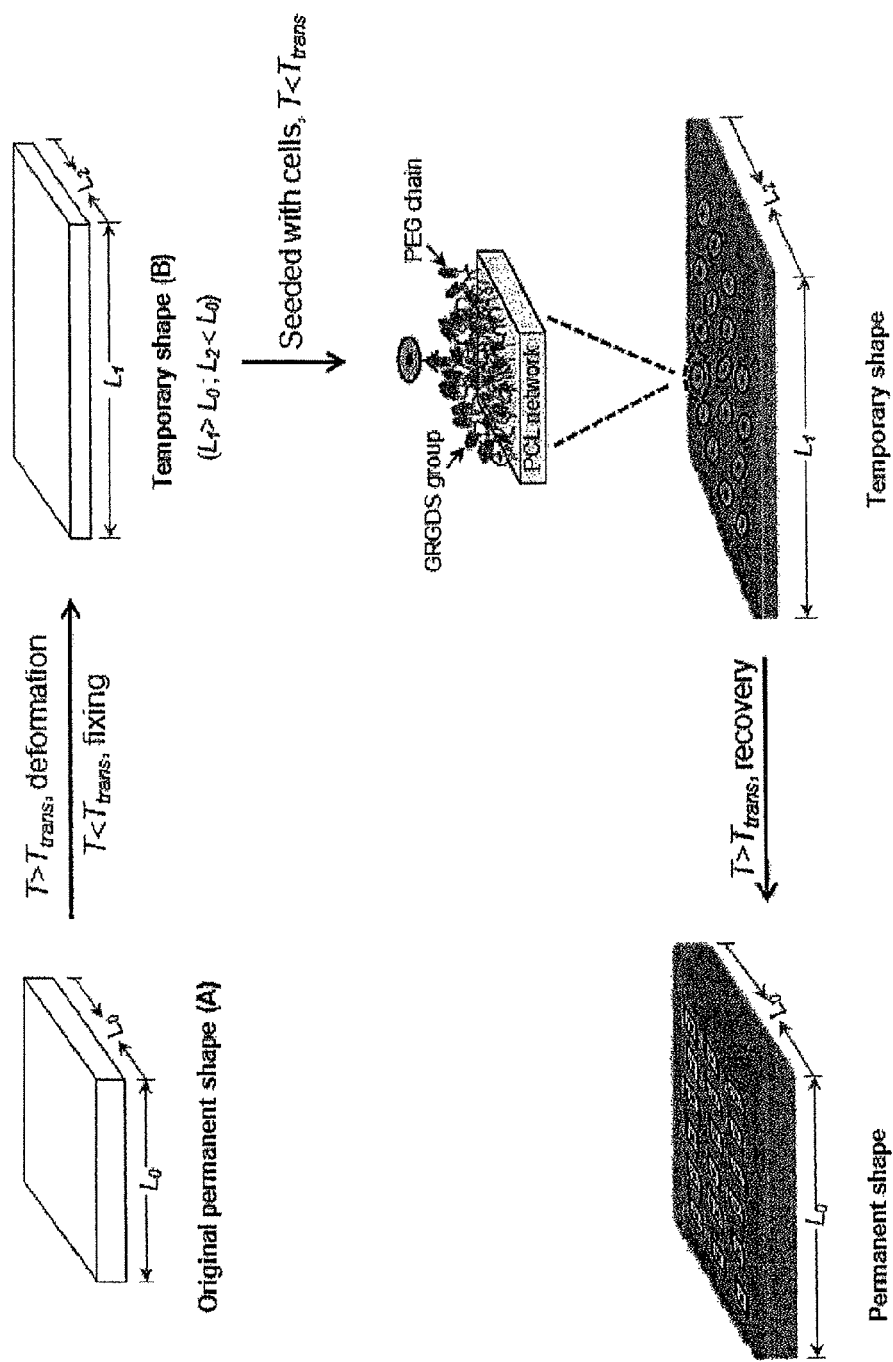
Figure 19A:
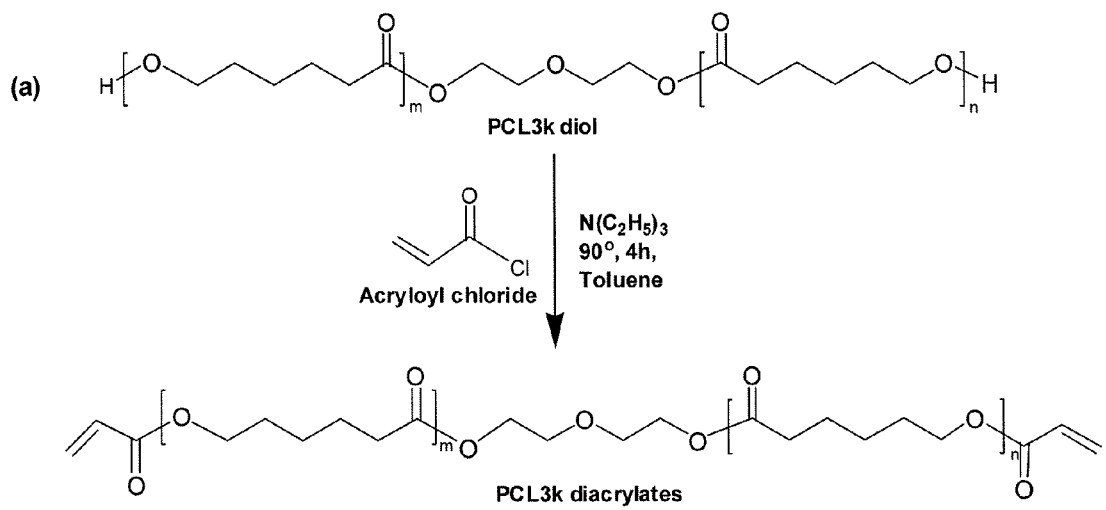
Figure 19B:
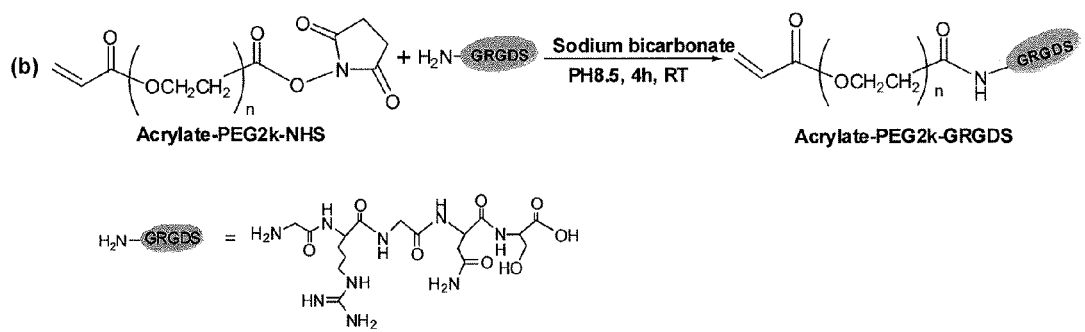
Figure 20:
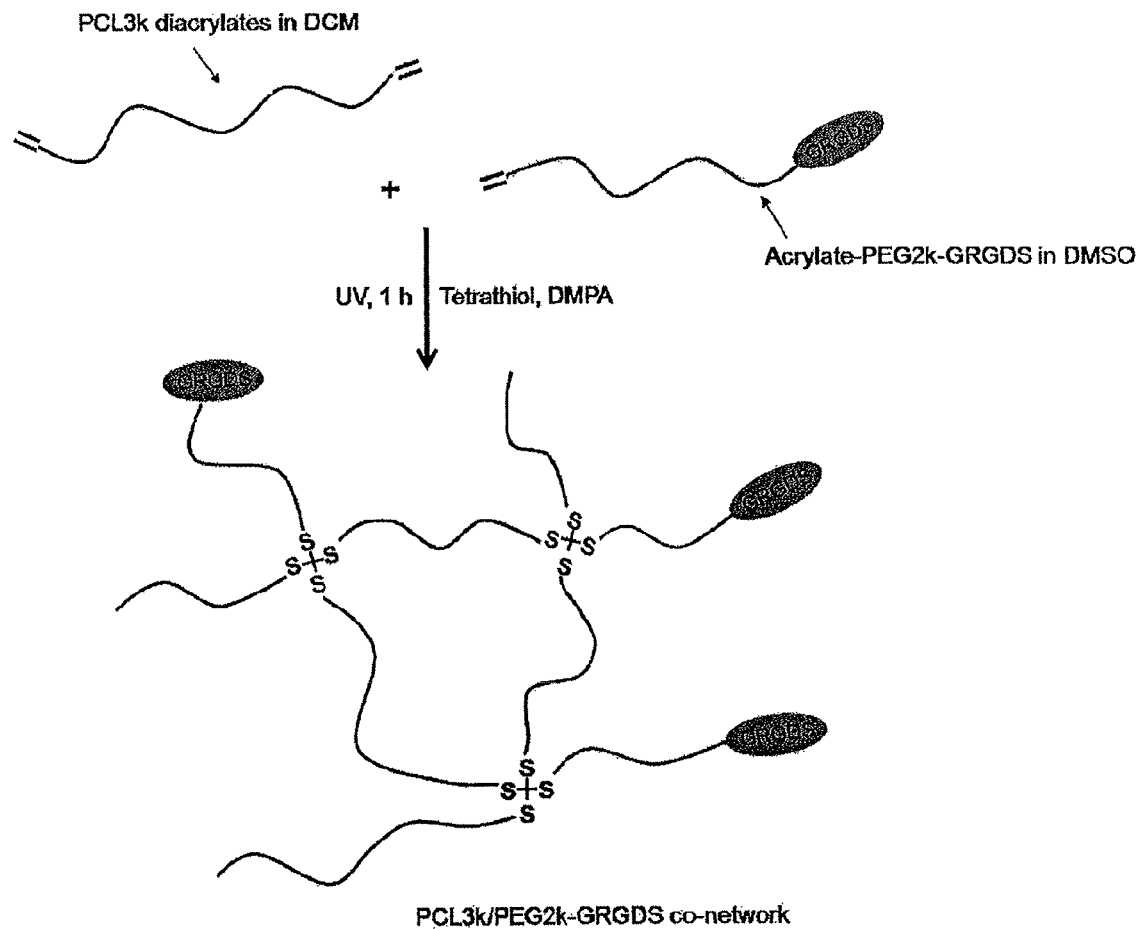
Figure 20:
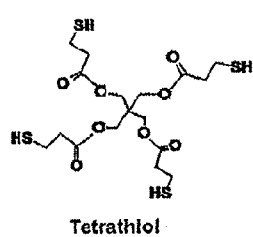
Figure 20:
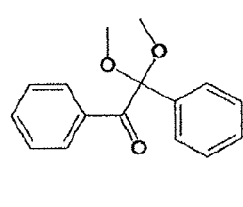
Figure 21:
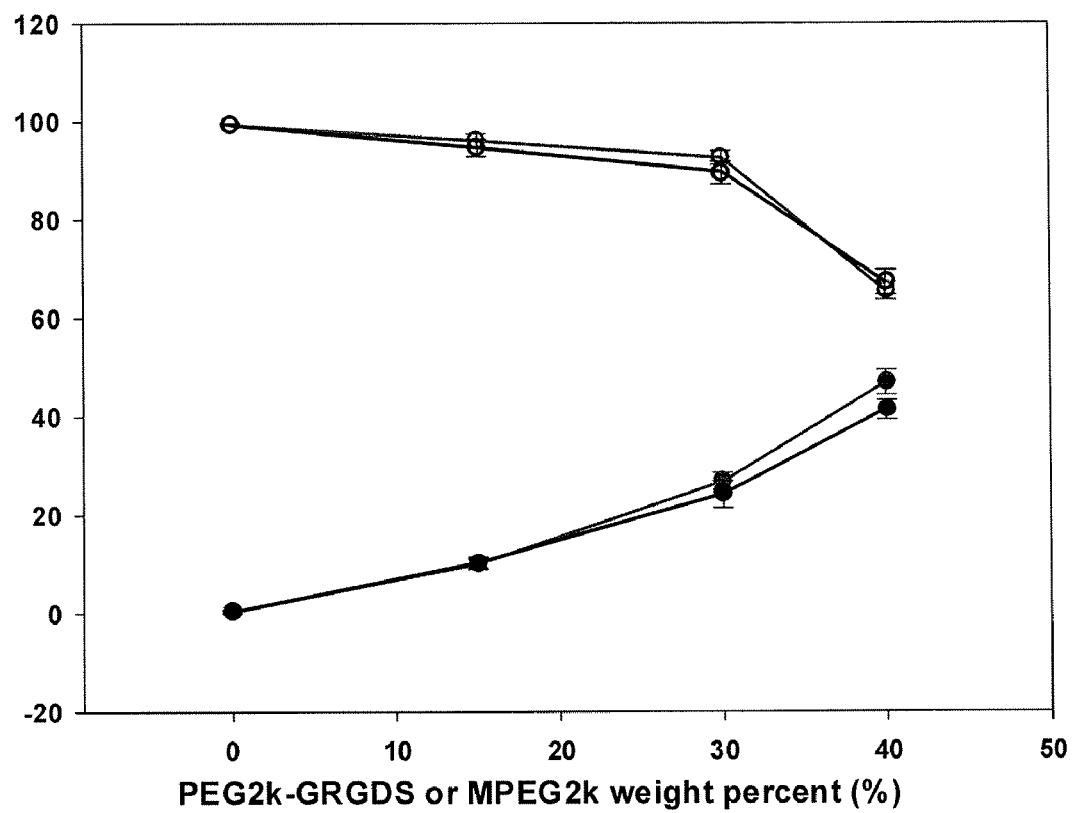
Figure 22:
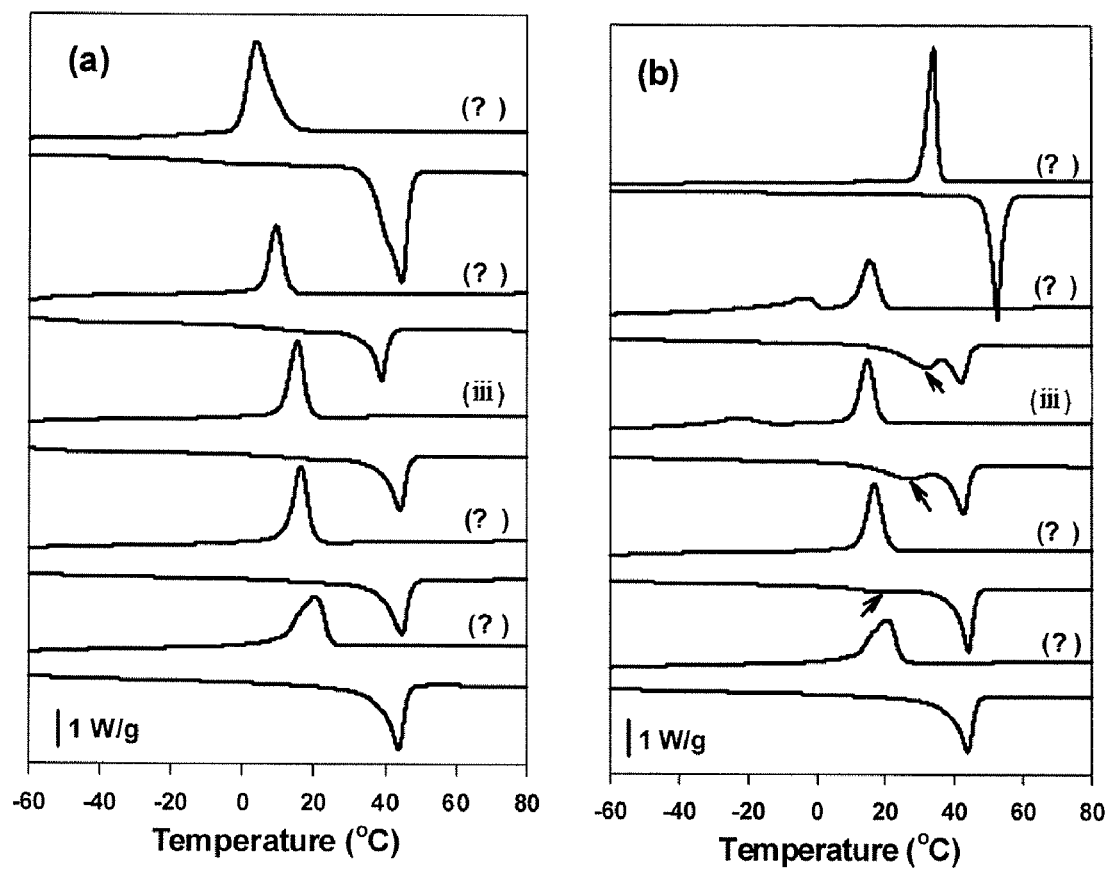
Figure 23:
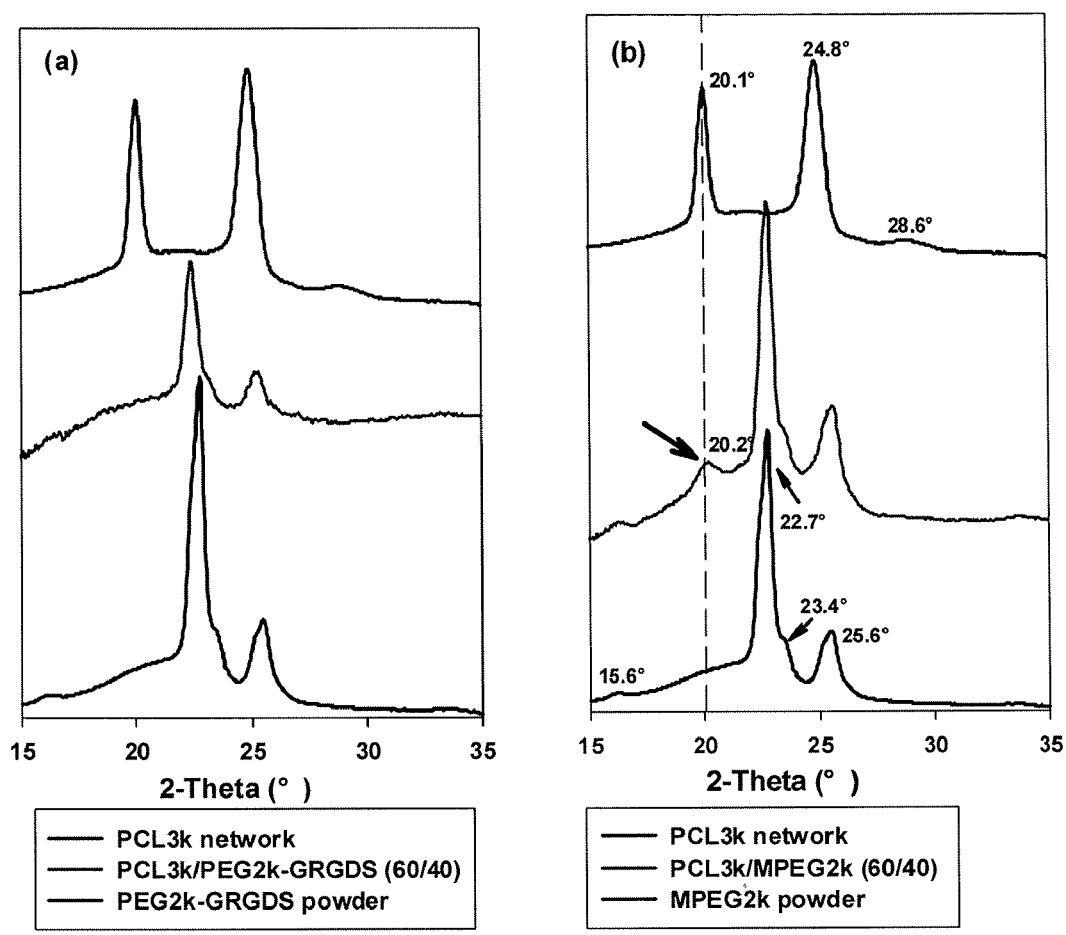
Figure 24:
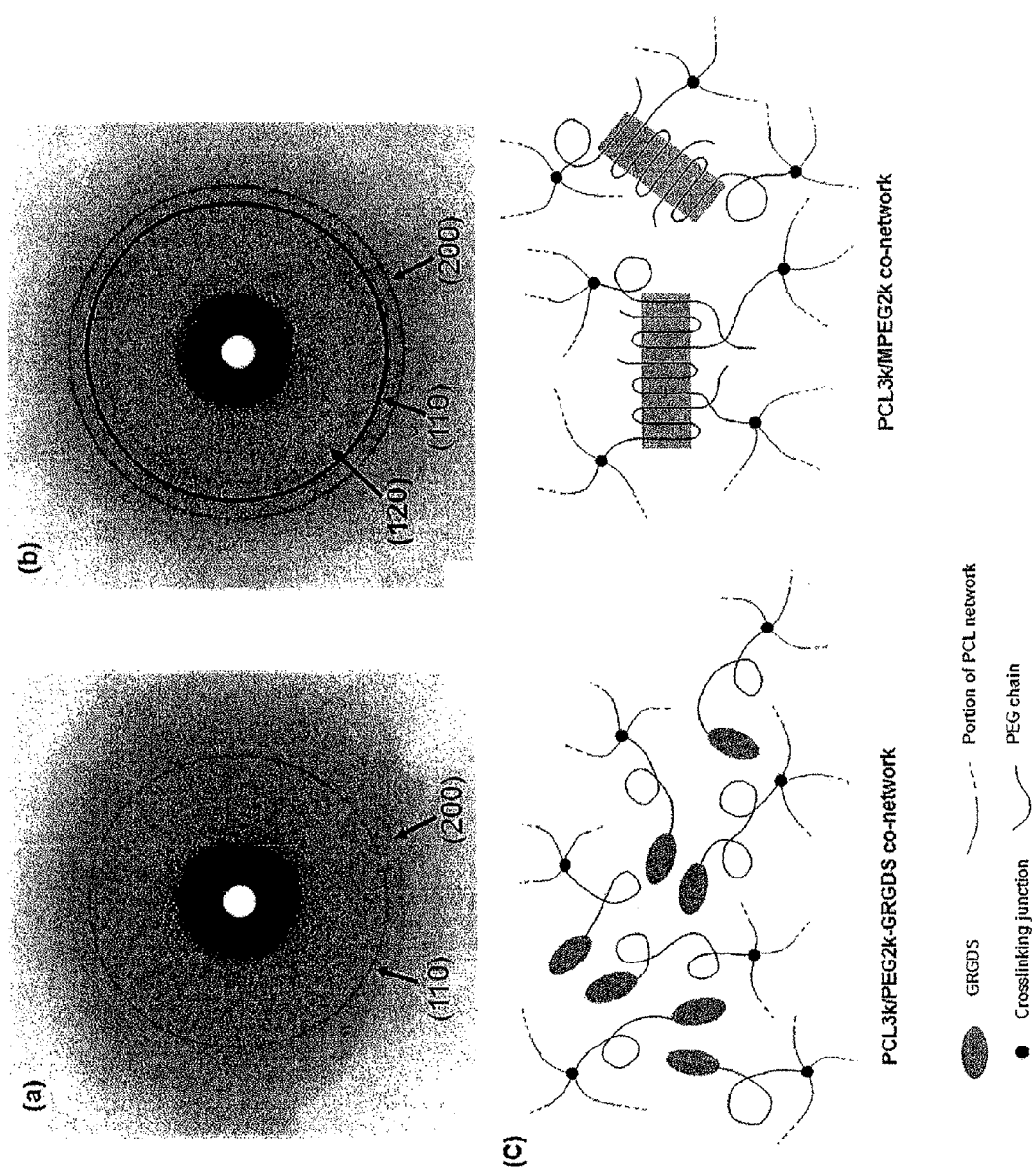
Figure 25:
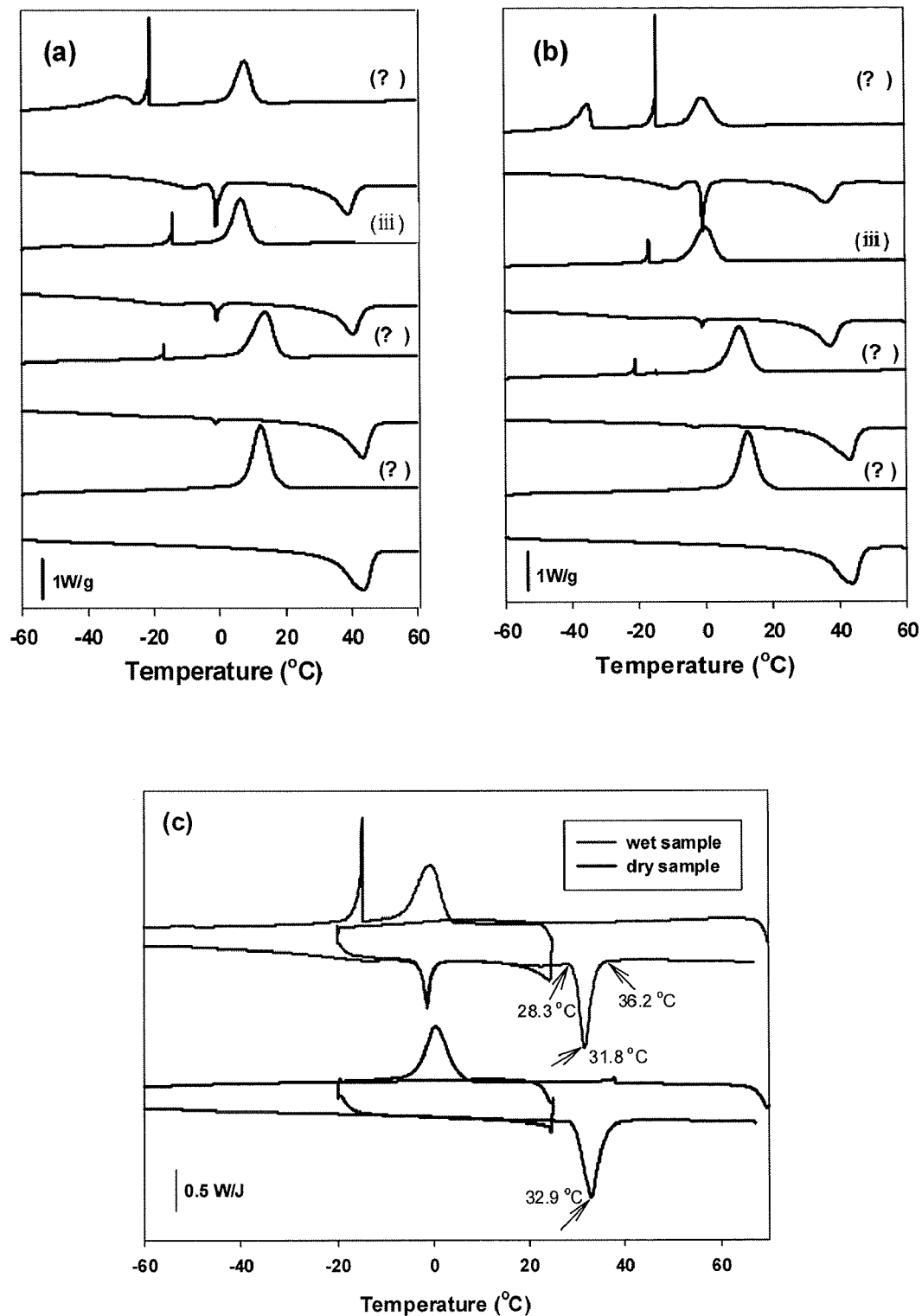
Figure 26A:
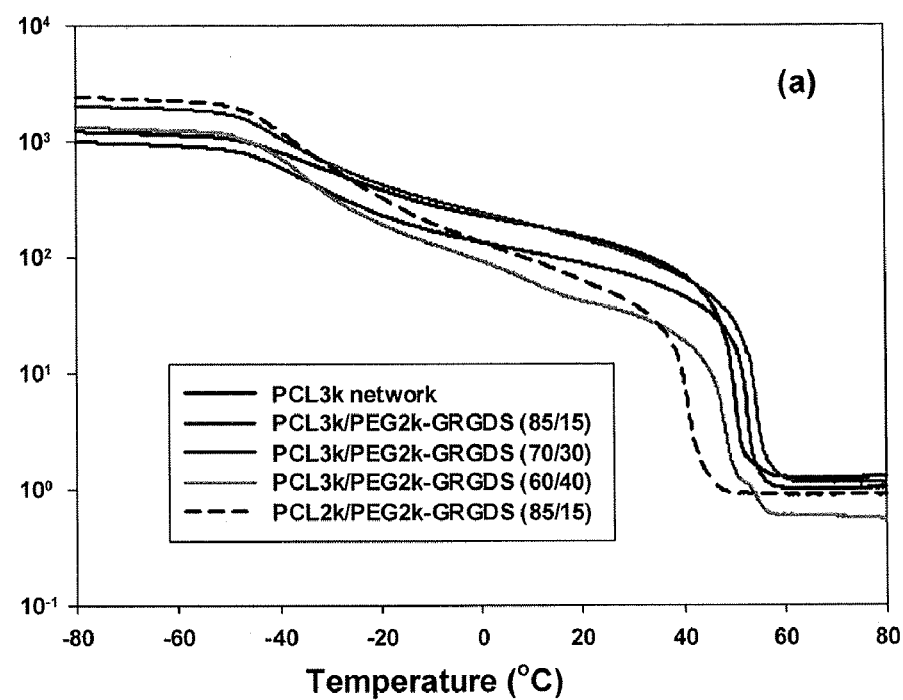
Figure 26B:
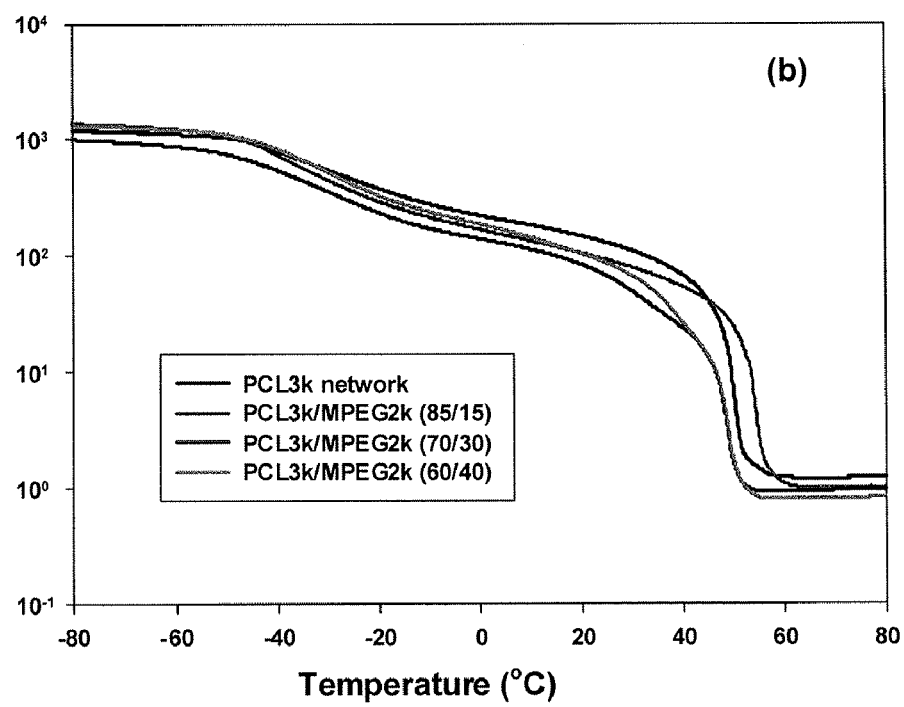
Figure 26C:
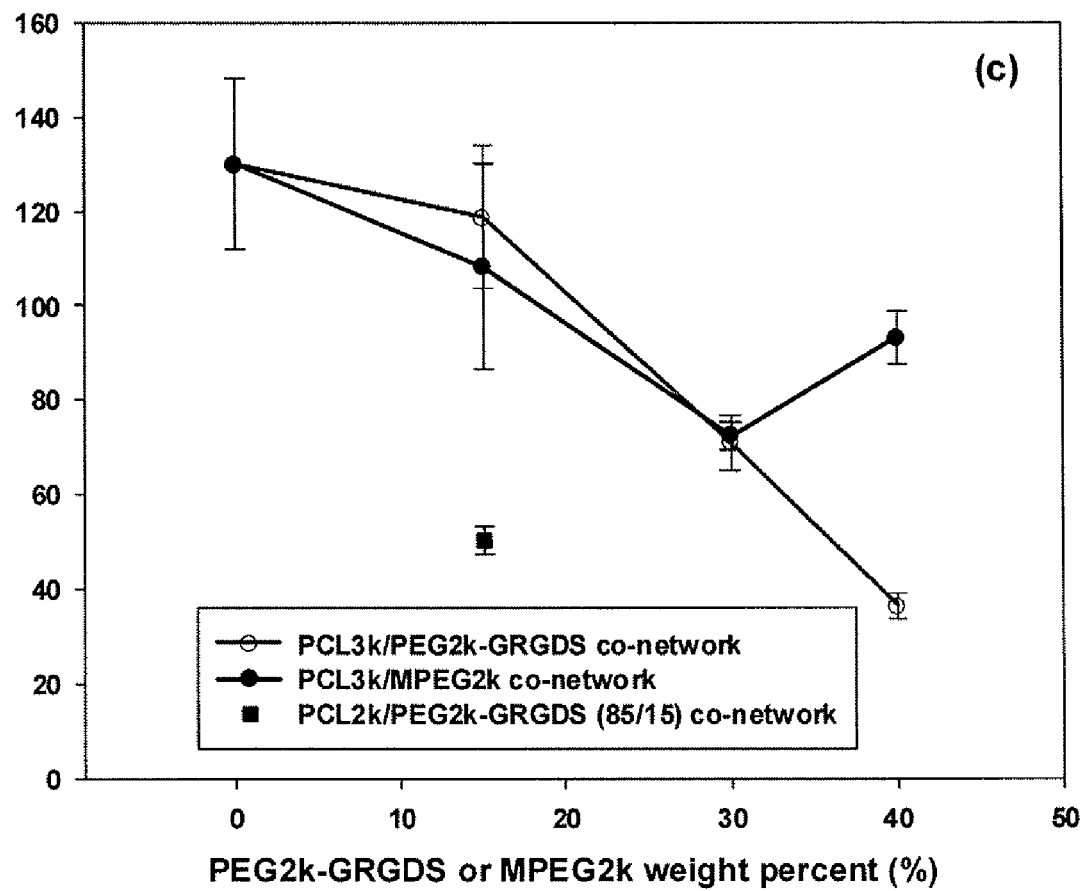
Figure 27A:
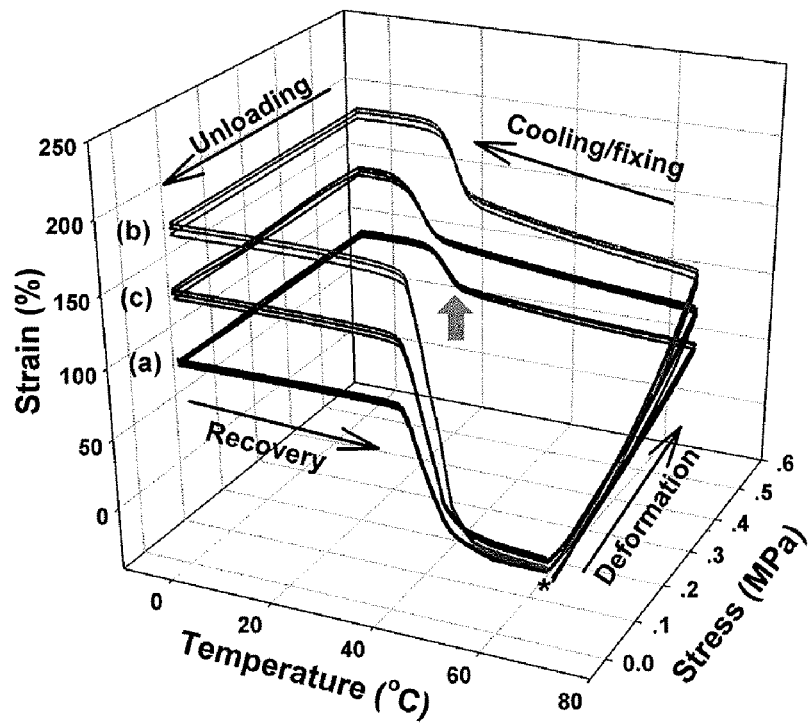
Figure 27B:
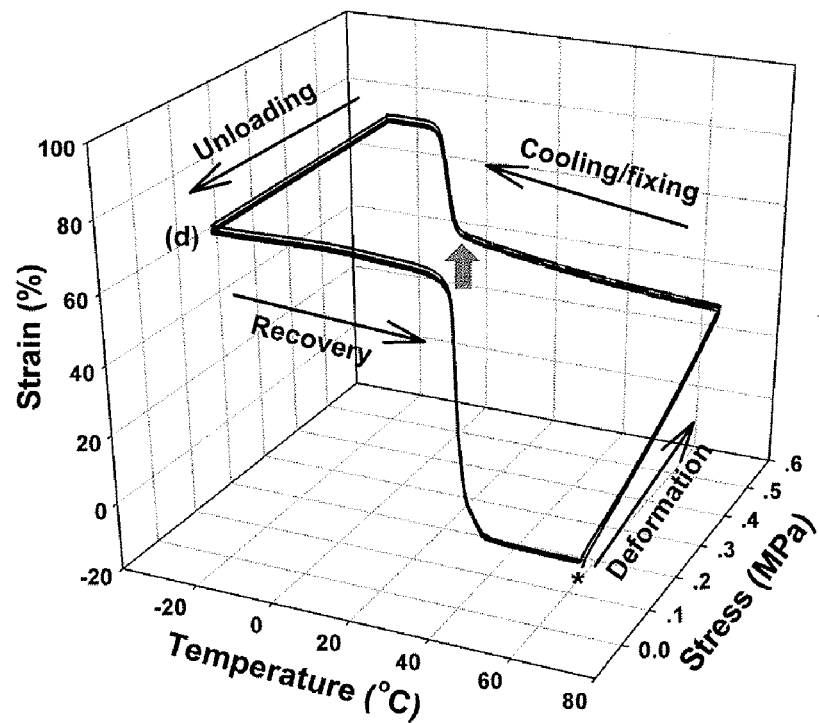
Figure 28A:
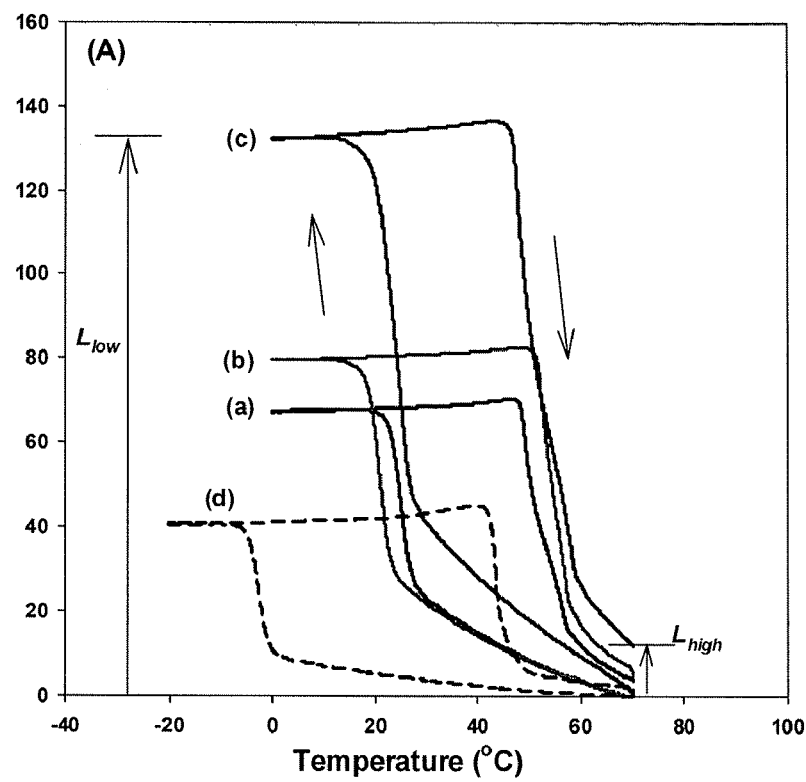
Figure 28B:
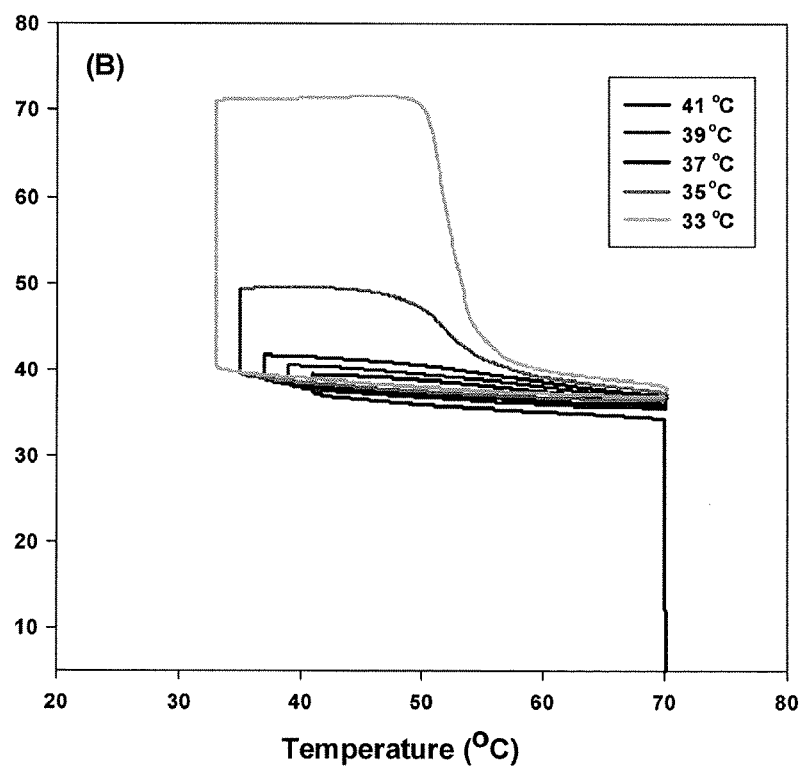
Figure 28C:
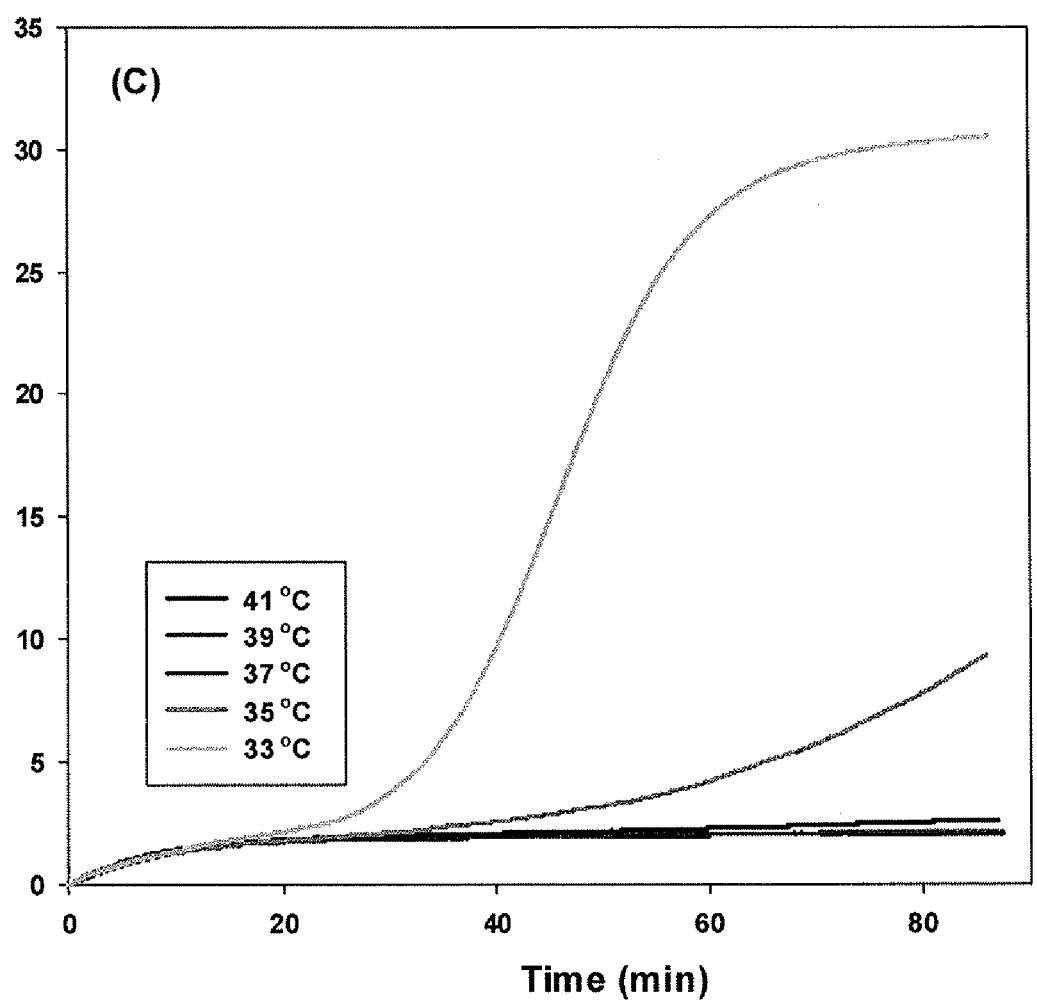
Figure 29:
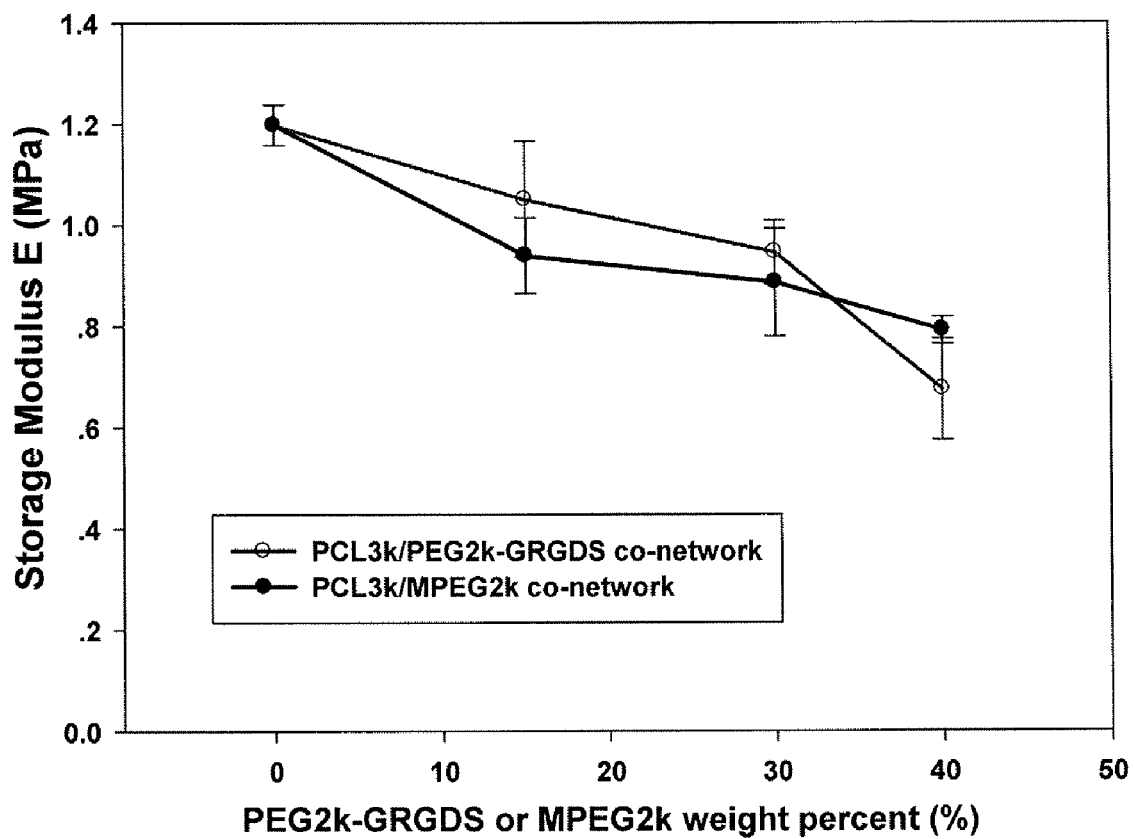
Figure 30A:
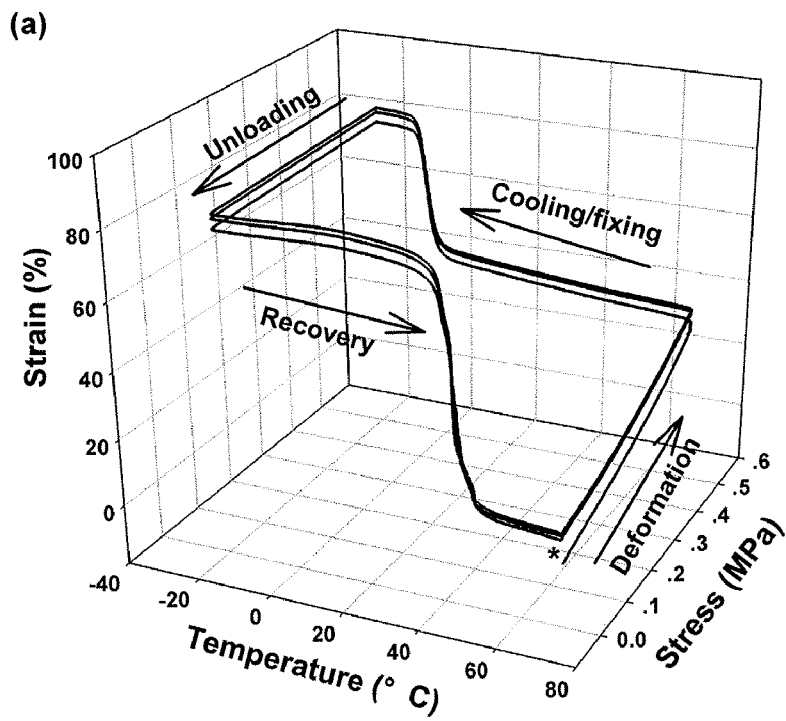
Figure 30B:
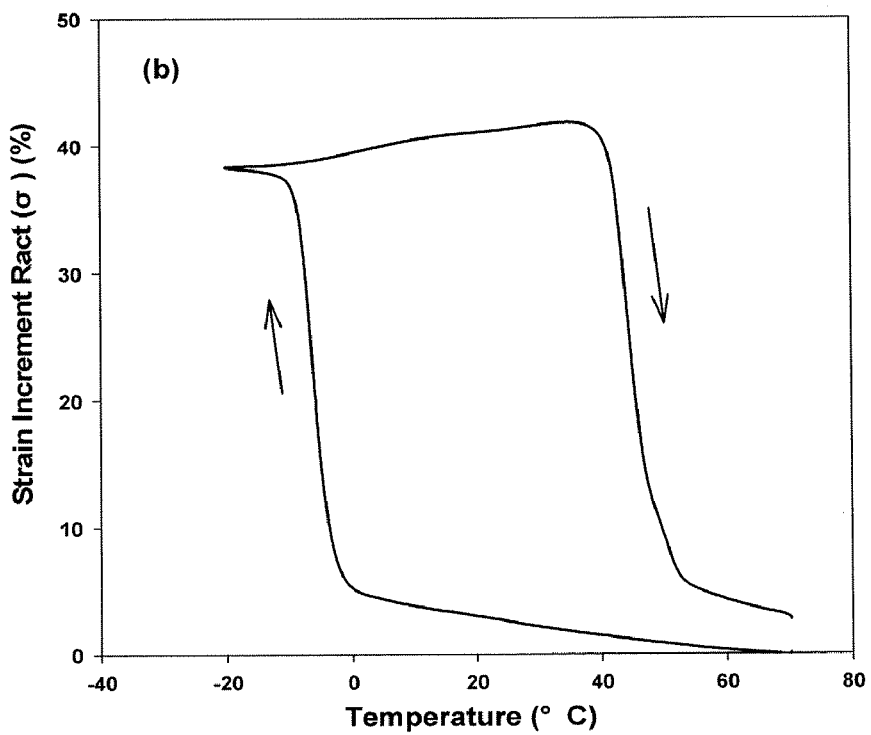
Figure 31A:
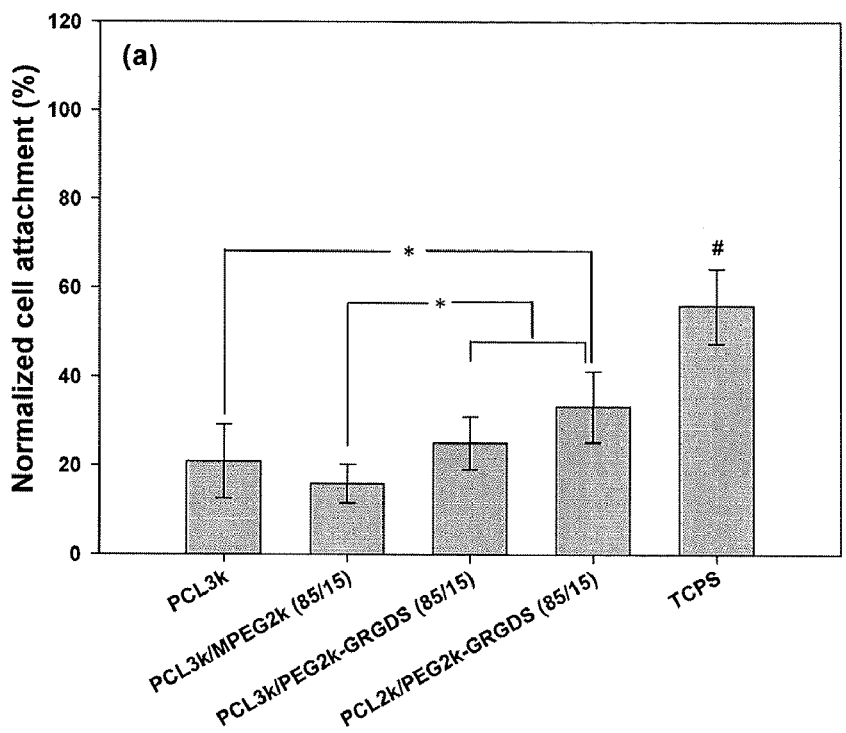
Figure 31B:
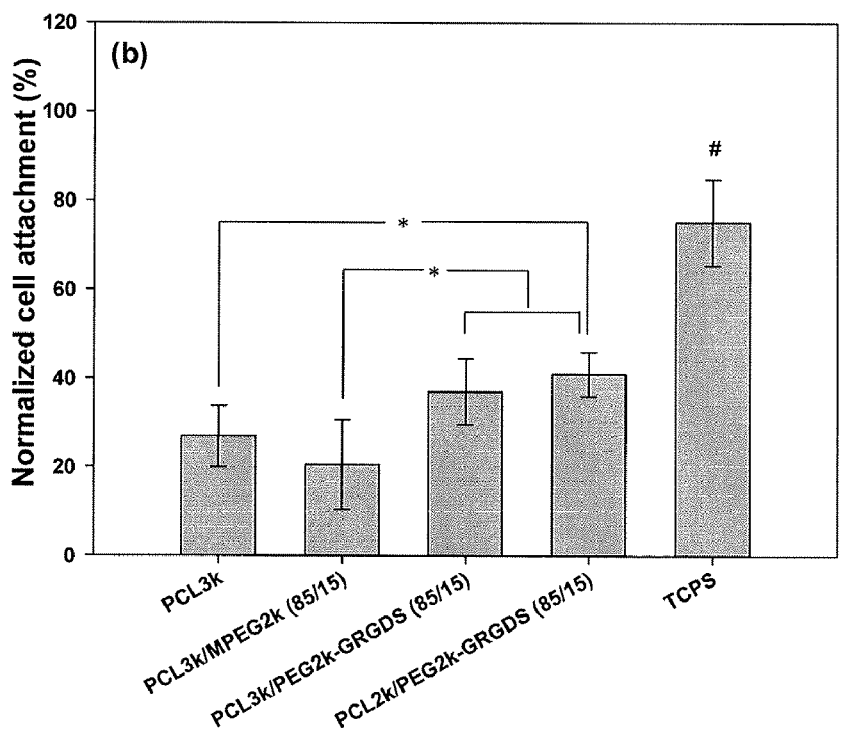
Figure 31C:
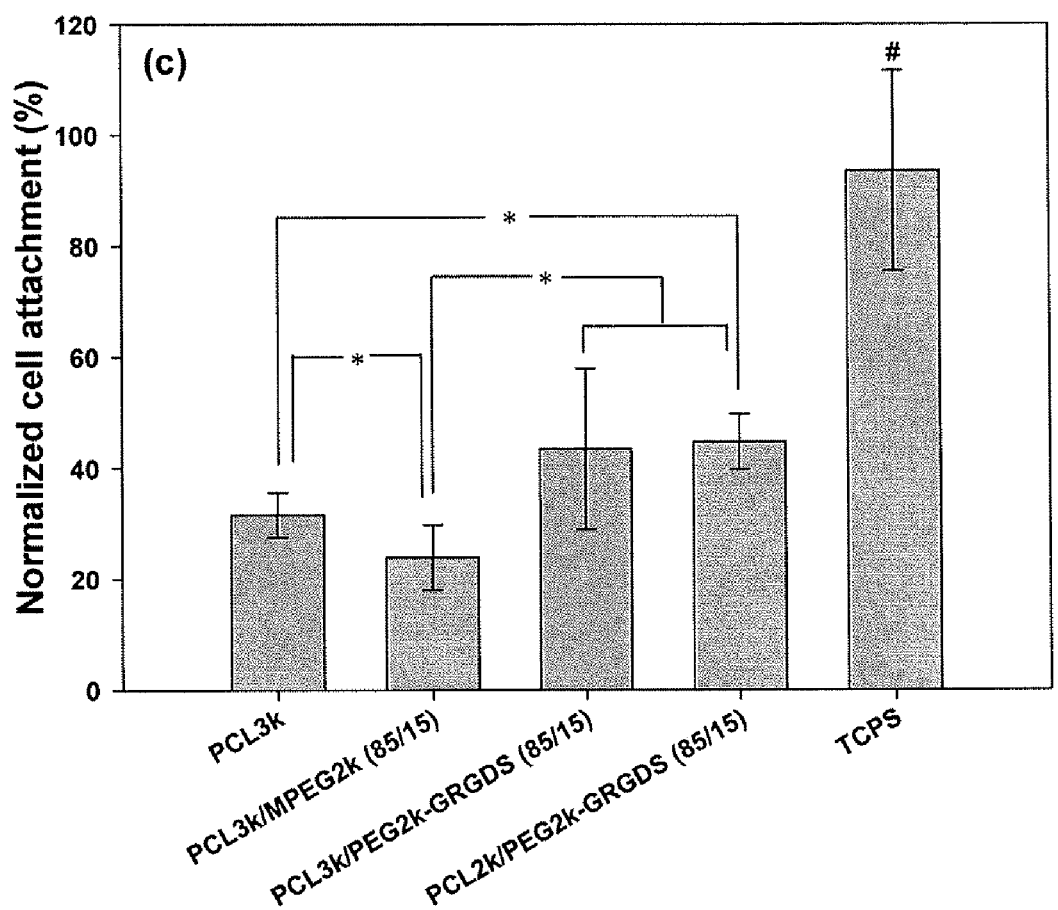
Figure 32A:
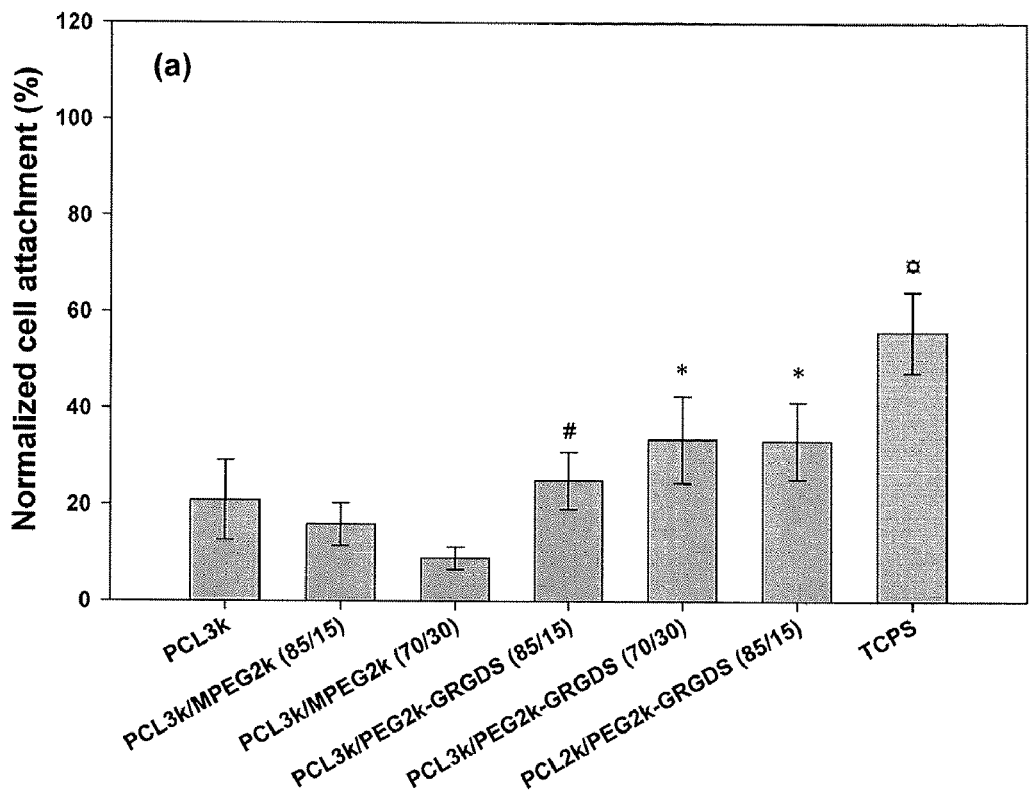
Figure 32B:
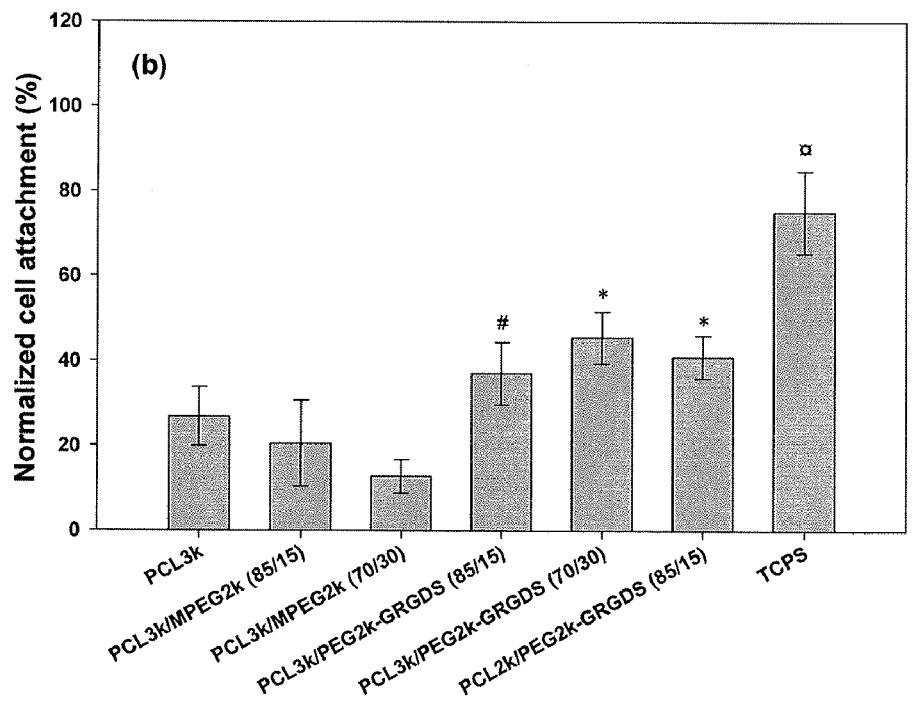
Figure 32C:
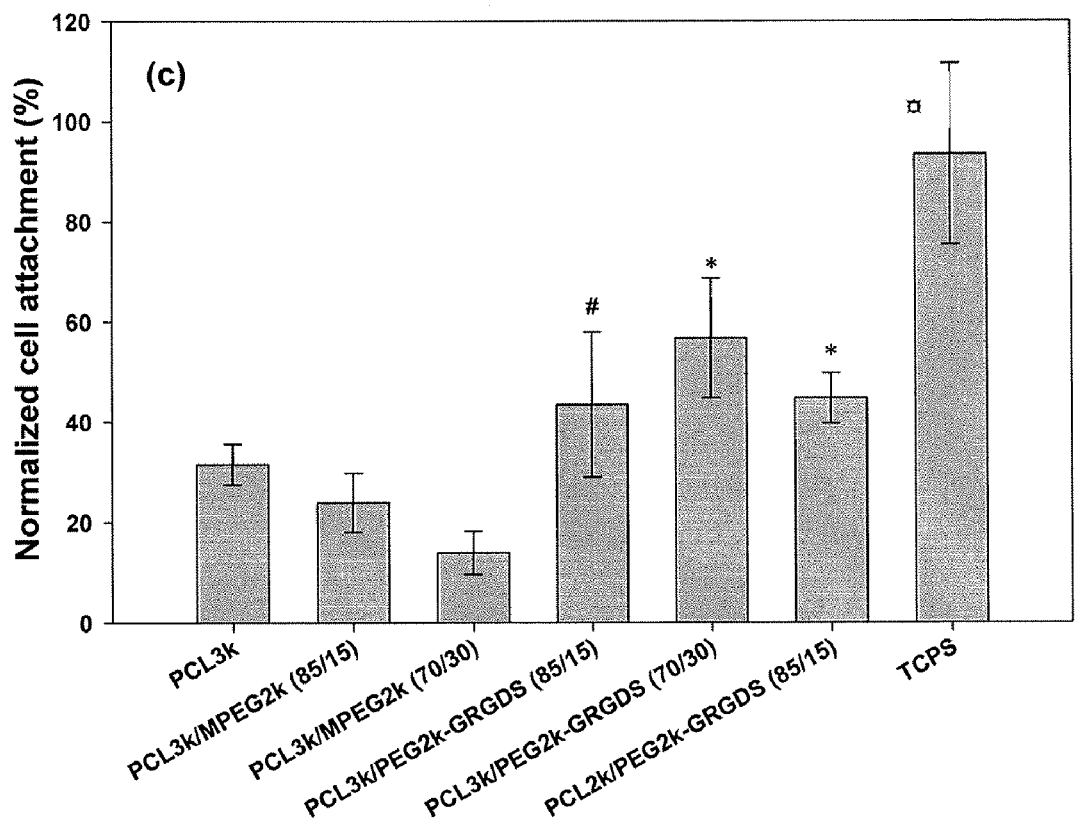
Figure 33:
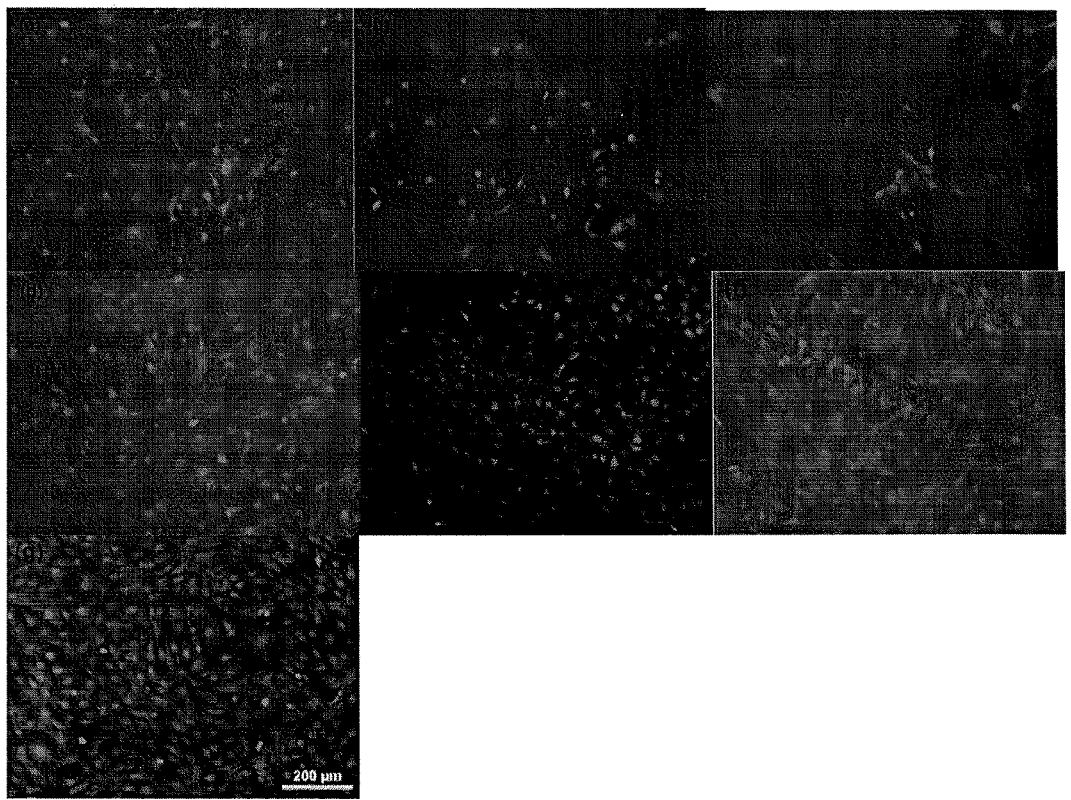
Figure 34A:
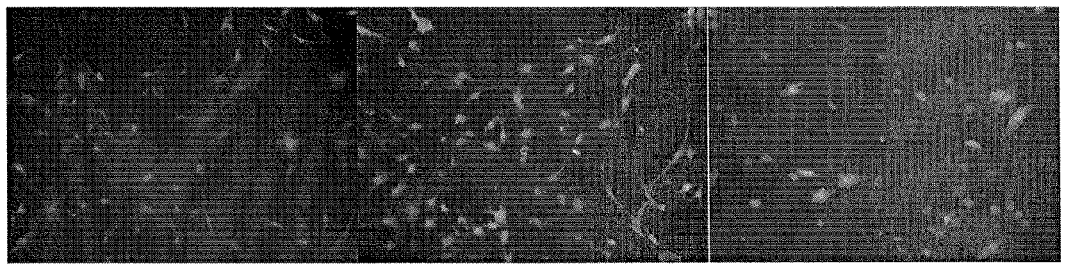
Figure 34B:
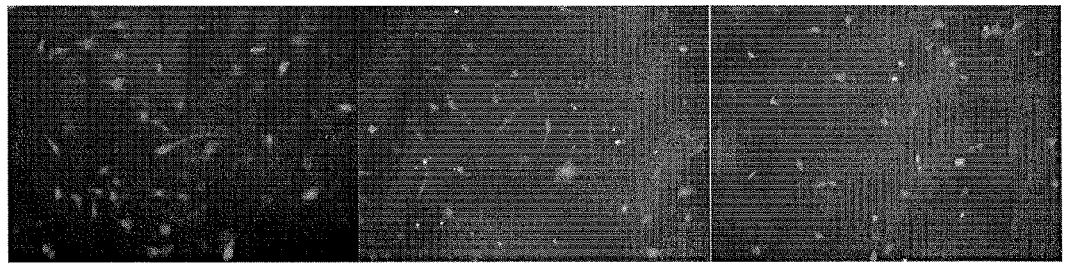
Figure 34C:
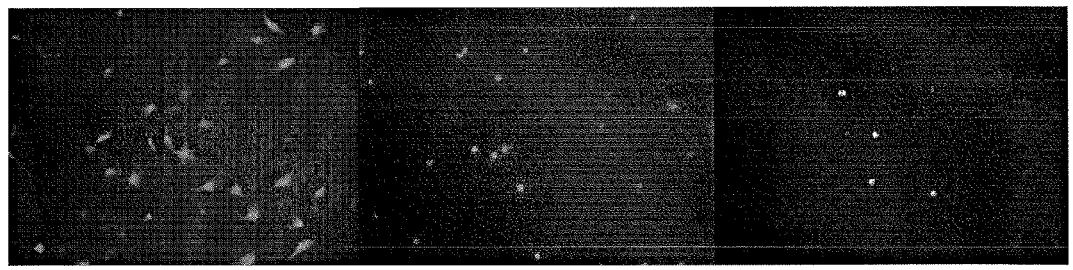
Figure 34D:
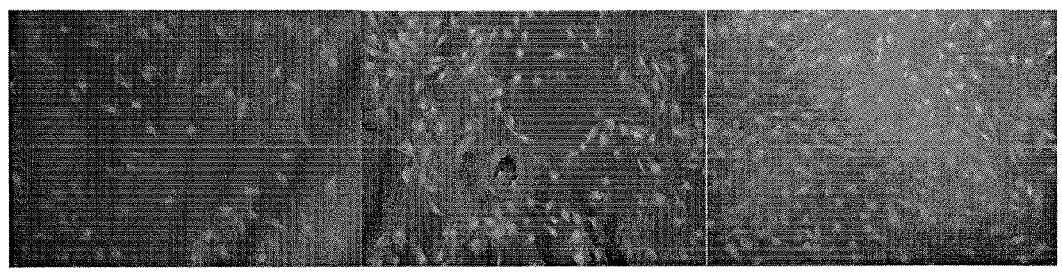
Figure 34E:
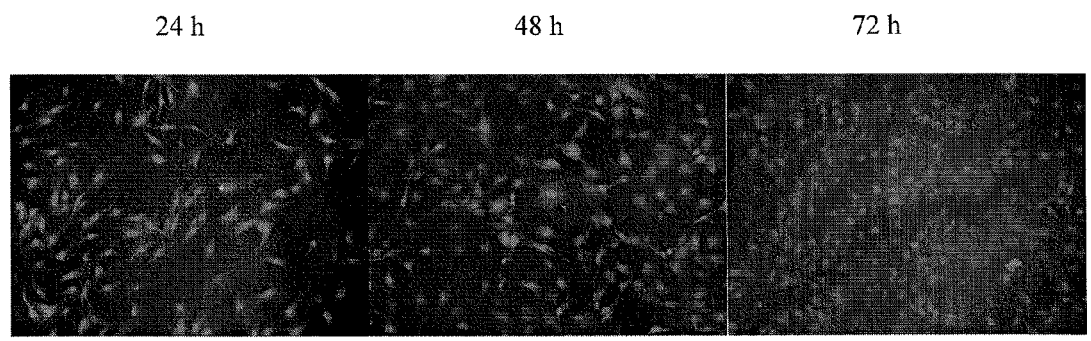
Figure 34F:
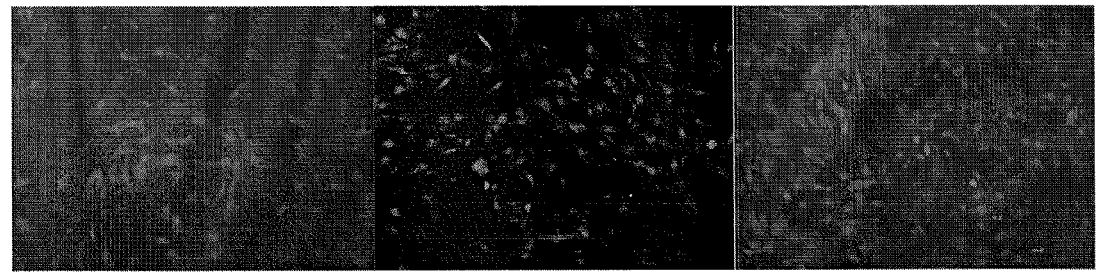
Figure 34G:
Figure 35:
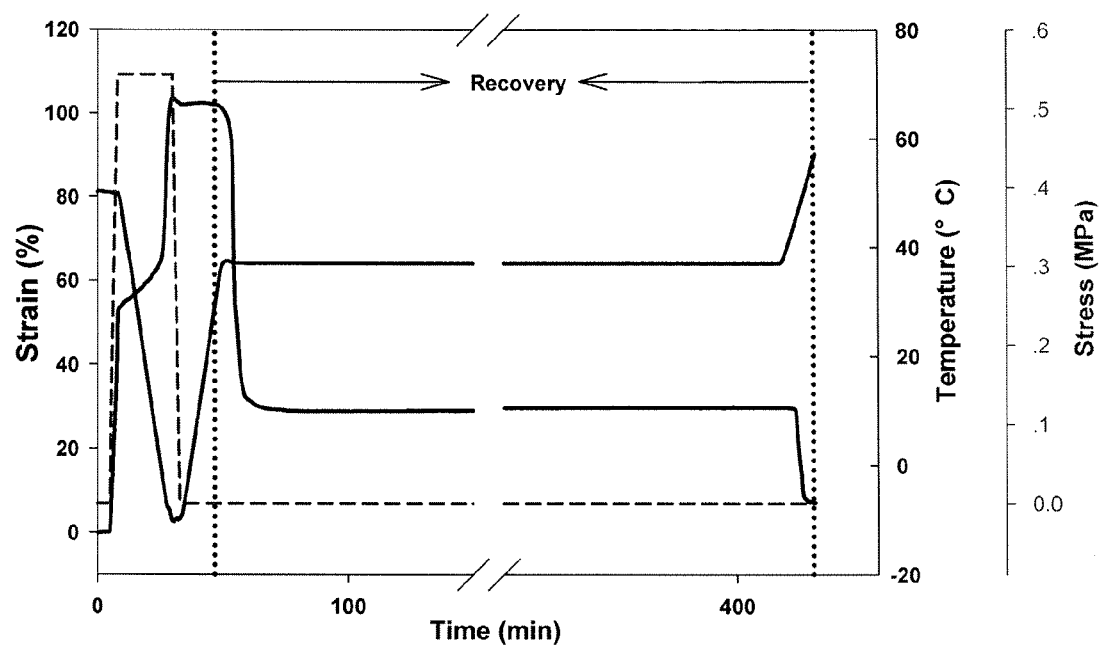
Figure 36A:
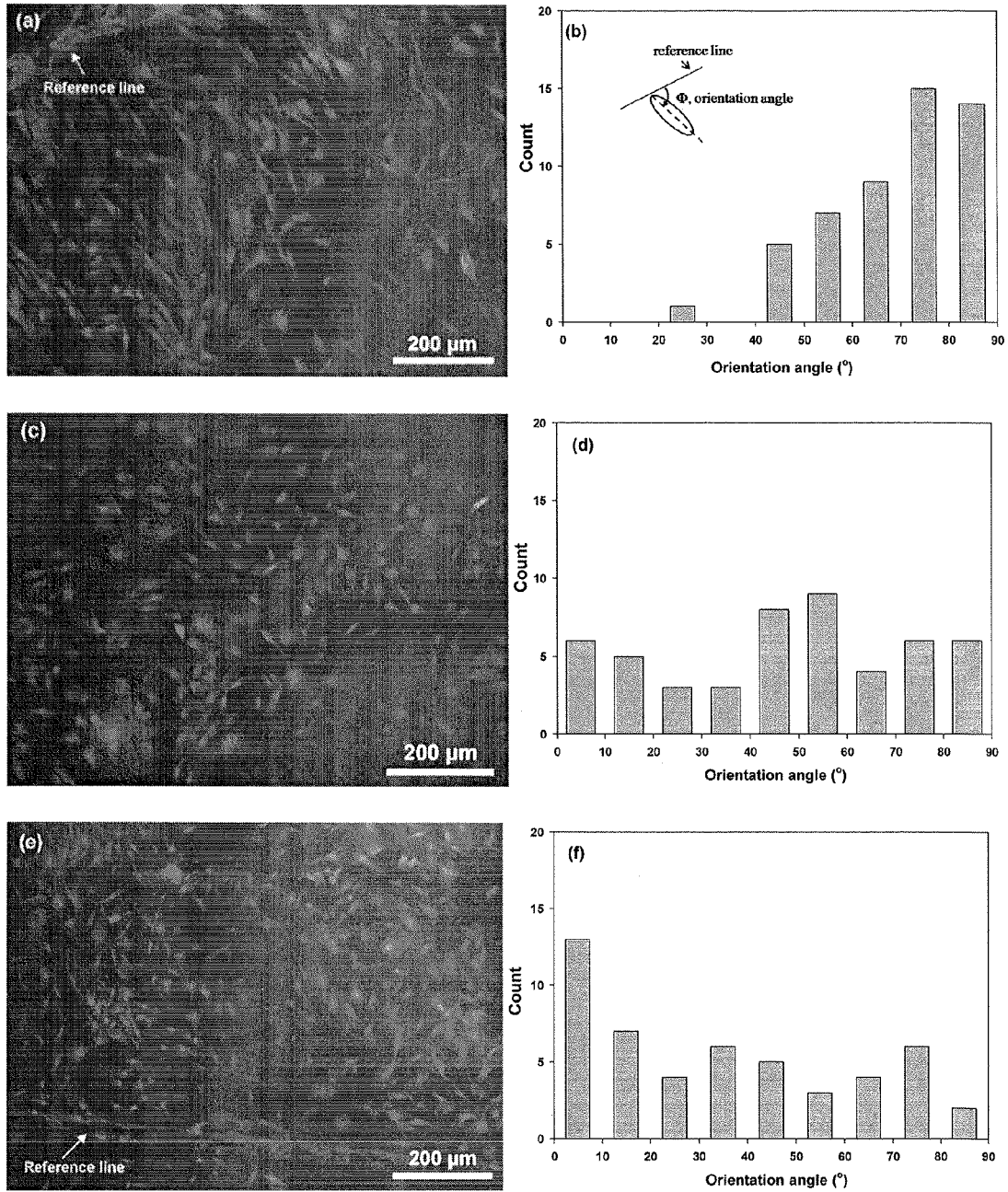
Figure 36B:
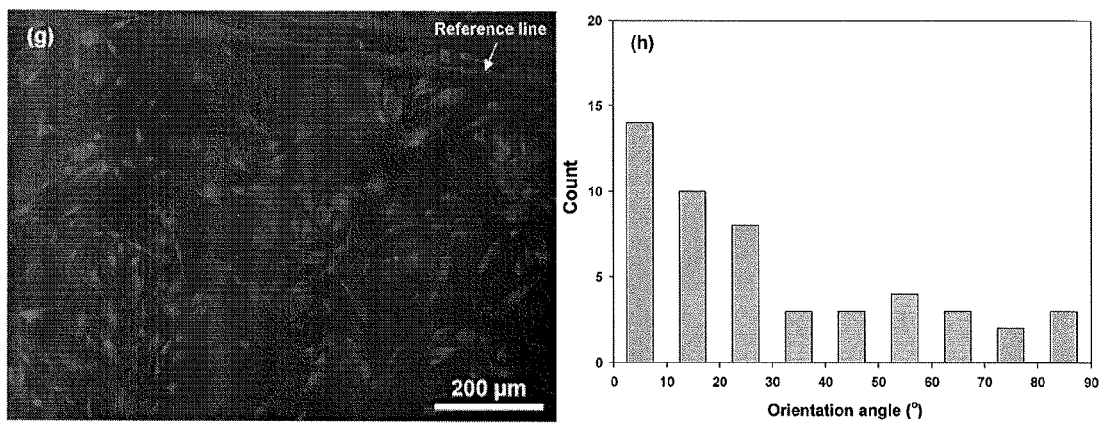

FIGS. 17A and B are graphs of PCL-PEO end-linked co-networks;

FIG. 18 is an example representative of a simple mechanism using smart bioactive hydrogel to dynamically control cell-material interactions during cell culture in vitro, according to one embodiment of the present invention;

FIG. 19A is a chart of the synthesis of PCL3k diacrylates according to one embodiment of the present invention;

FIG. 19B is a chart of the synthesis of acrylate-PEG2k-GRGDS according to one embodiment of the present invention;

FIG. 20 is a chart depicting the preparation of PCL3k/PEG2k-GRGDS co-network with PEG2k-GRGDS pendant groups;

FIG. 21 is a graph of gel fraction (open circle) and water uptake ratio (solid circle) of PCL3k/PEG2k-GRGDS co-networks (red line) and PCL3k/MPEG2kco-networks (black line) as a function of the weight percent of PEG2k-GRGDS and MPEG2k dangling chains, respectively;

FIG. 22 is differential scanning calorimetry ("DSC") thermograms of (a) PCL3k/PEG2k-GRGDS co-networks (including (i) PCL3k network, (ii) PCL3k/PEG2k-GRGDS (85/15) co-network, (iii) PCL3k/PEG2k-GRGDS (70/30) co-network, (iv) PCL3k/PEG2k-GRGDS (60/40) co-network, and (v) PEG2k-GRGDS powder; correspondingly from top to bottom) and (b) PCL3k/MPEG2k co-networks (including (i) PCL3k network, (ii) PCL3k/MPEG2k (85/15) co-network, (iii) PCL3k/MPEG2k (70/30) co-network, (iv) PCL3k/MPEG2k (60/40) co-network, and (v) MPEG2k powder, respectively from top to bottom);

FIG. 23 is a graph of wide angle X-ray diffraction ("WAXD") patterns of (a) PCL3k/PEG2k-GRGDS (60/4) co-network and (b) PCL3k/PEG2k (60/40) co-network at low temperature (0~5° C.);

FIG. 24 is 2D WAXD patterns of (a) PCL3k/PEG2k-GRGDS (60/40) and (b) PCL3k/MPEG2k (60/40) co-network at low temperature (0~5° C.), with the possible microstructures of each respective co-network depicted in (c);

FIG. 25 is a series of graphs of DSC results for (a) PCL3k/PEG2k-GRGDS hydro gels (including (i) PCL3k network, (ii) PCL3k/PEG2k-GRGDS (85/15) hydrogel, (iii) PCL3k/PEG2k-GRGDS (70/30) hydrogel, and (iv) PCL3k/PEG2k-GRGDS (60/40) hydrogel; correspondingly from top to bottom) and (b) PCL3k/MPEG2k hydro gels (including (i) PCL3k network, (ii) PCL3k/MPEG2k (85/15) hydrogel, (iii) PCL3k/MPEG2k (70/30) hydrogel, and (iv) PCL3k/MPEG2k (60/40) hydrogel from top to bottom), and (c) PCL2k/PEG2k-GRGDS (85/15) co-network (dry sample, black line) and its hydrogel (wet sample, red line), with first cooling at 10° C./min from to 70° C. to –80° C. (upper) and heating at 10° C./min from –80° C. to 70° C. (lower);

FIG. 26A is a graph of the storage modulus ("E") vs. temperature for PCL3k/PEG2k-GRGDS co-networks as a function of the weight percent of PEG2k-GRGDS components;

FIG. 26B is a graph of the storage modulus ("E") vs. temperature for PCL3k/MPEG2k co-networks as a function of the weight percent of MPEG2k components;

FIG. 26C is a graph of the storage modulus ("E") 25° C. for the PCL3k/PEG2k-GRGDS co-networks (open circles) and PCL3k/MPEG2k co-networks (solid circles) as a function of the weight percent of PEG2k-GRGDS and MPEG2k components, respectively, and for the PCL2k/PEG2k-GRGDS (85/15) co-network at 25° C. (black squares);

FIG. 27A is a graph of the one-way shape memory behavior of (a) a PCL3k network; (b) a PCL3k/PEG2k-GRGDS (85/15) co-network; and (c) a PCL3k/PEG2k-GRGDS (70/30) co-network under a constant stress (500 kPa), where the 1W-SM cycles were repeated three times from 70° C. to 0° C. at a constant ramping rate of temperature (2° C./min);

FIG. 27B is a graph of the one-way shape memory behavior of a PCL2k/PEG2k-GRGDS (85/15) co-network under a constant stress (500 kPa), where the temperature was ramped from 70° C. to –20° C. at 2° C./min during both heating and cooling steps;

FIG. 28A is a graph of two-way shape memory behavior for: (a) PCL3k network, (b) PCL3k/PEG2k-GRGDS (85/15) co-network, (c) PCL3k/PEG2k-GRGDS (70/30) co-network and (d) PCL2k/PEG2k-GRGDS (85/15) co-network under a constant stress (500 kPa);

FIG. 28B is a graph of two-way shape memory behavior of PCL3k/PEG2k-GRGDS (85/15) co-network during isothermal process under different temperatures: (black) 41° C., (red) 39° C., (blue) 37° C., (pink) 35° C., and (cyan) 33° C.;

FIG. 29 is a graph of the storage modulus ("E") at 70° C. for the PCL3k/PEG2k-GRGDS co-networks (open circles) and PCL3k/MPEG2k co-networks (solid circles) as a function of the weight percent of PEG2k-GRGDS and MPEG2k components, respectively;

FIG. 30A is a graph of one-way shape memory behavior for the PCL3k/PEG2k-GRGDS (60/40) co-network;

FIG. 30B is a graph of two-way shape memory behavior for the PCL3k/PEG2k-GRGDS (60/40) co-network;

FIG. 31A is a graph of normalized cell attachment of fibroblasts on the surface of PCL3k network, PCL3k/MPEG2k (85/15) hydrogel, PCL3k/PEG2k-GRGDS (85/15) hydrogel, PCL2k/PEG2k-GRGDS (85/15) hydrogel, and TCPS cultured for 3 h, where symbols "*" and "#" represent statistical significance (p<0.05);

FIG. 31B is a graph of normalized cell attachment of fibroblasts on the surface of PCL3k network, PCL3k/MPEG2k (85/15) hydrogel, PCL3k/PEG2k-GRGDS (85/15) hydrogel, PCL2k/PEG2k-GRGDS (85/15) hydrogel, and TCPS cultured for 6 h, where symbols "*" and "#" represent statistical significance (p<0.05);

FIG. 31C is a graph of normalized cell attachment of fibroblasts on the surface of PCL3k network, PCL3k/MPEG2k (85/15) hydrogel, PCL3k/PEG2k-GRGDS (85/15) hydrogel, PCL2k/PEG2k-GRGDS (85/15) hydrogel, and TCPS cultured for 12 h, where symbols "*" and "#" represent statistical significance (p<0.05);

FIG. 32A is a graph of normalized cell attachment of fibroblasts on the surface of PCL3k/PEG2k-GRGDS (85/15), PCL3k/PEG2k-GRGDS (70/30), and PCL2k/PEG2k-GRGDS (85/15) hydrogel cultured for 3 h;

FIG. 32B is a graph of normalized cell attachment of fibroblasts on the surface of PCL3k/PEG2k-GRGDS (85/15), PCL3k/PEG2k-GRGDS (70/30), and PCL2k/PEG2k-GRGDS (85/15) hydrogel cultured for 6 h;

FIG. 32C is a graph of normalized cell attachment of fibroblasts on the surface of PCL3k/PEG2k-GRGDS (85/15), PCL3k/PEG2k-GRGDS (70/30), and PCL2k/PEG2k-GRGDS (85/15) hydrogel cultured for 12 h;

FIG. 33 is a series of representative morphological images of fibroblasts cultured for 12 h on the surface of (a) PCL3k network, (b) PCL3k/MPEG2k (85/15) hydrogel, (c) PCL3k/MPEG2k (70/30) hydrogel, (d) PCL3k/PEG2k-GRGDS (85/15) hydrogel, (e) PCL3k/PEG2k-GRGDS (70/30) hydrogel, (f) PCL2k/PEG2k-GRGDS (85/15) hydrogel and (g) TCPS, wherein the cell seeding density was $3.1 \times 10^4$ cells/cm$^2$, and the scale bar in the panel represents 200 μm for all the images;

FIGS. 34A-G are representative images depicting the cell morphology of fibroblasts cultured for 24, 48 and 72 h on the surface of (a) PCL3k network, (b) PCL3k/MPEG2k (85/15) hydrogel, (c) PCL3k/MPEG2k (70/30) hydrogel, (d) PCL3k/PEG2k-GRGDS (85/15) hydrogel, (e) PCL3k/PEG2k-GRGDS (70/30) hydrogel, (f) PCL2k/PEG2k-GRGDS (85/15) hydrogel, and (g) TCPS, wherein the cell seeding density was $1.2 \times 10^4$ cells/cm$^2$, and the scale bar in the panel represents 200 μm for all the images;

FIG. 35 is a graph of isothermal shape recovery process of the stretched PCL2k/PEG2k-GRGDS (85/15) co-network film at 37° C.;

FIG. 36A is a series of representative images (left side) and orientation distribution angles (right side) of: fibroblasts cultured on the stretched PCL2k/PEG2k-GRGDS (85/15) hydrogel film in panels (a) and (b), respectively; fibroblasts cultured on the un-stretched PCL2k/PEG2k-GRGDS (85/15) hydrogel film in panels (c) and (d), respectively; and fibroblasts cultured on the stretched (a) sample only at 28° C. for 5 h before observation; and FIG. 36B is a representative image (left side) and orientation distribution angle (right side) of fibroblasts cultured on the stretched PCL3k/PEG2k-GRGDS (85/15) hydrogel film ($T_m$=43.2° C.), respectively.

DETAILED DESCRIPTION OF THE INVENTION

Figure 1:
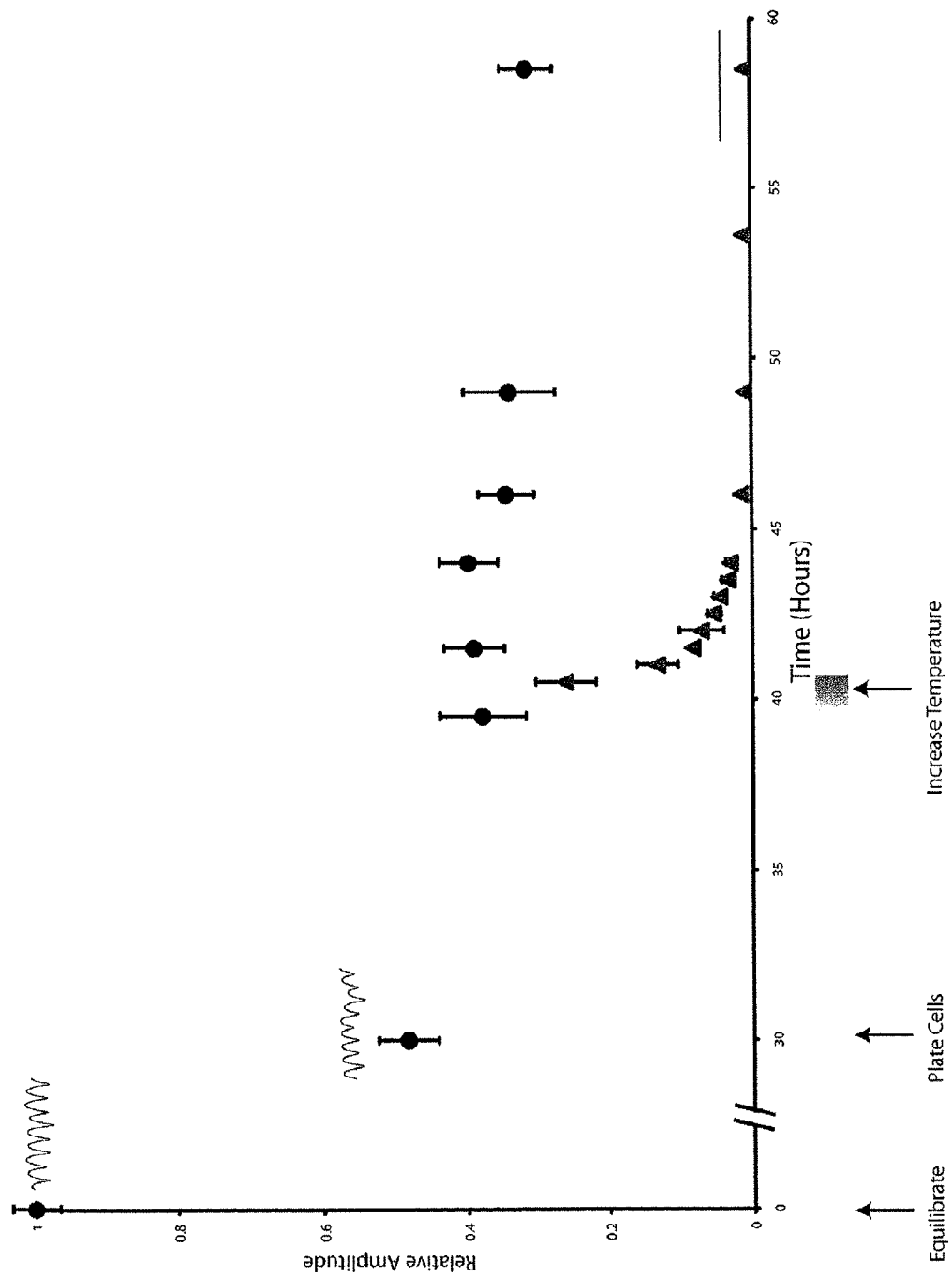
FIG. 1 is a graph of a shape memory thermomechanical cycle.
Figure 2:
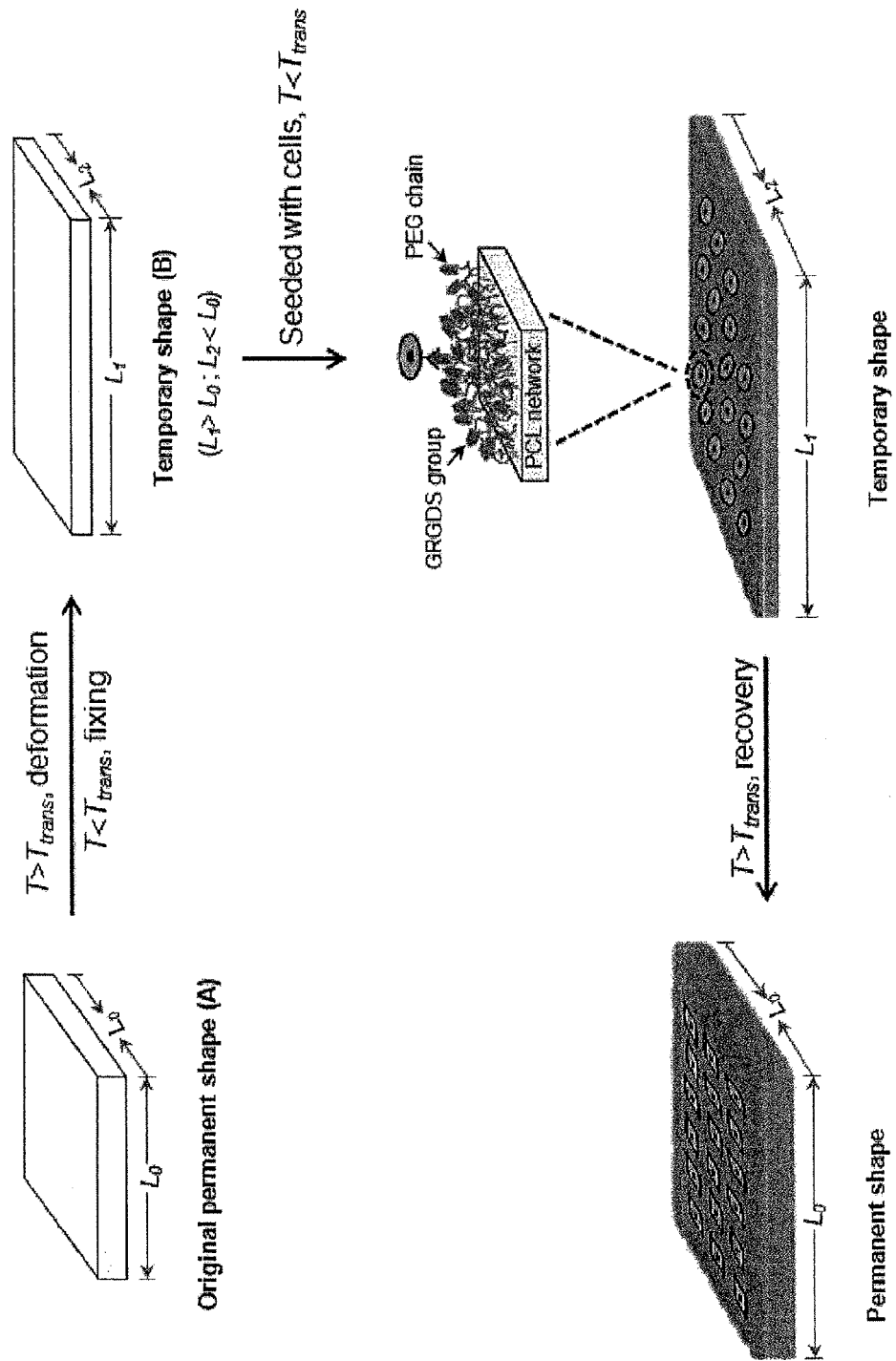
FIG. 2 is a series of images of poly(lactide)-POSS scaffold.
Figure 3:
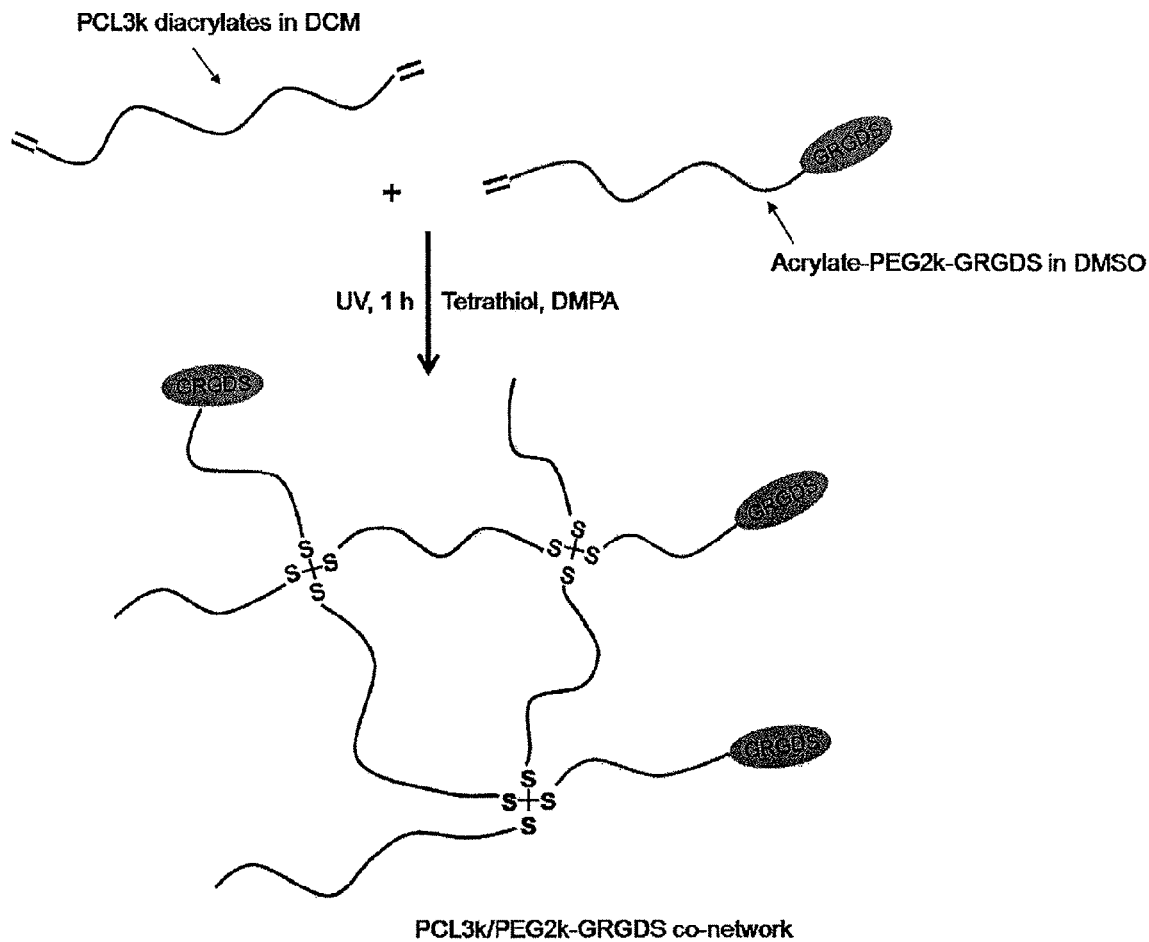
FIG. 3 is a series of images of cells aligned on an SMP scaffold.
Figure 4:
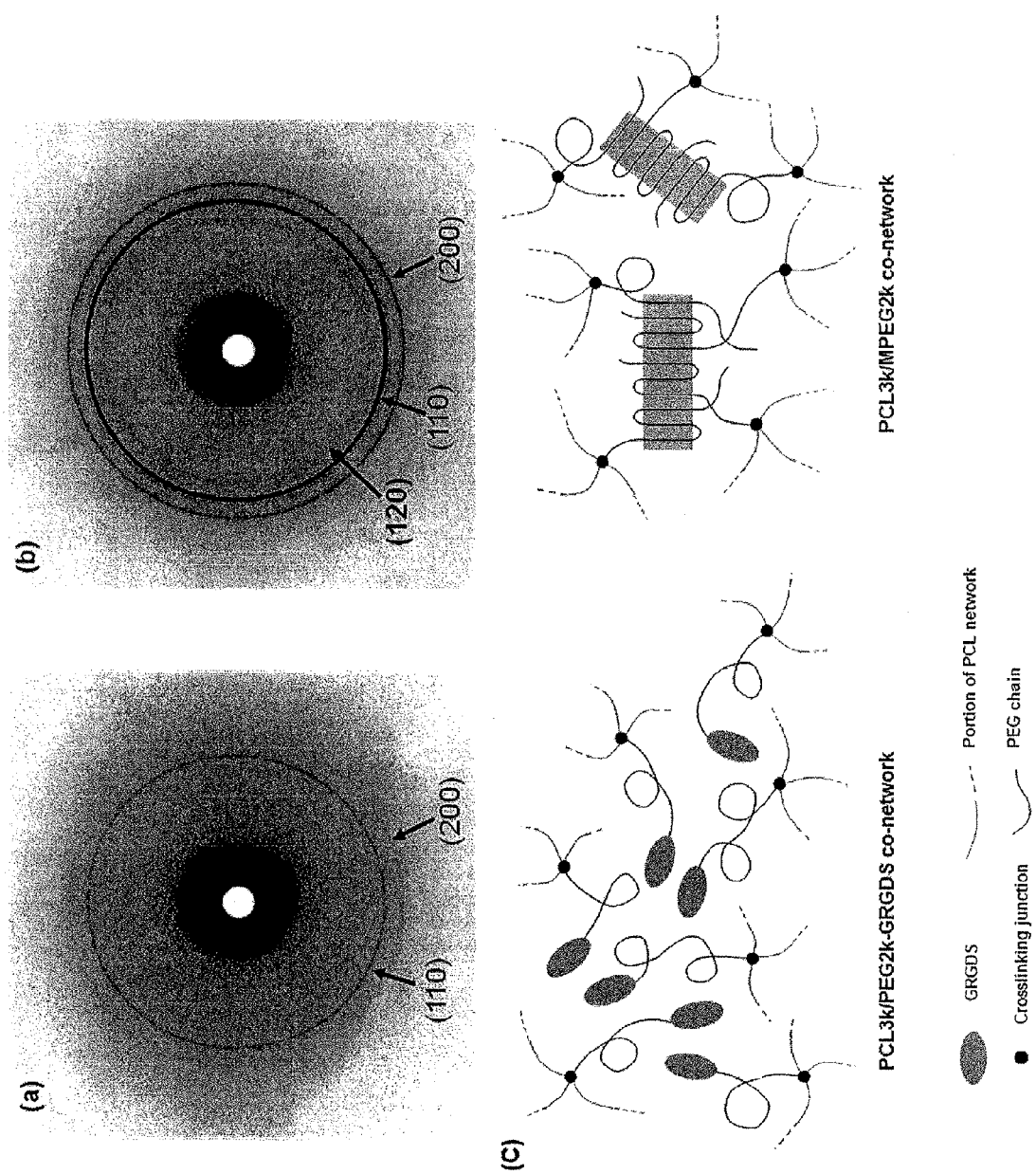
FIG. 4 is an image of cells changing shape in response to SMP-driven changes in topography.
Figure 5:
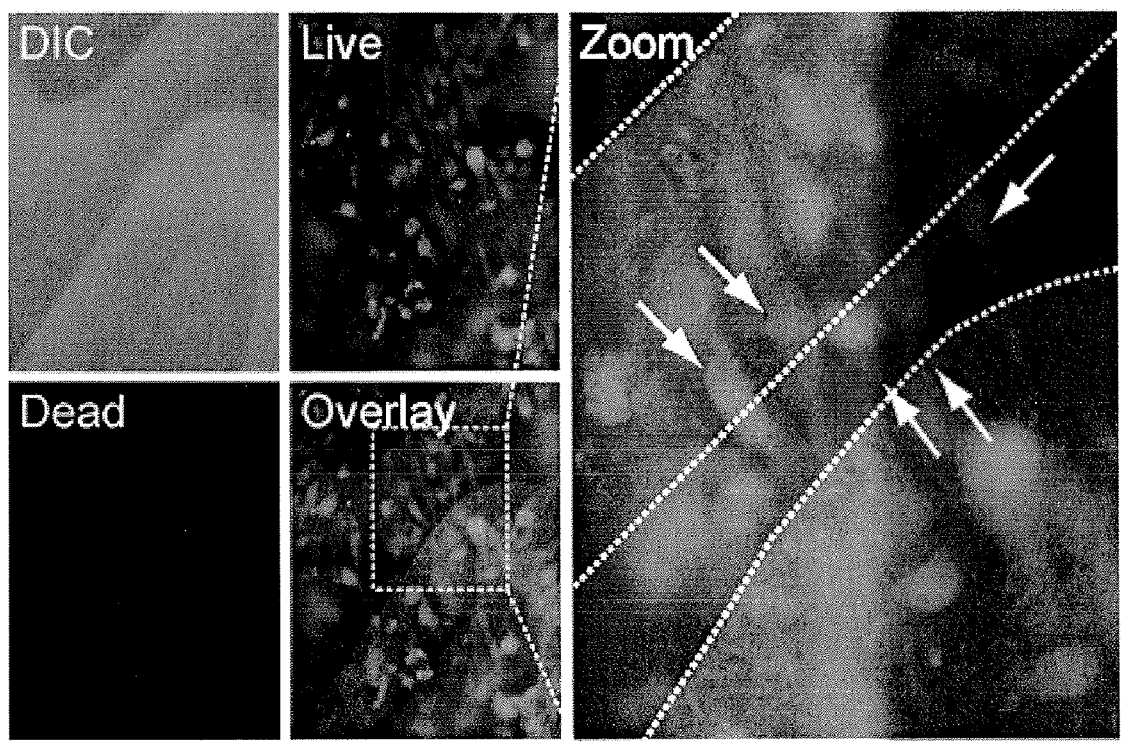
FIG. 5 is an image of cells spanning two scaffold struts.

Referring now to the drawings, wherein like reference numerals refer to like parts throughout, there is seen in FIG. 2 tissue engineering substrates, referred to herein as scaffolds, that include dynamic changes of stiffness and shape for significantly broadening the functionality of cell culture substrates. In particular, the present invention augments the toolbox used by researchers in the fields of biology and biomedical engineering to include active 2D and 3D culture substrates, thereby transforming the experimental designs and potentially engendering new discoveries.

Referring to FIGS. 3 through 6, the present invention includes degradable, multiblock polyurethanes that exhibit shape-memory properties and have material formulations and substrate geometries and scaffold architectures that provide exquisitely controlled dynamic changes in substrate and scaffold shape. The present invention may be useful as scaffolds in established musculoskeletal and cardiovascular tissue-engineering protocols to determine the extent to which dynamic changes in scaffold shape affect cell phenotype.

The present invention uses the approach of systematically varying material design to develop biocompatible SMPs that can be triggered to undergo shape changes under tissue-culture-compatible conditions. At the same time, the present invention involves the design of archetypal (primitive) scaffold architectures that produce growth, contraction, and remodeling during shape-memory recovery. The methodologies for fabricating these architectures are developed concurrently with the materials design work to allow iterative, coordinated refinement of material and architecture. The resulting SMP scaffolds could be tested in established cartilage, tendon, cardiovascular, or other tissue-engineering protocols and the extent to which dynamic changes in scaffold shape affect cell phenotype would be determined by biochemical and biomechanical comparison to static control scaffolds.

EXAMPLE 1

Figure 7:
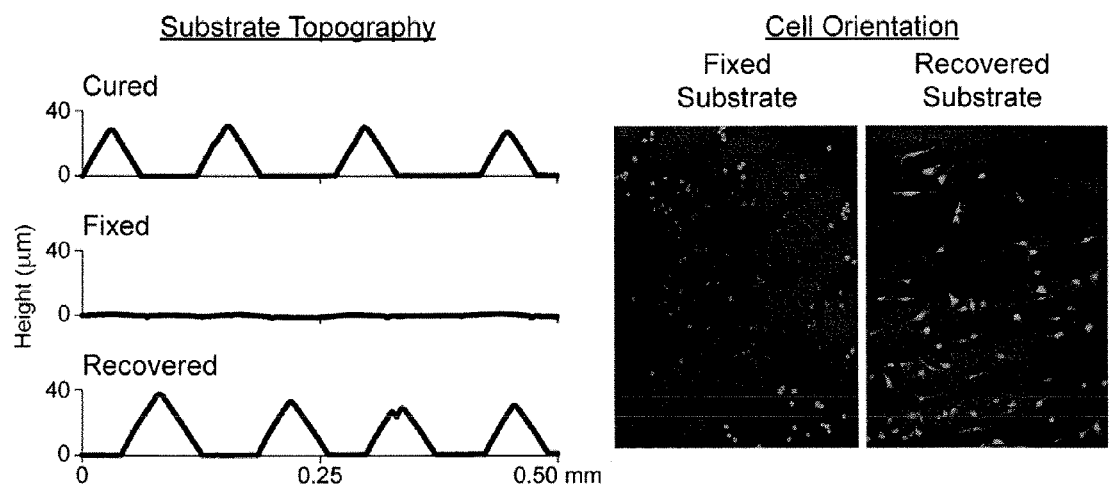
FIG. 7 is a graph of substrate topography (left) and a series of images of cell response (right)

To test the hypothesis that programmed changes in surface topography of an SMP substrate could be used to direct cell behavior, cell orientation on an SMP substrate programmed to change from a flat to ridged topography via a hydro-thermal trigger has been analyzed. Referring to FIG. 7, a photocured, glassy SMP was cured on a vinyl record to produce films with an equilibrium surface topography of triangular ridges. Samples were then flattened and fixed by compression above $T_g$ and cooling to room temperature under force. C3H10T1/2 cells were allowed to attach for 3.5 h at 23° C. and then shape recovery was triggered by increasing to 37° C. (above the hydrated $T_g$, which is lover by 5-10° C. than the dry $T_g$).

Three groups were tested to: (i) measure surface topography by profilometry after curing, after fixing, and after recovering (n=3); (ii) image cell orientation before recovery (n=2); and (iii) image cell orientation after recovery (n=3). Unflattened samples were the control. As seen in FIG. 7, the findings show that a programmed change in surface topography of an SMP substrate can be used to direct cell orientation. Before shape recovery, attached cells had a random cell orientation angle with little spreading (1.31±0.09 ellipse aspect ratio). After recovery, attached cells were oriented along the ridges with increased spreading (3.44±0.35 aspect ratio, p=0.004). The results suggest that substrates that incorporate surface shape memory could provide an unprecedented approach for controlling cell behavior during cell culture.

The present invention could be tested using strut-based scaffolds whose equilibrium (programmed) shape is determined at the time of crystallization during high-resolution solid freeform fabrication ("SFF") extrusion of thermoplastic shape memory polymers of the type described above. Temporary shapes can then be set as the starting configuration in place during initial cell adhesion and the shape change toward the programmed shape triggered by cell culture conditions of heating and hydration. Given the flexibility in the SFF process and the excellent shape fixing and recovery of the SMPs selected, strut geometry transitions may be conceived (from fixed to programmed) that expand or contract and to varying degrees. Material selection determines initial glass transition temperature and swelling degree, thus dictating the rate of recovery triggered by the glass-rubber transition event.

EXAMPLE 2

To test the hypothesis that programmed changes in surface topography of an SMP substrate could be used to direct cell behavior, cell orientation on an SMP substrate programmed to undergo changes in surface topography triggered by a temperature tailored to fall within the temperature range compatible with mammalian cell culture has been analyzed.

Materials and Methods

To exploit surface shape memory in a cell culture context, the glassy SMP Norland Optical Adhesive 63 ("NOA-63") (Norland Products, Cranbury, N.J.) was adapted for use under cell culture conditions. NOA-63 is a commercial optical adhesive supplied as a 100% solids prepolymer with a photoinitiator. The SMP was used as received and injected between an aluminum block and a glass slide with a 1 mm thick Teflon spacer. The polymer was cured for 20 min on a hot plate at 125° C. with Spectroline SB-100PC 365 nm UV light source (Westbury, N.Y.). The film was removed from the mold, placed on the hot plate, and cured with heat and UV for an additional 3.75 h. The material was stored desiccated at T=20° C.

Bisphenol A diglycidyl ether/Diethylimene triamine epoxy was cured on a vinyl record (Liberace, Mr. Showmanship, Dot Records) at room temperature for 16 h and then post cured at 150° C. for 2 h to increase $T_g$ above the embossing temperature. A wax-based release coating was used following manufacturer instructions to allow removal of the brittle epoxy from the record. The NOA film was cut into approximately 10×10 mm² pieces. These pieces were arranged on the epoxy embosser and compressed using a Carver press with heating/water-cooling platens. 4.9 MPa was applied to the samples at 90° C. and held for 1 min. Platen cooling was started and the pressure was removed at 20° C.

Sample topography was measured using a KLA Tencor P16+ stylus profilometer (Milpitas, Calif.). Three 1200 μm long scans were performed at 600 μm intervals near the center of the sample at 50 μm/s. The raw data was exported and amplitude was quantified after leveling in a custom MATLAB program.

To produce a static control substrate with a grooved topography, embossed samples were equilibrated in complete growth medium for 30 h in a 30° C. incubator. Sylgard 184 (Dow Corning, Midland, Mich.) was mixed at a 5:1 base-to-curing-agent ratio, cast on a glass slide and cured for approximately 5 min at 80° C. (until reaching the gel point). The Sylgard was cooled for 10 min in 4° C. The equilibrated samples were removed from the incubator, gently placed on a delicate task wipe to remove excess liquid, and then placed face down on the cast Sylgard. The equilibrated NOA63 samples were removed from the Sylgard after a 12 h cure at room temperature. The Sylgard was post cured at 80° C. for 5 min. NOA-63 was poured onto the Sylgard mold and cured for 25 min at room temperature with a 1000 W 365 nm UV lamp. The NOA was removed and cured for an additional 3 h 35 min at 125° C. with UV.

C3H10T1/2 mouse embryonic fibroblasts were purchased from ATCC (Manassas, Va.) and cultured in complete growth medium: BME (Invitrogen, Carlsbad, Calif.) supplemented with 10% fetal bovine serum (Invitrogen), 1% penicillin/streptomycin (Invitrogen), and 1% Glutamax in a 37° C. humidified incubator with 5% $CO_2$. Cells were passaged at 80% confluence using 0.25% trypsin-EDTA solution (Invitrogen). Cells were collected for use in subsequent steps described below.

Cells were stained with LIVE/DEAD, Cellmask deep red plasma membrane stain, and Alexa Flour 647 conjugated phalloidin (Invitrogen). LIVE/DEAD stain was used at 2 μM for Calcien AM and EthD-1 following manufacturer protocol. Cellmask was used at 5 μl/ml and exposed for 5 min at 30° C. Cells were fixed with 4% formaldehyde (16% formaldehyde [Ted Pella] diluted in DPBS [Invitrogen]) for 10 min at 30° C. Samples were mounted in Prolong Gold (Invitrogen). Cells were stained with phalloidin following manufacturer protocol and mounted in Prolong Gold. Cells stained with LIVE/DEAD and Cellmask were imaged on a Leica DMI 4000B with a DFC 340 FX camera. The GFP and N3 filter cubes were used for LIVE/DEAD cells. The Y5 filter cube was used for Cellmask stained samples. Polarized white reflected light images were also acquired to show sample topography. Cells stained with phalloidin were imaged with a 20x/0.xx NA or a 40x/0.xx NA objective. Phalloidin stained cells were also imaged on a Zeiss LSM 710 confocal laser scanning microscope using a 20x/0.8 NA objective.

Cell morphometric data was quantified by manually tracing cell outlines from Cellmask stained samples using ImageJ. The traces were filled and binary images were created. The analyze particles function was used to determine cell area, perimeter, shape index ($p^2/4\pi A$), and angle. Cell angles we defined from 0-180°, and 90° was defined as the direction of the grooves on grooved samples. Cell viability was calculated by counting the number of live and dead cells for a 2052 μm×1539 μm area of the sample.

For cell de-alignment experiments, embossed samples, static grooved samples, and embossed samples recovered to a flat topography by heating at 90° C. for 5 min were cleaned by vortexing in 70% ethanol for 20 s and then sterilized by exposure to UV under a biological safety cabinet. Samples were then placed in a 96-well plate and 150 μl of complete growth medium was added. These samples were then equilibrated for 30 h in 30° C. incubator. 150 μl of cells diluted to 20,000 cells/ml were added to each sample. Three groups of embossed, flat, and static samples were cultured at 30° C. for 9.5 h. One group was removed and stained, a second group was moved to a 37° C. incubator for an additional 19 h and then stained, and a third group was kept at 30° C. for an additional 19 h and then stained. One group of flat and static samples was cultured at 37° C. for 9.5 h and then stained. The cell de-alignment experiment was repeated from sample cure three times. A Kruskal-Wallis test was performed to determine significance at $p<0.05$ and multiple comparisons were performed by permutation tests using custom MATLAB code.

To determine substrate recovery kinetics, embossed samples not plated with cells were incubated in parallel with cell plated samples and removed at pre-selected times. Profilometry following recovery was performed on the same area of the sample as before. Percent recovery was calculated for individual samples as (1−(final amplitude)/(initial amplitude))×100.

Results

To exploit surface shape memory in a cell culture context, NOA-63 was adapted for use under cell culture conditions. It has previously been shown that the material exhibits 1WSM around its glass transition temperature ($T_g$). In addition, it was found that increasing the temperature during UV cure raised the $T_g$. NOA-63 takes up water which plasticizes the material, lowering the $T_g$. A combination of increasing the dry $T_g$ by heating during curing and lowering the $T_g$ via water uptake was used to tune the transition to fall into a cell-compatible range.

Figure 8:
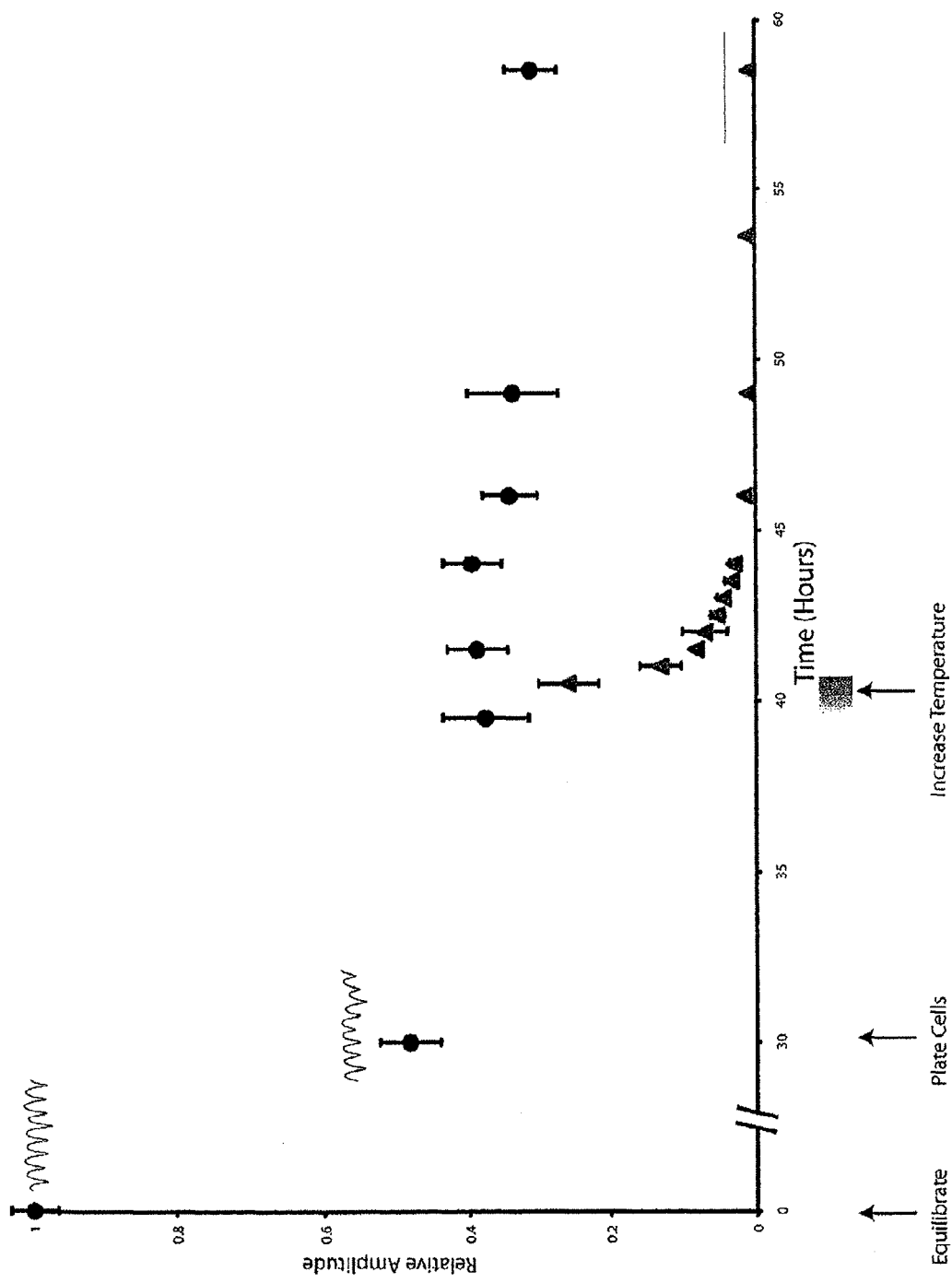
FIG. 8 is a graph of active cell culture substrate amplitude recovery, where circles represent hydration in complete growth medium at 30° C., triangles show data regarding recovery triggered by moving the substrate to a 37° C. incubator, and traces next to data points are contact profilometry scans of representative samples.

Surface shape memory was employed to prepare substrates that changed from a grooved topography to a flat surface. To prepare shape memory substrates in their permanent, flat shape, the SMP was injected by syringe into a glass and aluminum chamber and performed an initial cure at 125 C. with a 1000 W 365 nm UV lamp for 20 min. To perform the final cure, the sample was removed from the chamber and cured under the same conditions for 3.75 h. Dynamic mechanical analysis ("DMA") of the SMPs in tension showed a tan delta peak at ~74° C., with a glassy modulus of ~2500 MPa and a rubbery plateau of ~25 MPa. The SMPs were then embossed with an epoxy negative of a vinyl record (Liberace, Mr. Showmanship, Dot Records) with ~30 μm triangular peaks spaced ~150 μm apart. A Carver hydraulic hot press was used to apply 4.9 MPa at 90° C. The samples were then cooled to 20° C. over 5 min, fixing the temporary grooved topography. Embossing produced rounded peaks with a peak to trough amplitude of ~25 μm, as shown in FIG. 8. As shown by the figure, the relative amplitude of embossed substrates decreases over 58.5 h when hydrating in complete growth medium at 30° C. (circles). Triggering recovery by moving the substrates to a 37° C. incubator increases the rate of recovery and near complete recovery occurs within 9.5 h (triangles). Error bars represent one standard deviation (n=4-6). Text below the graph in FIG. 8 indicates experimental landmarks. The gradient indicates time period of temperature increasing from 30° C. to 37° C. Traces next to data points are contact profilometry scans of representative samples. Scale for all traces is the same with maximum observed amplitude among samples of 26 μm.

For a 2D (topographical) SMP substrate to function as an active cell culture substrate under a temperature trigger, the SMP substrate must maintain a stable temporary topography at a temperature compatible with cell culture, and must then recover its permanent topography following either a transient or prolonged increase in temperature that also does not adversely affect the cell behavior of interest. The temporary grooved topography was found to be unstable for 30 to 40 h after immersion in cell growth media at 30° C. (see FIG. 8). To create samples with relative stability but large enough groove amplitude to influence cell alignment, embossed samples were equilibrated for 30 h at 30° C. in complete growth medium. Under these conditions, the grooved samples were found to partially recover to a peak to trough amplitude of ~13 μm. When temperature was then increased to the standard cell culture temperature of 37° C., ~99% recovery from the initial amplitude was observed, as shown in FIG. 8. UV sterilization after temporary topography fixing led to additional photo-initiated cross linking, resulting in ~0.3 μm grooves remaining after recovery. Therefore, the functional range of recovery for the SMP substrate employed in active cell culture experiments was ~13 μm.

To determine whether a change from a grooved topography to a flat surface can be used to control cell behavior, C3H10T½ mouse embryonic fibroblasts were seeded on the temporary grooved topography following equilibration of the substrate for 30 h at 30° C. in complete growth medium. Cell seeded substrates were then incubated at 30° C. for 9.5 h, which allowed time for cell attachment and spreading. After 9.5 h, some samples were removed from culture and stained to determine cell alignment, cell viability, and microfilament organization prior to shape memory recovery. Shape memory recovery and the change to the flat surface were then triggered by moving the substrate to a 37° C. incubator, where samples were cultured for 19 h. Topographic recover was completed approximately 9.5 h after the move to 37° C. After the complete 28.5 hour culture period, samples were removed from culture and stained to determine cell alignment, cell viability, and microfilament organization following shape memory recovery. Cell alignment per sample was quantified by the mean resultant vector length (R), which was used as a measure of the dispersion of individual cell angles.

The embossed amplitude of 25.6+/−0.8 μm recovered to 12.6+/−1.5 μm after 30 h equilibration at 30° C. After the multi-well plate containing the samples was moved to a 37° C. incubator, the majority of the recovery occurred over 3.5 h to 1.1+/−0.2 μm and the amplitude recovered to ~0.3+/−0.1 μm by 9.5 h with no detectable change over the final 9.5 h. Samples kept at 30° C. for the entire 28.5 h culture period showed an amplitude decrease of 4.5 um, from 12.6+/−1.5 μm to 8.1+/−1.1 μm. The percent recoveries over time for samples recovered at 30° C. and at 37° C. are fit well by a multiple exponential decay with 2 decay processes decaying to an arbitrary asymptote. The fit indicates that recovery at 30° C. will cause the material to asymptote to ~75% recovery (~6 um) by 150 h.

Figure 9:
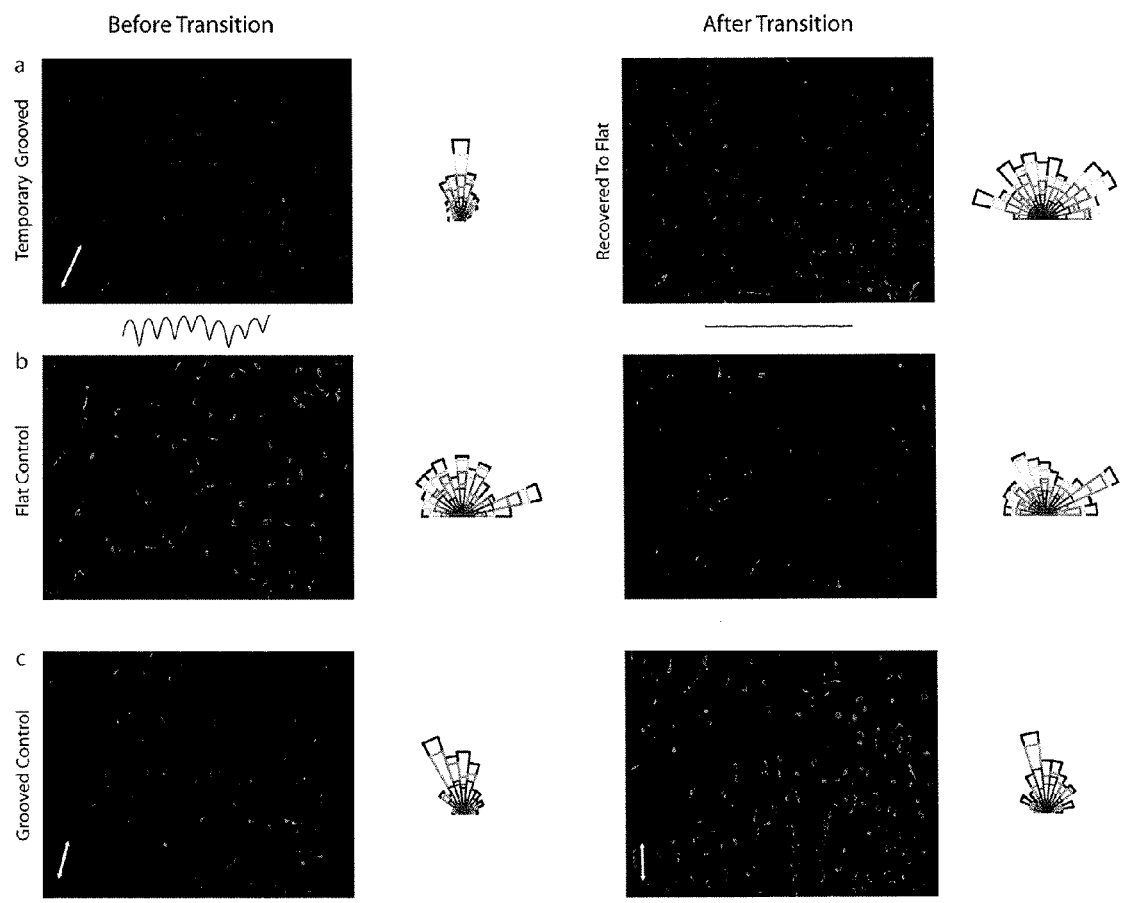
FIG. 9 is a series of pictures showing the orientation of cells stained with Cellmask Deep Red Plasma Membrane stain under varying conditions.

The results show that a change from a grooved topography to a flat surface can control cell behavior. Topographic transition caused cells to change from preferential alignment along the grooves to a more random, unaligned orientation, as shown in panel (a) of FIG. 9. Prior to shape memory recovery, cells were elongated and aligned parallel to the direction of the grooves with an R of ~0.8. Following shape memory recover, cells were randomly oriented with an R of ~0.66. Control groups in which the substrate did not change topography confirmed that the observed change in cell alignment was a result of the change in topography rather than the change in temperature, as shown in panels (b) and (c) of FIG. 9. Rose plots show the large dispersion of cell angles on flat and recovered to flat samples as well as the small dispersion for grooved samples.

Figure 10:
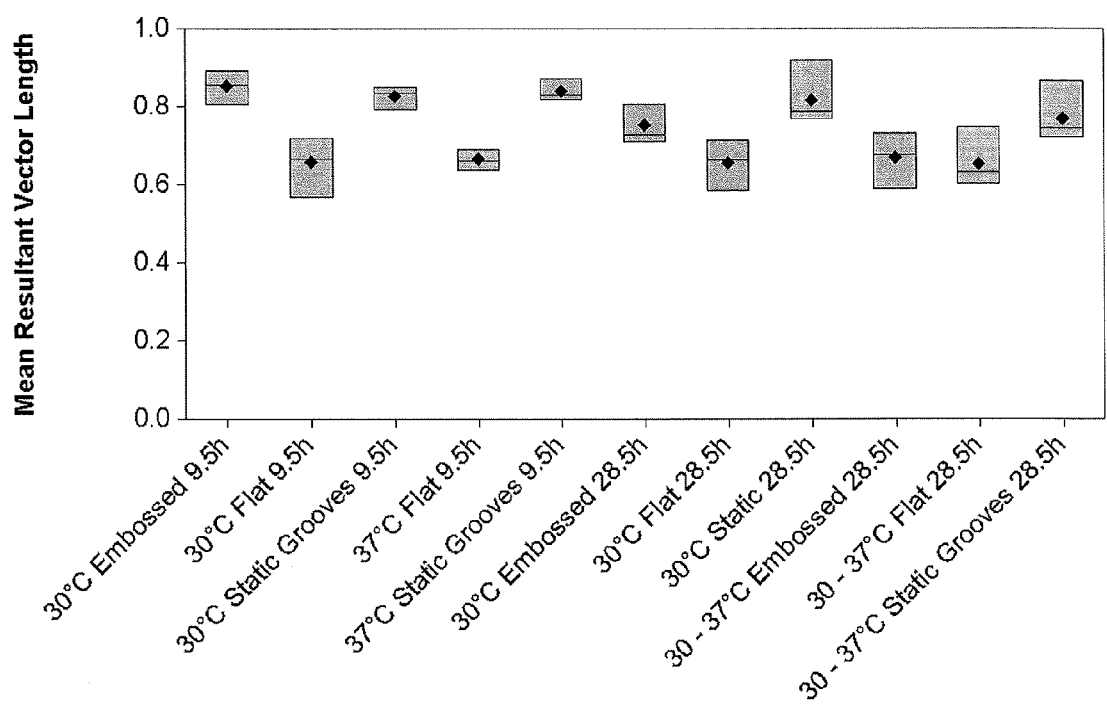
FIG. 10 is a box plot of mean resultant vector length, where boxes are range boxes, lines indicate the median, and diamonds indicate the mean.

The R of cells on temporary grooved topographies before recovery was significantly different than after recovery and all other flat controls, as shown in FIG. 10. Those samples with grooves substrates showed R>0.8, while those on flat or recovered to flat samples showed R of 0.60-0.65, close to the value for a uniform distribution, 0.63. The R for dynamic samples that were kept from transition by maintaining at 30° C. throughout culture was 0.7, and between the values for flat and static or before transition dynamic samples.

Viability was greater than 95% for all groups, including those that went through a simultaneous topography and temperature change, a temperature change alone, or remained at 30° C. for the entire culture period. Cell detachment was not observed as similar numbers of cells were attached before and after transition.

Figure 11:
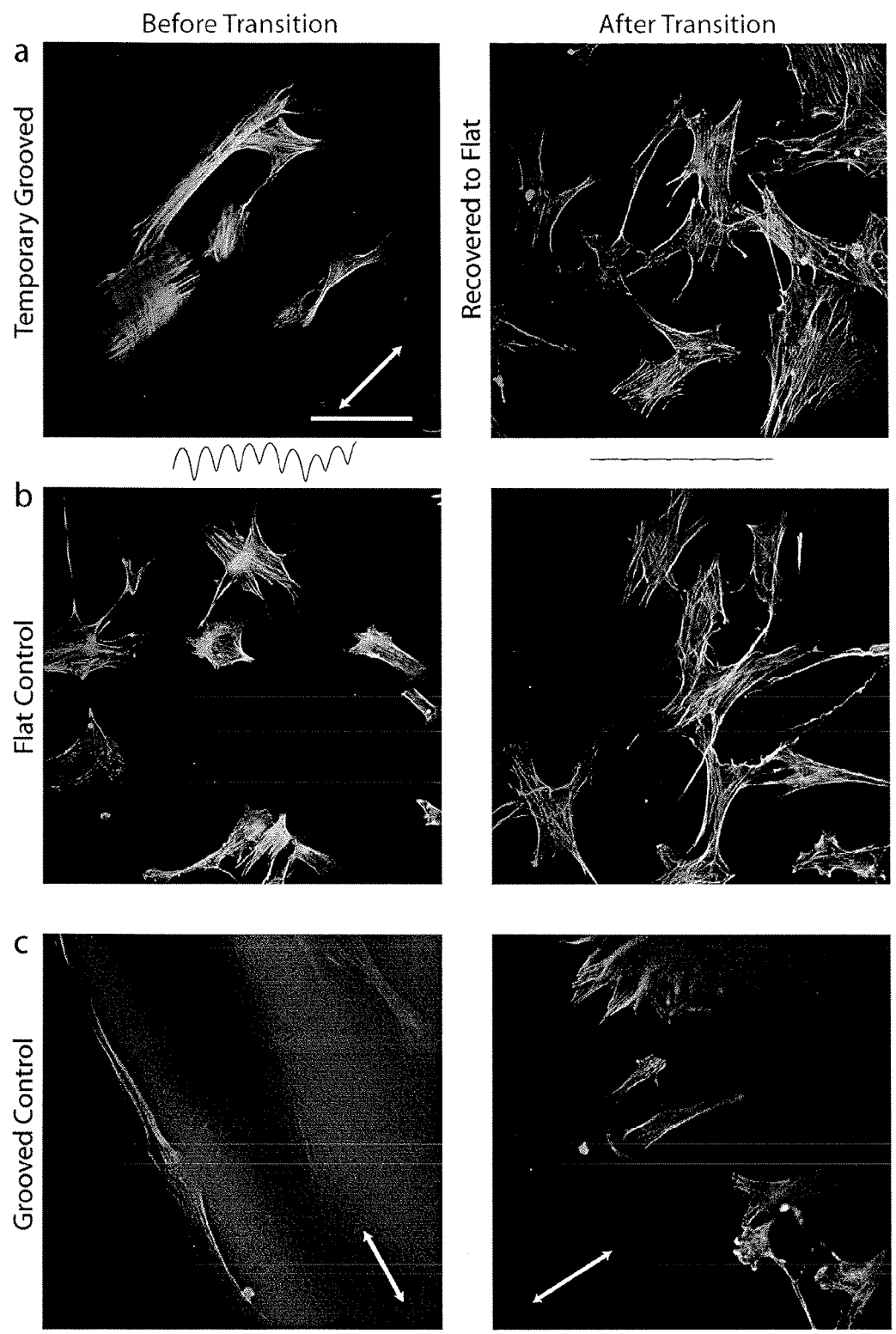
FIG. 11 is a series of confocal images of cells stained with phalloidin under varying conditions.

Phalloidin-stained samples showed cells with microfilaments aligned along the direction of the grooves for static controls on dynamic samples before transition. Cells on dynamic substrates after transition showed randomly distributed microfilaments, as shown in panel (a) of FIG. 11. Controls did not show reorganization, as shown in panels (b) and (c) of FIG. 11.

No significant differences were found for cell area, cell perimeter, or cell shape index (data not shown). This could be due to the number of cell morphologies that the fibroblasts exhibit, as well as an effect of the 2D projected image of cells on the 3D micron-scale topography.

EXAMPLE 3

To determine the fundamental shape-memory characteristics of particular strut design, and to determine the ways in which those characteristics affect cell shape before, during, and after shape-memory recovery, unit-cell archetypes, such as square, triangular (FIG. 12), and circular geometries may be tested and used. The shape memory characteristics of the unit cells will be tested using standard methods, yielding quantitative measures of shape fixing ($R_f$), shape recovery ($R_r$), shape memory fill factor (sharpness of recovery), and constrained-strain stress recovery. The kinetics and completeness of shape recovery stimulated in cell culture media with isothermal holding at 37° C. could be tested using the immersion fixture of the TA Instruments DMA-800. The results may be compared with predictions from the same characterization on uniaxial test specimens of the same compositions and in light of the unit cell geometries. To determine the effect of unit-cell shape changes on cell shape, microscopy-based analyses of cell location and morphology comparable to the preliminary data may be performed as seen in FIGS. 3 through 6. Based on these results, archetypes will be combined to design 3D scaffolds for testing in tissue engineering.

EXAMPLE 4

Figure 12:
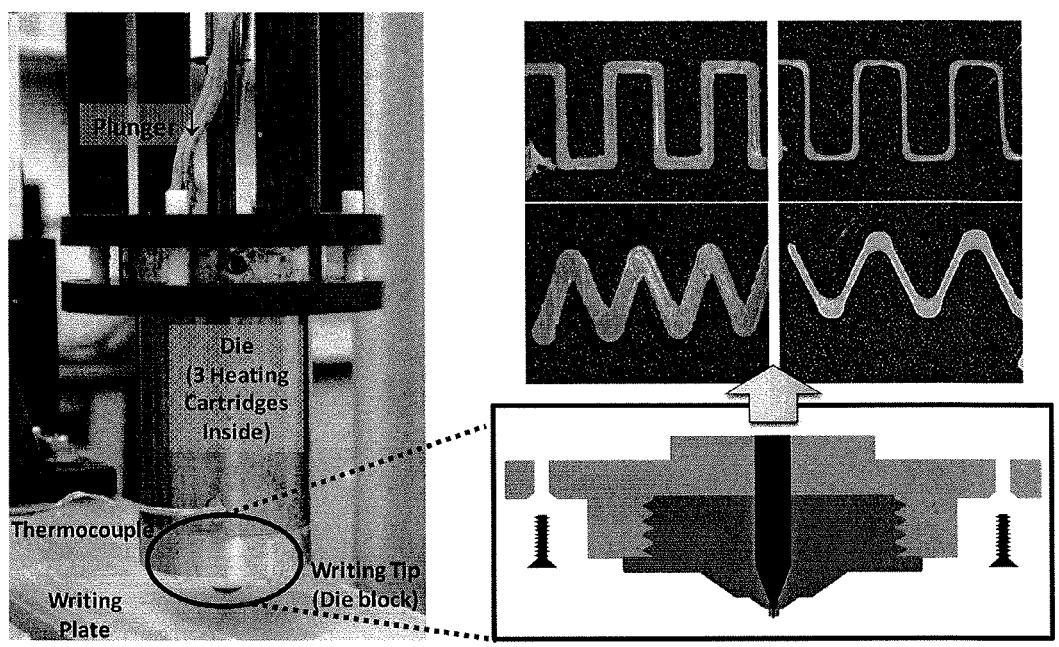
FIG. 12 is a schematic of an apparatus for fabricating scaffolds.
Figure 13:
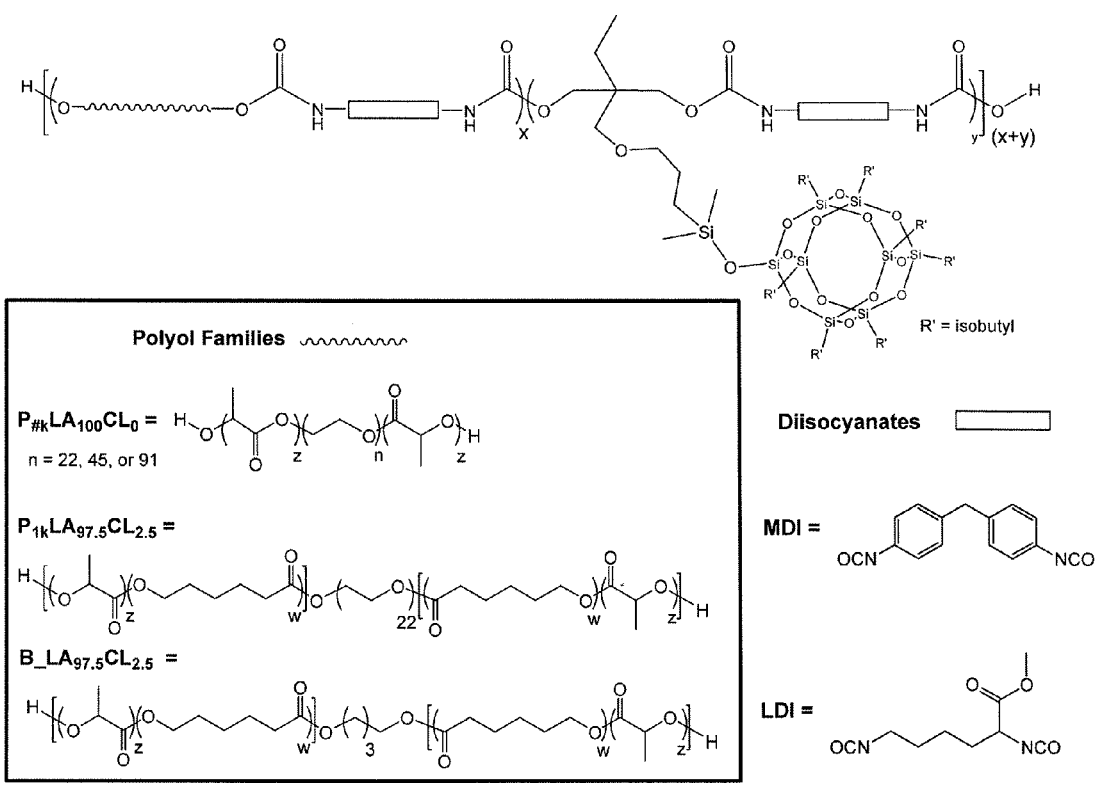
FIG. 13 is a diagram of the general POSS TPU structure and the different polyols and diisocyanates used to create a variety of polyurethane compositions with different properties.

The preferred approach for fabricating scaffolds in high-resolution is fused deposition modeling, a rapid prototyping technique where polymer is deposited in strands using a 3-D positioning system and a heated extrusion nozzle. For this approach, a solid-freeform fabrication device (SFF) capable has been designed and fabricated for extruding small quantities (ca. 1-5 g) of thermoplastic polymers into 2D and 3D structures with minimum feature size of 100 µm, as seen in FIG. 12. The apparatus is shown extruding downward onto a 3-axis substrate that translates under computer control. The inset of FIG. 12 shows the die design and representative structures (image widths=4 mm) deposited from a biodegradable polyurethane. FIG. 12 includes the apparatus design, which consists of a piston extruder with PID temperature control and a carefully designed die to allow delivery of a fine extrudate without over-pressurization. Opposing the extruder die is a substrate that is rigidly mounted to a 3-axis translation system under stepper motor control with high precision and flexible programming. FIG. 8 also shows example serpentine structures prepared using this apparatus. Preliminary observations on expanding and contracting struts of a PDLA-based POSS polyurethane are shown in FIG. 2 with cross-polarizer imaging to reveal stress distribution and relaxation in the growing and contracting scaffold elements.

Using methods described above, temporary shapes (starting point shapes) of the strut-based scaffolds may be fixed using modification of refined methods of shape memory characterization developed previously for tensile specimens. In particular, laminated thermoplastic tabs may be used at opposing ends and of the strut-based scaffolds for facile handling and gripping. Once gripped in a stretching device such as the Linkam TST-350 miniature testing apparatus (under microscope viewing), the samples may be heated to a compliant, elastic state above $T_g$, compressed or extended, and then cooled below $T_g$ for fixing.

EXAMPLE 5

Melt processing of biodegradable expanding or contracting scaffolds requires a thermoplastic shape memory polymer that can be triggered to recover by slight (sharp) heating, by degradation, or by water plasticization. Moreover, the scaffold should not lose its architectural form during shape change (from struts to a film) so that the hard segments (physical crosslinks) should themselves be relatively stable. Given these criteria, biodegradable thermoplastic polyurethanes (TPUs) consisting of amorphous, degradable soft blocks and hard-blocks build from the hydrophobic polyhedral oliogosilisesquioxane (POSS) moiety may be selected. FIG. 12 shows a representative polymer structure. Tailoring of both glass transition temperature, $T_g$, and water-swelling is afforded through variation in the soft segment copolymer composition, featuring comonomers selected from: PEG (hydrophobic initiatior), hexane diol (hydrophobic initiator), ∈-CL, and D,L-Lactide. With this set, $T_g$ ranging from −1 to 45° C. and degradation rate ranging from rapid to suppressed may be demonstrated. For further testing, selection of compositions with $T_g$ and hydrophilicity such that with plasticization kinetics will drive shape recovery on the time scale of several days to weeks is preferred.

EXAMPLE 6

Figure 14:
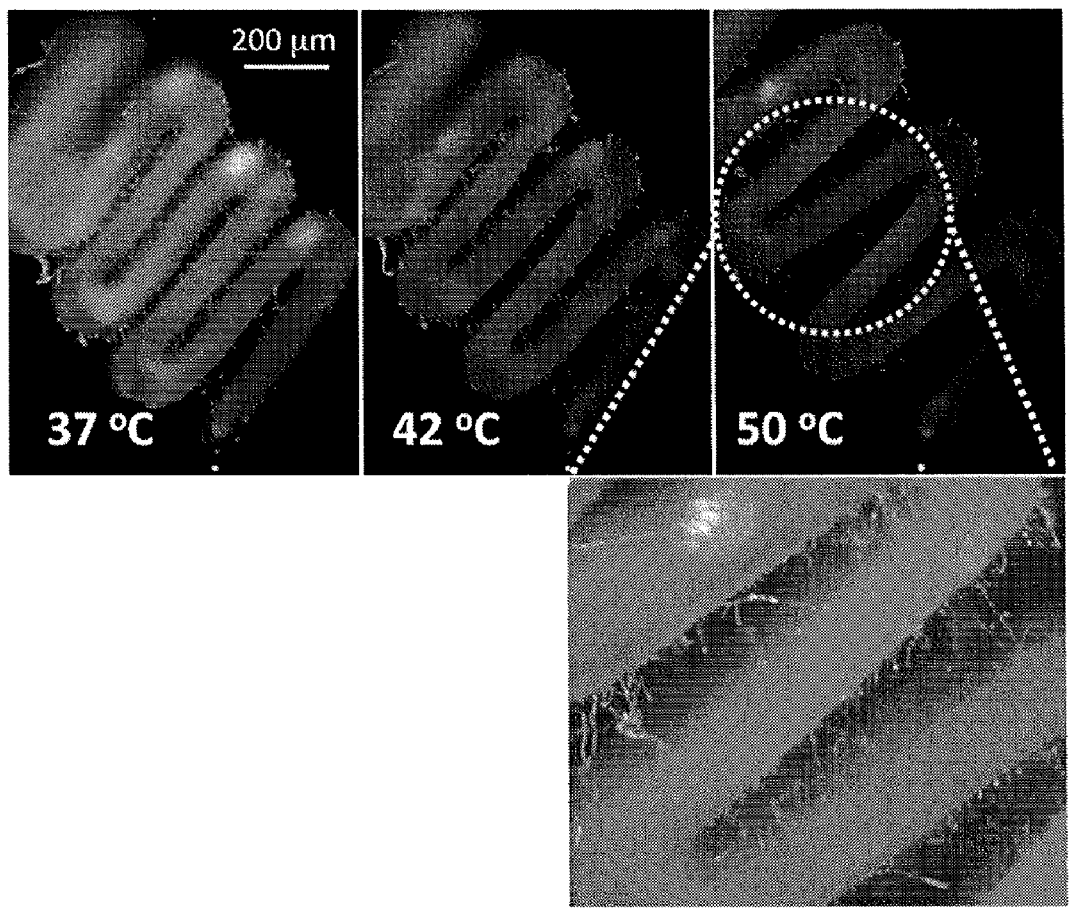
FIG. 14 is a series of images of a combined scaffold of shape memory struts and electrospun web.

Although preliminary data (see FIGS. 3-6) strongly suggest that cell seeding of SFF scaffolds can produce a range of cell material interactions, from the direct attachment of single cells to the generation of cell condensations around and between scaffold struts, electrospinning of sub-micron poly (∈-caprolactone) fibers directly onto direct-written scaffolds using an apparatus developed in the Mather lab for the construction of novel membranes may also prove to be useful. This apparatus involves controlled pumping of a dilute polymer solution via syringe pump to a needle held at high electrical potential relative to a grounded rotating drum. Preliminary experiments seen in FIG. 14 have shown that this process works well if the SFF-written scaffold is first coated with a mist of high dielectric constant solvent, including water or DMF, via electrospraying.

In addition, photocured, end-linked networks with biodegradable network chains may be used. These materials may be used to develop shape memory foams that allow uniform and controlled dynamic contraction and to test these foam scaffolds in an established cartilage tissue-engineering protocol to determine the extent to which dynamic contraction of the foam affects cell phenotype. The approach is to prepare foams from end-linked PCL-PEO co-networks using salt leaching and freeze-drying. The resulting SMP scaffolds may be tested in an established cartilage tissue-engineering protocol and the extent to which dynamic changes in scaffold shape affect cell phenotype will be determined by biochemical and biomechanical comparison to static control scaffolds.

EXAMPLE 7

Figure 15:
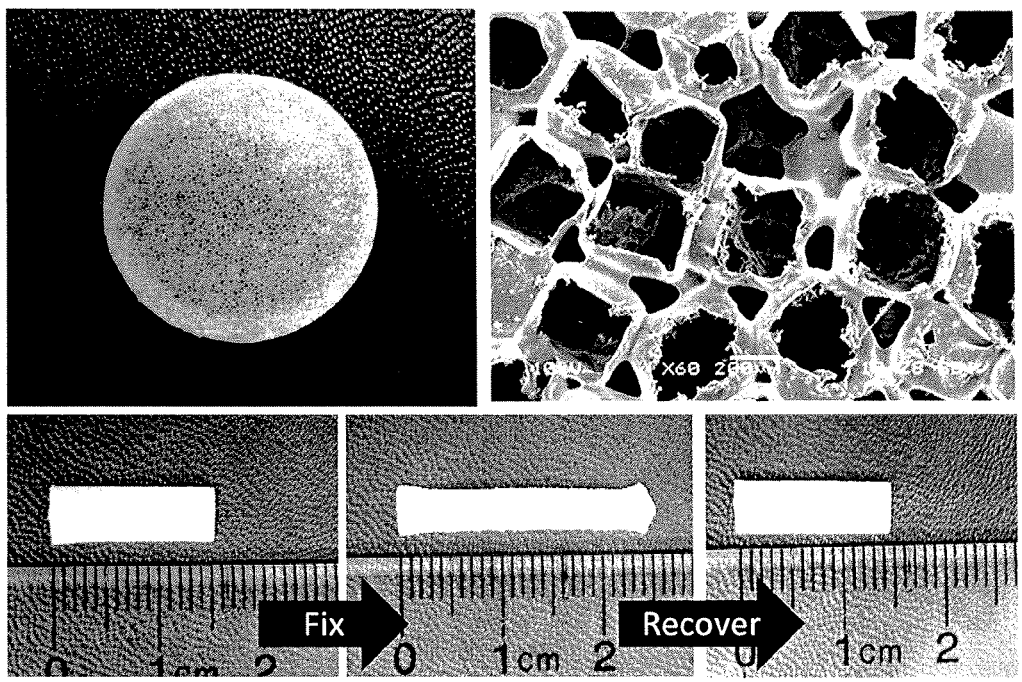
FIG. 15 is a series of images of SMP Foam prepared from end-linked poly(∈-caprolactone) using salt leaching.
Figure 16:
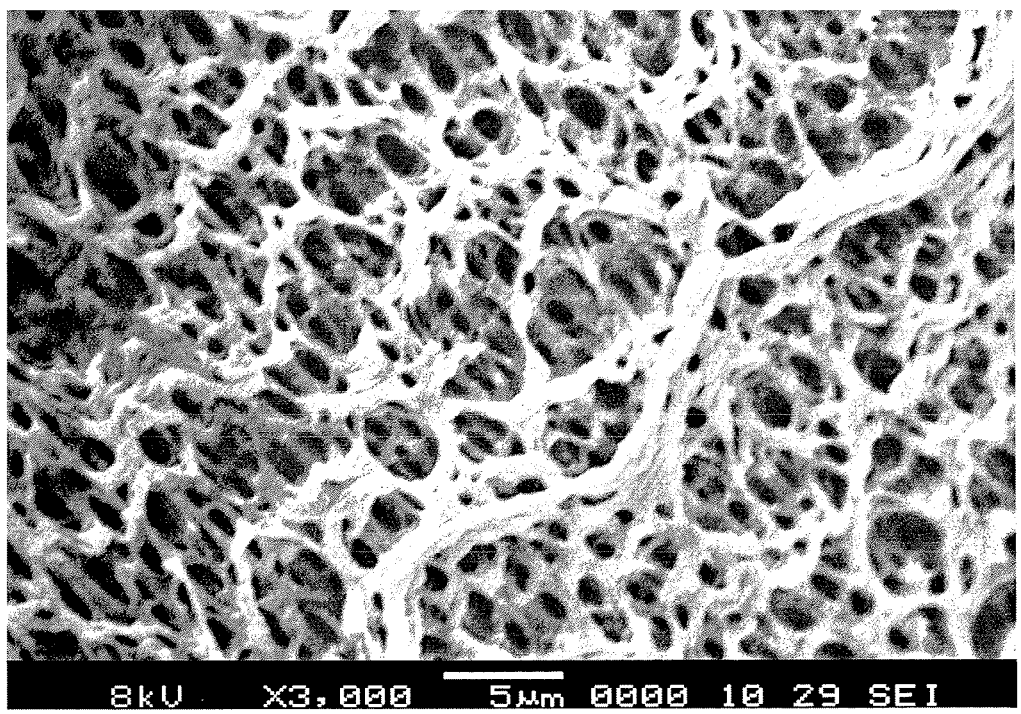
FIG. 16 is an image of PEO-PCL co-network foam following swelling to equilibrium and then freeze-drying.
Figure 17B:
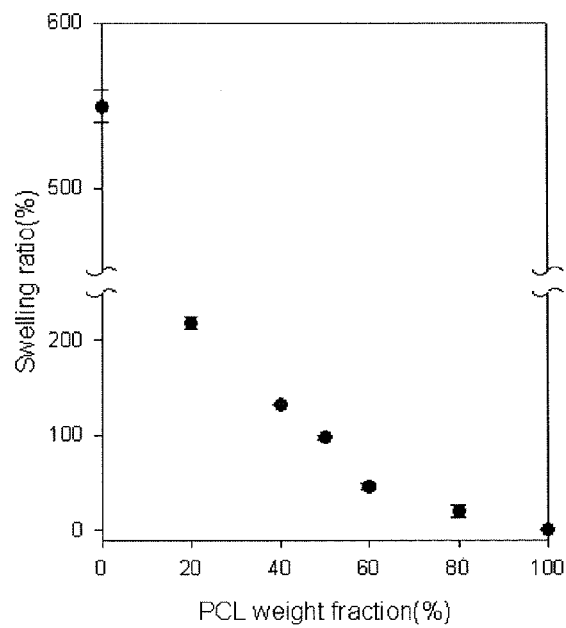

Highly porous shape memory polymer foams whose structure is determined by the processing parameters, including salt particle mean size for the salt-leaching method or solvent crystallization temperature for the freeze-drying method may also be used. These two designs yield scaffolds of varying porosity, pore size, and equilibrium shape, as described in detail below. Foams from the end-linked PCL-PEO co-networks described below have been prepared using two methods: salt leaching and freeze-drying. Preliminary studies with salt leaching proved highly successful at yielding end-linked PCL networks with 10% polymer density and quite complete shape memory, as shown in FIG. 15. As a second method, end-linked networks may be swelled with water, dioxane, or dimethylsulfoxide (DMSO) and subsequently freeze-drying the samples to yield highly porous foams, as seen in FIG. 16. Heating or hydrating such covalently crosslinked foams is expected to stimulate contraction to the dense state and, in doing so, impart compressive stress upon adherent cells cultured within the scaffold pores. Preliminary results for a sample, swollen to equilibrium in water, frozen at T=−80° C., and then sublimed are shown in the FIG. 17. An attractive porous structure appears beneath a skin of dense polymer.

Methods for fixing of temporary shapes for the two shape memory scaffolds are distinct for the two cases. Salt-leached SMP foams are fixed following methods described earlier for the strut-based scaffolds. Freeze-dried SMP foams are fixed in a temporary shape at the time of the solvent sublimation in the freeze dryer.

As discussed above, the present invention encompasses two types of shape memory polymer foam for use in active cell culture, one featuring the equilibrium shape as expanded and the other featuring the equilibrium shape as condensed. Each of these equilibrium states determine the shape toward which the scaffold will evolve with time during water plasticization, polymer degradation, slight heating, or some combination of the three. A single polymer family that enable these two types of scaffolds achieved through distinct processing methodology has been envisioned, as is now described. End-linked co-networks consisting of poly(ethylene oxide) and poly(∈-caprolactone) diene chains linked together into a well-defined covalent network through photo-initiated addition of the vinyl termini with a multifunctional thiol crosslinker have been designed for this approach. A schematic for this polymer chemistry is shown in FIG. 17A.

The comparatively simpler system of the present invention offers outstanding property tailoring, including controlled variation of: (i) swelling in water, (ii) hydrophobicity, (iii) degradation rate, and (iv) elastic modulus. To encourage and modulate cell adhesion and proliferation on such scaffolds, a dangling RGD-bearing network chain was designed. This molecule is synthesized in two steps from commercially available PEG and GRGDS peptide (SEQ ID NO: 1). Shown along with the schematic of the network synthesis is water-swelling data as a function of composition. Significant shape fixing and recovery of compositions featuring at least 40% PCL has been observed, suggesting that the hydrated state consists of two interpenetrating phases, with the PCL phase enabling shape fixing and recovery through network chain crystallization and melting, respectively. As described above, foams of such materials that can serve as scaffolds are formed by salt leaching (equilibrium shape =foamed) and freeze drying (equilibrium shape =dense).

EXAMPLE 8

Hydro gels

There is a continued need for a biodegradable and biocompatible hydrogel scaffold with tailored shape memory effect and good bioactivity as well as desirable mechanical properties for soft-tissue application. To this end, elastic, biodegradable aliphatic polyester poly(∈-caprolactone) (PCL) macromers were co-photocured with monoacrylated Gly-Arg-Gly-Asp-Ser (GRGDS) peptide sequences with PEG spacer arms to prepare a composite PCL/PEG-GRGDS hydrogel. The hydrogel, therefore, had a structure with PEG-GRGDS chains dangling on a PCL network. It is likely that: (i) PCL fraction in the co-network could provide a good shape memory property and appropriate mechanical property; (ii) PEG-GRGDS dangling chains could enhance cell biospecific binding affinity and control cell spatial organization ability on the hydrogel; and (iii) the architecture of the hydrogel allows for modification of the hydrophilic/hydrophobic balance and mechanical property of the scaffold by varying the weight ratios of PCL macromer to PEG-GRGDS monomer in order to fit the requirements of various soft tissue repairs. It is also assumed that the shape memory effect of the hydrogel can guide cell behavior on the scaffold to develop specific, biological soft tissue substitutes. As an example, FIG. 18 shows a simple mechanism using smart bioactive hydrogel to dynamically control cell-material interactions during cell culture in vitro. A bulk PCL/PEG-GRGDS hydrogel film is processed into a square ($L_0 \times L_0$), the original permanent shape. The square hydrogel film is then deformed into a rectangle film ($L_1 \times L_2$) by heating above its $T_{trans}$ and cooling under constrained to set the material into its temporary shape. Cells are seeded and cultured on the rectangle film at room temperature, below its $T_{trans}$. The cell adhesion-specific peptides tethered on the film provide signaling domains to modulate cell attachment, proliferation and migration. Ideally, $T_{trans}$ of the material between room and body temperature results in an automatically induced shape change after the material is heated to 37° C. Therefore, once the cell-attached film is heated to 37° C., cells can sense the mechanical cues and be guided to align themselves in response to the recovery of the materials from its temporary shape (the rectangle film) to its permanent shape (the square film) at body temperature. The swelling, thermal characterization, mechanical property, and one- and two-way shape memory effects of the hydrogel were examined. The behavior of fibroblasts on the smart bioactive hydrogel was also investigated to illustrate the potential of the shape memory thermoplastics in biomedical applications.

As the following Examples show, a set of cross-linked PCL3k/PEG2k-GRGDS hydro gels was successfully prepared by variation in the weight ratios of both PCL3k diacrylates and acrylate-PEG2k-GRGDS monomers as two precursors in the polymer network synthesis. The resulting hydrogel has a structure with covalent immobilization of GRGDS peptide sequences to the PCL3k network via flexible PEG2k spacer chains. It was found that the gel fraction, swelling, and storage modulus at 25° C. of the hydro gels were significantly affected by the composition of the hydro gels. Both gel fraction and storage modulus at 25° C. decreased with increasing weight percent of PEG2k-GRGDS in the hydro gels, while the swelling of the hydro gels increased. DSC results showed that the transition temperature, $T_m$, of PCL3k/PEG2k-GRGDS hydrogel was in the range of 39.2° C. to 43.2° C., which is above body temperature and enables on demand control of the shape change by supplemental heating. To achieve the automatic induction of the shape change at body temperature, PCL2k/PEG2k-GRGDS (85/15) hydrogel with a relatively low $T_m$ at 31.8° C., which is between room and body temperature, was prepared. The isothermal strain recovery of the stretched PCL2k/PEG2k-GRGDS (85/15) hydrogel film at body temperature occurred pretty fast, which was about 75.1% in only 15 min. Analysis of shape memory properties with DMA revealed that all PCL3k/PEG2k-GRGDS hydro gels and PCL2k/PEG2k-GRGDS (85/15) hydrogel not only had excellent, reproducible 1W-SM effect, but also novel 2W-SM effect which allows reversible shape changes through cooling/heating cycles under an applied single force. Both shape fixing and recovery of the hydro gels were about 99% in the light of their one-way SM cycles. In addition, the cell attachment and proliferation studies revealed that the presentation of GRGDS molecules in the hydro gels via flexible PEG spacers facilitated fibroblasts adhesion, spreading and growth on the hydrogel surface.

Dynamic cell culture study showed that fibroblasts aligned approximately perpendicular to the sample stretched direction in response to the strain recovery of the stretched PCL2k/PEG2k-GRGDS (85/15) hydrogel film, whereas the cells cultured on the un-stretched PCL2k/PEG2k-GRGDS (85/15) hydrogel film displayed random orientation. When fibroblasts were cultured on the stretched PCL3k/PEG2k-GRGDS (85/15) hydrogel film that having a relatively high $T_m$ at about 43.2° C., the cells proximately aligned parallel to the sample stretched direction.

Accordingly, tuning the transition temperature of PCL2k/PEG2k-GRGDS (85/15) hydrogel between room and body temperature leads to the automatic shape change from its deformed state at body temperature, thus to control cells orientation and cell-material interactions during cell culture. The multifunctional hydrogel presented here combined good bioactivity and biodegradability with the excellent shape-memory property that is expected to be useful for tissue engineering, especially as biomedical implants or for guiding cells by the incorporations of both bioactive signal domains and shape-memory effects to developing artificial tissues and organs with appropriate functionality.

EXAMPLE 9

Materials and Methods

Hydroxyl end functionalized Poly($\in$-caprolactone) diols ("PCL diols") [α, ω-dihydroxy poly($\in$-caprolactone)] with average molecular weights of 3,000 g/mol and 2,000 g/mol, respectively, were purchased from Scientific Polymer Products, Inc; the diols had the following formulae: H-[O(CH$_2$)$_5$CO-]$_n$O(CH$_2$CH$_2$O)$_3$-[CO(CH$_2$)$_5$O-]$_m$OH. Prior to use, the PCL diols were completely dried in a vacuum oven at room temperature. Acryloyl chloride (98% purity), triethylamine (>99%), 2,2-dimethoxy-2-phenyl acetophenone (DMPA) (99%), pentaerythritol tetrakis (3-mercaptopropionate) (hereafter, "tetrathiol") (97%) were purchased from Sigma-Aldrich® and used as received. Toluene was obtained from Fisher Scientific® and distilled over calcium hydride (90-95%, Sigma-Aldrich) before use.

Acrylate PEG-N-hydroxysuccinimide (acrylate-PEG-NHS, Mw 2000 Da) was obtained from JenKem Technology USA Inc, the H-Gly-Arg-Gly-Asp-Ser-OH (GRGDS) peptide from Baychem® California, and MPEG-acrylate (Mw 2000 Da) from Creative PEGWorks, and used without further purification. Reagents for cell culture were all purchased from Invitrogen®. All other chemicals used were of reagent grade and were used without further purification.

Synthesis of the PCL3k macromer and acrylate-PEG2k-GRGDS monomer are schematically illustrated in FIGS. 19A and 19B. The synthesis of PCL3k macromer was carried out by the reaction of acryloyl chloride with the terminal hydroxyl groups of PCL3k diol in the presence of triethylamine in anhydrous toluene according to the method as described in the literatures. Specifically, 10 g (3.3 mM) of the PCL3k diol was dissolved in 60 ml of anhydrous toluene in a previous flamed-dried three-neck flask under a nitrogen atmosphere. While stifling, two and a half times excess (relative to PCL3k diol mole) of triethylamine (1.18 ml) and acryloyl chloride (0.69 ml) were successively added dropwise by syringe to the flask at room temperature. The reaction was then carried out at 90° C. for 4 h. Following the synthesis, the reaction mixture was filtered to remove the resulting triethylamine-hydrochloride, precipitated in a 50:1 excess of cold n-hexanes, and then vacuum dried at room temperature for about 48 h. The percent yield from the collected product averaged 90%. The degree of substitution of acrylate groups was determined by $^1$H-NMR and found to range from 87% to 95%.

GRGDS was conjugated to PEG monoacrylate by reacting the peptide with acrylate-PEG2k-NHS at a 1:1 molar ratio in 50 mM sodium bicarbonate (pH 8.5). The peptide and acrylate-PEG2k-NHS were dissolved separately in the biocarbonate buffer. Then the latter solution was added dropwise to the former solution while stifling, and reacted at room temperature for about 12 h. The reaction mixture was dialyzed using a dialysis membrane (MWCO 500~1000 Da, Spectrum Laboratories, Inc.) in deionized distilled water for 48 h, lyophilized and stored at −20° C. before use. The product was denoted as acrylate-PEG2k-GRGDS.

The chemically crosslinked PCL3k/PEG2k-GRGDS co-network with both hydrophilic and hydrophobic components was prepared via free radical photopolymeric reaction of the PCL3k macromer and acrylate-PEG2k-GRGDS monomer with different weight ratios. The procedure of the co-network synthesis is illustrated in FIG. 20. First, 170 mg of PCL3k diacrylates and 30 mg of acrylate-PEG2k-GRGDS were dissolved into 100 µl dichloromethane (DCM) and 1 ml dimethyl sulfoxide (DMSO), respectively. Next, both solutions were mixed, and then 0.040 mmol of tetrathiol crosslinker (1:1 molar ratio of thiol to double bond functionality) and 2 wt. % (with respect to the total weight of both reaction precursors) of photoinitiator, DMPA, were added. The clear mixture was then filled into a mold formed by two glass slides and a teflon spacer of 0.83 mm thickness, irradiated with UV light (1200 µW/cm$^2$) at a wavelength of 365 nm, with a lamp-sample distance of 15 cm at room temperature for 1 hour, and dried successively in a fume hood overnight and in a vacuum oven at 70° C. for 48 h to allow the solvent to remove completely. The weight of the isolated film was determined (W$_1$). This co-network sample is referred to as PCL3k/PEG2k-GRGDS (85/15) co-network. According to the various weight ratios of the PCL3k macromer and acrylate-PEG2k-GRGDS monomer as UV-curing, other GRGDS-containing co-network samples used in this study also include PCL3k/PEG2k-GRGDS (70/30) and PCL3k/PEG2k-GRGDS (60/40) co-network.

The controls, PCL3k/MPEG2k co-networks, were prepared by UV-curing the mixture of PCL3k diacrylates/DCM and MPEG2k monoacrylate/DMSO in the presence of tetrathiol and DMPA. The preparation procedure was identical with that of PCL3k/PEG2k-GRGDS co-network described above. In the same way, those control samples were denoted as PCL3k/MPEG2k (85/15), PCL3k/MPEG2k (70/30), and PCL3k/MPEG2k (60/40) co-network, according to the different weight ratios of PCL3k macromer and acrylate-MPEG2k monomer.

To determine the quality of cross linking, gel fraction values of PCL3k/PEG2k-GRGDS and PCL3k/MPEG2k co-networks were measured using extraction and gravimetry. Specifically, a PCL3k/PEG2k-GRGDS or PCL3k/MPEG2k film was extracted repeatedly in DCM at 37° C. for 24 h, and dried under vacuum at 70° C. for 48 h. The dry film was weighted again (W$_2$) and the gel fraction value (G %) was calculated according to the following equation:

$$G(\%) = W_2/W_1 \times 100\%. \qquad \text{Equation (1)}$$

Subsequent to extraction, the film was allowed to equilibrate in deionized distilled water for 24 h and weighed (W$_3$) after excess water had been carefully swabbed away. All measurements were performed in triplicates and averaged. The total water uptake (W$_c$%) of PCL3k/PEG2k-GRGDS and PCL3k/MPEG2k hydrogel was calculated by the following equation:

$$W_c(\%) = (W_3 - W_2)/W_2 \times 100\%. \qquad \text{Equation (2)}$$

Thermal properties of both dry and swollen PCL3k/PEG2k-GRGDS and PCL3k/MPEG2k samples were characterized using differential scanning calorimetry (DSC, TA Instruments, Inc., Model Q100) at a heating and cooling rate of 10° C./min from −80° C. to 100° C. under a N$_2$ atmosphere. The presented melting temperatures (T$_m$) and latent heats of fusion (ΔH$_m$) of the samples were taken from the second heating traces.

The crystalline states of PCL3k/PEG2k-GRGDS and PCL3k/MPEG2k co-networks were identified and compared by wide angle X-ray diffraction (WAXD). A Rigaku S-Max 3000 with a Cu Kα source (λ=1.54 Å) was used to expose each sample for 30 min at ambient temperature. The samples were scanned at diffraction angles (2θ) between 5° and 40° with a scanning rate of 0.5°/min at 45 kV and 0.88 mA. The distance between the samples and Fujifilm was 150 mm. X-ray diffraction patterns were recorded on a Fuji image plate measuring 10 cm×15 cm and processed with a digital reader (Fuji, FLA 7000) to yield pixels of dimension 25 μm². Low temperature WAXD study was achieved by cooling the whole sample chamber in the range of 0° C. to 5° C. without vacuum.

Linear viscoelastic thermo-mechanical properties of PCL3k/PEG2k-GRGDS and PCL3k/MPEG2k co-networks were determined using dynamic mechanical analysis ("DMA"). A TA Instruments Q800 apparatus was employed in a tensile mode with a preload force of 10 mN, an oscillation amplitude of 15 μm, static/dynamic stress amplitude ratio ("force tracking") of 110%, and an oscillation frequency of 1 Hz. Samples were cut from the cured, extracted networks to feature dimensions of 4 mm (length)×1.4 mm (width)×0.70 mm (thickness). After loading each film specimen at room temperature under tensile stress, they were heated up to 80° C. to erase all thermal history, then cooled down to −120° C. at 3° C./min. Once thermally equilibrated, the samples were ramped again up to 120° C. at 3° C./min. The second heating traces were recorded and adapted to determine modulus values.

One-way shape memory (1W-SM) behavior of PCL3k/PEG2k-GRGDS co-networks was characterized by DMA using a four-step program that begins at an elevated temperature ($T>T_m$): (1) Deformation: A sample was elongated by increasing the applied load at a rate of 0.05 N/min at 70° C.; (2) Fixing: the sample was then cooled at 2° C./min to 0° C. (below $T_m$) under a constant load to fix the temporary shape; (3) Unloading: the load was removed to 0.001 N at a constant rate of 0.2 N/min; and (4) Recovery: the sample was finally recovered by being heated to the original deformation temperature 70° C. at a rate of 2° C./min. The shape fixing $R_f$ and the strain recovery $R_r$ are the measures to quantify the fixation of the temporary shape and the recovery of the permanent shape of the polymer networks, respectively. They are calculated from the following equations:

$$R_f(\%) = \epsilon_\mu / \epsilon_i \times 100 \qquad \text{Equation (3)}$$

$$R_r(\%) = (\epsilon_\mu - \epsilon_p)/(\epsilon_i - \epsilon_p) \times 100 \qquad \text{Equation (4)}$$

where $\epsilon_\mu$ is the strain obtained after unloading, $\epsilon_i$ is the temporal strain before the load was released, and $\epsilon_p$ is the permanent strain after heat-induced recovery. Here, $R_f$ and $R_r$ were presented in base of the second shape-memory cycle.

In contrast, the two-way shape memory (2W-SM) cycles were conducted with the following three steps, the only difference being the lack of an unloading step prior to re-heating: (1) Deformation: after equilibrated at 70° C. for 1 min, the sample was elongated by increasing the applied load at 0.05 N/min; (2) Cooling: the deformed sample was then cooled down to 0° C. at a rate of 2° C./min; and (3) Heating: after being held for 10 min at 0° C., the sample was then heated up to 70° C. at the same rate as of cooling. This thermo-mechanical protocol was performed repeatedly by cooling and heating under a constant applied tensile stress. Characteristics of the 2W-SM behavior included the actuation magnitude, $R_{act}(\sigma)$ and the strain recovery magnitude, $R_{rec}(\sigma)$. $R_{act}(\sigma)$ is the strain increment during actuation, expressed as a percentage of the baseline strain at $T>T_m$. These characteristics were calculated from the observable sample lengths for a 2W-SM behavior by the following equations (3) and (4):

$$R_{act}(\sigma) = \frac{L_{low}(\sigma) - L_{high}(\sigma)}{L_o} \times 100\% \qquad \text{Equation (5)}$$

$$R_{rec}(\sigma) = \frac{L_{low} - L_{high}^{final}}{L_{low} - L_{high}^{initial}} \times 100\% \qquad \text{Equation (6)}$$

For equation (5), $L_{high}$ is the length of the sample at high temperature ($T>T_m$) and $L_{low}$ is the length at low temperature ($T<T_m$), both with stress, σ, applied. For equation (6), $L_{high}^{initial}$ is the original length under stress and at a high temperature, while $L_{high}^{final}$ is the final length under stress after reheating to induce recovery.

For sample preparation and sterilization for cell culture, circular disks which were 6.4 mm in diameter were punched from the fully swollen PCL3k/PEG2k-GRGDS hydrogel film for cell attachment study. These circular films could exactly fit the wells of the 96-well tissue culture plate to avoid the cells suspension going down to the culture plates instead of being seeded onto the films. The samples were sterilized by 70% ethanol solution (v/v) for at least 24 h, re-swollen in sterile PBS for 2 days while changing the PBS twice per day, and further sterilized using UV irradiation on the cell seeding side for 30 min before seeded with cells.

The mouse fibroblast C3H/10T1/2 cell line was purchased from American Type Culture Collection (ATCC Cell Lines, Rockville, USA) and were cultured in basal medium eagle (BME) supplemented with 10% FBS, 100 U/mL penicillin, and 100 μg/mL streptomycin. These cells were maintained under standard culture condition (37° C., 95% relative humidity and 5% $CO_2$) until cells reach 60-70% confluency. Cells were harvested by being incubated in 0.25% trypsin/EDTA for 5 min. After incubation, an equal volume of cell culture medium was added to neutralize the trypsin. The cells were centrifuged, collected and re-suspended in 5 mL of cell culture medium. 20 μL of the cells suspension was used for cell counting using hemacytometer. Cells of passages 13-17 were used for seeding experiments. For the current experiments, the cells were knowingly used beyond the recommended passage limit (passage 15) since the impact on morphology was expected to be negligible.

For the cell attachment experiments, the sterilized circular hydrogel films with and without peptide modification, as well as pure PCL3k network films, were placed in 96-well plates. Three plates were used for three different incubation periods of 3, 6 and 12 h. The wells in each plate were divided into groups for corresponding samples: (1) positive control group (repeating 3 wells): only test cells were added; (2) GRGDS-containing hydrogel group: composed of three sub-groups, PCL3k/PEG2k-GRGDS (85/15), PCL3k/PEG2k-GRGDS (70/30) and PCL2k/PEG2k-GRGDS (85/15) hydrogel films, repeating 3 wells for each group; and (3) negative control group: further divided into three sub-groups (3 wells for each group), corresponding to pure PCL3k network film, PCL3k/MPEG2k (85/15) and PCL3k/MPEG2k (70/30) hydrogel film in each well.

The fibroblasts suspension was seeded on the top of each sample at a density of $3.1 \times 10^4$ cells/cm². Cell cultures were maintained under standard culture conditions for different specific times. At each time point, the cells on the sample surface were rinsed with PBS twice to remove non-adherent cells and lifted using 50 μL/well of 0.25% trypsin/EDTA solution. Then, the number of fibroblasts attached to the films was counted using hemacytometer. Total cell number at each time point was divided by the number of initially seeded cells to normalize the cell attachment data. The experiment was performed 5 times for n=5 independent comparison.

The long-time cell attachment study was carried out for three continuous days by observing the cell morphology and viability at different time points. Specifically, the aforementioned, sterilized samples, pure PCL3k network film, PCL3k/MPEG2k (85/15), PCL3k/MPEG2k (70/30), PCL3k/PEG2k-GRGDS (85/15), PCL3k/PEG2k-GRGDS (70/30) and PCL2k/PEG2k-GRGDS (85/15) hydrogel film, were placed in a 96-well plate. Then fibroblasts were seeded at a density of $1.2 \times 10^4$ cells/cm$^2$ on the top of each sample and cultured under the standard culture condition for 24, 48 and 72 h. The cells seeded on the TCPS plate were positive controls. Each plate was used for a specific time. After incubation for a predetermined time, the plate was withdrawn from incubator, removed medium, washed twice with fresh PBS to remove floating dead cells or non-adherent cells, and then added with the fresh LIVE/DEAD® reagent solution. The plate covered by aluminum foil was put back to the incubator for further incubation for 30 min. The cell morphology and viability were observed under the fluorescence microscopes (Leica DMI 4000). Green and red fluorescence indicate viable and dead cells, respectively.

The preparation of PCL2k/PEG2k-GRGDS (85/15) co-network used the same procedure as that of PCL3k/PEG2k-GRGDS (85/15) co-network described above. Specifically, 100 mg of PCL2k diacrylates and 17.6 mg of acrylate-PEG2k-GRGDS were dissolved into 100 dichloromethane (DCM) and 1 ml dimethyl sulfoxide (DMSO), respectively. Then the two solutions were mixed and UV-cured in the presence of DMPA (2 wt. %, with respect to the total weight of the both precursors) and tetrathoil (1:1 molar ratio of thiol to double bonds) for 1 hour. The resulting PCL2k/PEG2k-GRGDS (85/15) co-network was dried first in the hood at room temperature for 12 h, extracted by DCM for 24 h, and then fully dried at 60° C. in vacuum oven.

A rectangle PCL2k/PEG2k-GRGDS (85/15) hydrogel film with a typical dimension of 4.28 mm (length)×1.73 mm (width)×0.31 mm (thickness) was stretched to 50% elongation from the original shape at 50° C. (T>$T_m$) by increasing the applied load at 0.05 N/min. The stretched film was then cooled to −10° C. (T<$T_m$) and isothermally annealed for 5 min under loading to fix the temporary shape. After being sterilized by 70% ethanol solution (v/v), the stretched film with fixed temporary shape was immersed in sterile PBS at room temperature for 2 days to allow the sample to be fully swollen. Following further sterilization by UV irradiation on the cell seeding side for 30 min, the stretched sample was seeded with cells (cell density was $1.0 \times 10^4$ cells/cm$^2$) at room temperature, incubated at 28° C. for 5 h to allow for cells adhesion, and then further cultured at 37° C. for another 5 h. The shape-memory effect was then activated at 37° C., resulting in the restoration of the original size to some extent. Cell behavior on the converted film was analyzed by live/dead staining as described above.

To quantify the cell orientation angles, the cells (the original cell seeding density was $0.45 \times 10^4$ cells/cm$^2$) were stained using CellMask™ plasma membrane stain (Invitrogen) to obtain an accurate representation of the cell outline. Specifically, after the cells were stained using 2.5 µg/mL of CellMask™ plasma membrane stain in DPBS (Invitrogen) at 37° C. for 5 min, the cells were sequentially rinsed with DPBS three times, and then immediately imaged using the fluorescence microscope mentioned above. Images of the stained cells were converted to binary images using Image J software and were fit as ellipses. An α angle was automatically measured by Image J. Thus, the cell orientation angle was calculated as the angle between the cc angle and the direction of the reference line, which was drawn on the sample using a razor blade to indicate the direction that the sample had been stretched. The cells were considered to be aligned perpendicular to the reference line (the stretching direction) when this angle was between 80 and 90°. When the cell orientation angle was less than 10°, cells were considered aligned parallel to the reference line. The orientation angles of the cells on the converted film were analyzed by randomly selecting 50 cells.

The shape recovery of the stretched PCL2k/PEG2k-GRGDS (85/15) hydrogel film at 25, 28 and 37° C. was determined without cells seeding by measuring the lengths of the sample before and after incubation in PBS at each given temperature for 5 h. The shape recovery of the hydrogel film was calculated using $R_r$ (%)=$(L_1-L)/(L_1-L_0) \times 100\%$, where L was the length of the recovered (shrunken) shape at given temperature. $L_1$ and $L_0$ were the lengths of the temporary shape and the original shape before recovery, respectively.

The cell attachment results were reported as means±standard deviation. Both one-way analysis of variance (ANOVA) and p-test were used to determine the significant differences among the groups with a 95% confidence interval (α=0.05). A p value less than 0.05 was considered to be significant.

EXAMPLE 10

Preparation of PCL3k/PEG2k-GRGDS Co-Networks

Recently, the combination of shape memory capability of PCL with its biodegradable property has brought up great potential that is capable of opening up important applications for shape memory polymers in implantable biomedical areas. In particular, PCL has been extensively researched as a shape memory polymer for a (meth)acrylate-based thermoset or a polyurethane segment-based thermoplastic. Herein, novel PCL3k macromer was synthesized in order to develop chemically crosslinked PCL3k networks with structural and mechanical homogeneity. The reaction of PCL3k diol with acryloyl chloride led to the formation of PCL3k macromer (PCL3k diacrylates) that are vinyl group-end capped, which was verified by the presence of the vinyl groups in the δ=5.81-6.44 ppm range through $^1$H-NMR spectrum (data not shown). The functionalization of acrylated PEG2k monomer with peptides was also confirmed using $^1$H-NMR spectrum by the disappearance of proton peak of N-hydroxy succinimidyl ester at 2.83 ppm observed after the coupling reaction (data not shown).

The end acrylic groups of both PCL3k macromer and acrylated PEG2k-GRGDS monomer were introduced to ultimately allow for a straightforward reaction with thiol groups through thiol-ene photochemistry in the presence of DMPA, as shown in FIG. 20. Since PCL3k macromer has two terminal double bonds per molecule, the thiol-acrylate photopolymerization between PCL3k macromer and tetrathiol leads to the formation of 3D PCL3k network with tetrathiol as the netpoints. PEG2k-GRGDS, as a pendant group, is also linked with one chain end to tretrathiol, thus the PCL3k/PEG2k-GRGDS co-network has a structure with PEG2k-GRGDS chains dangling on the 3D PCL3k network. In addition, the produced flexible thioether linkages could improve both strain/stress and shape memory property of the network materials.

EXAMPLE 11

Degree of Gel Fraction and Swelling

Both the gel fraction and equilibrium water uptake of PCL3k/PEG2k-GRGDS hydro gels are shown in the graph in FIG. 21, where gel fraction is represented by open circles, the water uptake ratio is represented by solid circles, the PCL3k/PEG2k-GRGDS co-networks is represented by a red line and PCL3k/MPEG2kco-networks is represented by a black line. The data in FIG. 21 is presented as mean±standard deviation for n=3. The gel fraction decreased as the weight percent of PEG2k-GRGDS increased, whereas the water uptake increased. For example, the gel fraction of PCL3k/PEG2k-GRGDS (70/30) (92.4±1.5%) was lower than that of both PCL3k/PEG2k-GRGDS (85/15) (96.1±1.1%) and pure PCL3k network (99.2±0.2%), however, the extent of water uptake of the corresponding samples were 26.7±1.7%, 10.1±1.0% and 0.2±0.4%, respectively. PCL3k/PEG2k-GRGDS (60/40), which included equal molar amount of PCL3k and PEG2k-GRGDS molecules, had the lowest gel fraction and the highest extent of water uptake; they were 65.3±1.8% and 46.7±2.6%, correspondingly. Further increasing the weight percent of PEG2k-GRGDS dangling chains in the PCL3k/PEG2k-GRGDS system over 50% resulted in the failure of the formation of PCL3k/PEG2k-GRGDS co-network. Compared with the corresponding PCL3k/MPEG2k control samples, the incorporated peptide in PCL3k/PEG2k-GRGDS hydro gels did not significantly affect the gel fraction and the water uptake of the prepared hydro gels, whereas a slightly enhanced water uptake ratio was observed for PCL3k/PEG2k-GRGDS (60/40) hydrogel as compared with PCL3k/MPEG2k (60/40) hydrogel (46.7±2.6% vs. 41.2±1.9%). The increasing swelling ratio may attribute to the existence of GRGDS molecules, which increased the hydrophilicity of the PCL3k/PEG2k-GRGDS (60/40) hydrogel.

EXAMPLE 12

Thermal Characterization and WAXD

FIG. 22 displays the DSC thermogram curves of each of PCL3k/PEG2k-GRGDS co-network, pure PCL3k network, and as-synthesized PEG2k-GRGDS powder as well. In FIG. 22, (a) includes: (i) PCL3k network; (ii) PCL3k/PEG2k-GRGDS (85/15) co-network; (iii) PCL3k/PEG2k-GRGDS (70/30) co-network; (iv) PCL3k/PEG2k-GRGDS (60/40) co-network; and (v) PEG2k-GRGDS powder, while (b) includes: (i) PCL3k network; (ii) PCL3k/MPEG2k (85/15) co-network; (iii) PCL3k/MPEG2k (70/30) co-network; (iv) PCL3k/MPEG2k (60/40) co-network; and (v) MPEG2k powder, respectively.

As shown in FIG. 22, the second heating trace for each co-network exhibited only one melting transition ($T_m$). For the PCL3k/PEG2k-GRGDS co-networks with less than 40 wt. % of PEG2k-GRGDS, the $T_m$, approximately 44.0° C., was not significantly influenced by the composition, while $T_m$ of PCL3k/PEG2k-GRGDS (60/40) co-network was slightly shifted to 39.0° C. WAXD proved the $T_m$ should be assigned to the melting of PCL crystallites by only showing the PCL characteristic peaks at 2θ=15.6°, 22.7°, 23.4°, and 25.6° (data not shown). The heats of fusion ($\Delta H_m$) of the PCL3k/PEG2k-GRGDS co-networks, as expected, decreased with decreasing PCL weight fraction. The corresponding $T_m$ and $\Delta H_m$ are summarized in Table 1.

TABLE 1

DSC Data of PCL3k/PEG2k-GRGDS Co-Networks.

| PCL3k/PEG2k-GRGDS co-network (w/w) | $T_m$ (° C.) | $\Delta H_m$ (J/g) | $T_c$ (° C.) | $\Delta H_c$ (J/g) |
|---|---|---|---|---|
| 100/0 | 43.9 | 55.5 | 20.3 | 53.4 |
| 85/15 | 44.6 | 52.4 | 16.4 | 48.7 |
| 70/30 | 44.3 | 49.2 | 15.2 | 46.3 |
| 60/40 | 39.0 | 44.9 | 9.2 | 39.9 |
| 0/100 | 44.6 | 90.8 | 3.7 | 84.7 |

In contrast, the DSC traces of each of the PCL3k/MPEG2k co-network (control) showed two independent $T_m$ (FIG. 22), which indicated that the PCL3k/MPEG2k co-networks possessed segregated crystalline PEG and PCL phases. It was assumed that the lower $T_m$ was related to the melting of PEG crystallites, whereas the higher $T_m$ was assigned to crystalline PCL phase. This is because the higher $T_m$ was only slightly influenced by the composition, in the range of 43.9° C. to 41.8° C. for all the PCL3k/MPEG2k co-networks, while the lower $T_m$ increased with increasing MPEG2k content being shifted from 21.7° C. to 27.4° C. and 32.1° C. for the co-networks containing 15, 30 and 40 wt. % of MPEG2k, as shown in FIG. 22 and Table 2. $\Delta H_m$ of both PCL and MPEG phases increased with their increasing content in the PCL3k/MPEG2k co-networks, as shown in Table 2.

TABLE 2

DSC Data of PCL3k/MPEG2k Co-Networks.

| PCL3k/MPEG2k co-network (w/w) | $T_m$ (° C.) | | $\Delta H_m$ (J/g) | | $T_c$ (° C.) | | $\Delta H_c$ (J/g) | |
|---|---|---|---|---|---|---|---|---|
| | MPEG | PCL | MPEG | PCL | MPEG | PCL | MPEG | PCL |
| 100/0 | — | 43.9 | — | 55.5 | — | 20.3 | — | 53.4 |
| 85/15 | 21.7 | 44.2 | 6.7 | 42.0 | — | 16.7 | — | 50.1 |
| 70/30 | 27.4 | 42.6 | 21.2 | 32.4 | −23.4 | 14.7 | 10.6 | 44.0 |
| 60/40 | 32.1 | 41.8 | 24.8 | 29.0 | −5.1 | 15.4 | 17.4 | 36.9 |
| 0/100 | 52.6 | — | 175.3 | — | 34.0 | — | 170.3 | — |

To further demonstrate the crystalline states of both PCL and PEG phase in PCL3k/PEG2k-GRGDS and PCL3k/MPEG2k co-network, PCL3k/PEG2k-GRGDS (60/40) and PCL3k/MPEG2k (60/40) co-network having the highest PEG content (40 wt. %) in both groups were characterized by WAXD under a low temperature circumstance (0° C. to 5° C.). As shown in FIG. 23, PCL3k/PEG2k-GRGDS (60/40) co-network showed only PCL characteristic peaks (2θ=15.6°, 22.7°, 23.4°, and 25.6°, while PCL3k/MPEG2k (60/40) co-network showed an obvious PEG diffraction peak at 2θ=20.2° in addition to all the PCL characteristic peaks. FIG. 23 depicts the WAXD patterns of both (a) PCL3k/PEG2k-GRGDS (60/40) co-network and (b) PCL3k/

MPEG2k (60/40) co-network at low temperature (0–5° C.). For comparison, PCL3k network, PEG2k-GRGDS powder and commercial MPEG2k powder are shown as well.

The results suggested that PEG2k-GRGDS dangling chains in PCL3k/PEG2k-GRGDS co-network were amorphous, while the MPEG2k phase in PCL3k/MPEG2k co-network was crystalline because of the high chain mobility and regularity of pendant MPEG2k chain ends. Two-dimensional WAXD patterns of both samples, shown in FIG. 24, proved this result as well by showing that the former exhibited only two strong reflections of (110) and (200) that index as PCL crystalline rings at 2θ=22.7 and 23.4°, respectively, while the latter clearly displayed not only PCL (110) and (200) reflections but also (120) reflection ring that index as PEG crystalline rings at 2θ=20.1°. Therefore, the possible micro-structures of PCL3k/PEG2k-GRGDS and PCL3k/MPEG2k co-network could be illustrated in FIGS. 24c and 24d. Hydrogen bonds could exist among GRGDS molecules, PEG chains and PCL network. The connection of the hydrogen bonds results in the low mobility and regularity of pendant PEG2k-GRGDS chains, thus the PEG phase in PCL3k/PEG2k-GRGDS co-network stays amorphous. In contrast, there were no hydrogen bonds in PCL3k/MPEG2k co-network, so the side MPEG2k phase could form a crystalline aggregation due to the high chain mobility and regularity of pendant MPEG2k chains. Fourier Transformed Infra-Red ("FTIR") spectra of PCL3k/PEG2k-GRGDS (60/40) co-network showed a strong and broad absorption peak in the range of 3170-3540 cm$^{-1}$, which verified the presence of hydrogen bonds in the sample (data not shown), while the same peak was absent from that of PCL3k/MPEG2k (60/40) co-network.

Wet DSC traces of each of the PCL3k/PEG2k-GRGDS and PCL3k/MPEG2k hydro gels exhibited only one $T_m$ in the range of 36.0° C. to 43.3° C., except a water exothermal peak at about 0° C., as shown in FIG. 25. The figure includes first cooling (exotherms, upper) and second heating (endotherms, lower) DSC traces of: (a) PCL3k/PEG2k-GRGDS hydro gels; (b) PCL3k/MPEG2k hydro gels; and (c) PCL2k/PEG2k-GRGDS (85/15) co-network (dry sample, black line) and its hydrogel (wet sample, red line). Both the heating and cooling rate were 10° C./min from −80° C. to 70° C. PCL3k network which was immersed in water experiencing the same procedure as the swelling study of those hydro gels is shown as well. (a) includes: (i) PCL3k network, (ii) PCL3k/PEG2k-GRGDS (85/15) hydrogel, (iii) PCL3k/PEG2k-GRGDS (70/30) hydrogel, and (iv) PCL3k/PEG2k-GRGDS (60/40) hydrogel; correspondingly, while (b) consists of (i) PCL3k network, (ii) PCL3k/MPEG2k (85/15) hydrogel, (iii) PCL3k/MPEG2k (70/30) hydrogel, and (iv) PCL3k/MPEG2k (60/40) hydrogel. It should be noted that in (c), during the second heating, both dry and wet samples were first heated to 25° C., isothermal for 120 min, then cooled down to −20° C., isothermal for 3 min, and finally heated back to 70° C.

Compared with the DSC data of the corresponding dry samples, both $T_m$ and $\Delta H_m$ of PCL3k/PEG2k-GRGDS hydrogel and PCL3k/MPEG2k hydrogel decreased due to the plasticizing effect of the water molecules within the hydro gels (Tables 3). Here, it was concluded that PCL phase crystallized in the PCL3k/PEG2k-GRGDS co-network both in dry and wet (swollen by water) state, which indicated that PCL fraction in the co-network could provide desired mechanical and shape-memory properties.

TABLE 3

DSC Data of Swollen PCL3k/PEG2k-GRGDS and PCL3k/MPEG2k Hydrogels.

| Sample Name | $T_m$ (° C.) | $\Delta H_m$ (J/g) | $T_c$ (° C.) | $\Delta H_c$ (J/g) |
|---|---|---|---|---|
| PCL3k network (100/0) | 43.3 | 51.3 | 12.3 | 50.5 |
| PCL3k/PEG2k-GRGDS (85/15) | 43.2 | 42.6 | 13.8 | 42.1 |
| PCL3k/PEG2k-GRGDS (70/30) | 40.5 | 32.5 | 6.6 | 33.6 |
| PCL3k/PEG2k-GRGDS (60/40) | 39.2 | 27.7 | 7.8 | 30.5 |
| PCL3k/MPEG2k (85/15) | 42.8 | 41.9 | 10.0 | 43.4 |
| PCL3k/MPEG2k (70/30) | 37.2 | 29.7 | −0.0 | 30.7 |
| PCL3k/MPEG2k (60/40) | 36.0 | 23.7 | −1.0 | 23.4 |

As a potential bioactive implanted material for tissue engineering, the transition temperature of the shape-memory polymer, ideally, should be either between room and body temperature for automatically inducing the shape change upon implantation without additional heating, while offering the ability to maintain its temporary shape without unwanted shape recovery at room temperature. In the current study, the transition temperature, $T_m$, of each of PCL3k/PEG2k-GRGDS hydrogel, as shown 21 and Table 3, was around 40° C., which is slightly above body temperature and enables on demand control of the shape change by short time application of directly or indirectly supplemental heating. One short-term goal is to investigate the cellular behavior in response to the mechanical cues resulting from the recovery of the substrates during cell culture. Therefore, the ongoing effort is to decrease $T_m$ of PCL3k/PEG2k-GRGDS hydro gels to a value slightly below body temperature, which would be both crucial for achieving this goal and useful for the design of clinical devices. Decreasing $T_m$ of the PCL3k/PEG2k-GRGDS hydro gels could be achieved by decreasing the average molecular weight of PCL3k diacrylates used as precursors in the polymer network synthesis to PCL2k diacrylates. For example, PCL2k/PEG2k-GRGDS (85/15) co-network was prepared by photocuring the mixture of PCL2k diacrylates and acrylate-PEG2k-GRGDS in the presence of DMPA (2 wt. %, with respective to the total weight of the both precursors) and tetrathoil (1:1 molar ratio of thiol to double bonds), in which the weight ratio of PCL2k diacrylates to acrylate-PEG2k-GRGDS was 85 to 15. It was encouraging that PCL2k/PEG2k-GRGDS (85/15) co-network exhibited a very sharp thermal transition, $T_m$, at 32.9° C. (FIG. 25, black line), which was much lower than that of PCL3k/PEG2k-GRGDS (85/15) (44.6° C., shown in FIG. 22a and Table 1). The $T_m$ of PCL2k/PEG2k-GRGDS (85/15) hydrogel was 31.8° C. (FIG. 25, panel (c), red line), with the beginning and ending temperature at about 28.3° C. and 36.2° C., respectively, indicating the automatic shape recovery from its deformed state will occur when heated to body temperature, while the temporary shape can be maintained at room temperature.

EXAMPLE 13

Mechanical Properties of the PCL3k/PEG2k-GRGDS Co-Networks

Each of the PCL3k/PEG2k-GRGDS co-networks and pure PCL3k network exhibited similar tensile storage modulus ("E") versus temperature traces, as shown in FIGS. 26A, 26B, and 26C, in which the figures show the storage modulus vs. temperature for: PCL3k/PEG2k-GRGDS co-networks (FIG. 26A), the PCL3k/MPEG2k co-networks as a function of the weight percent of PEG2k-GRGDS and MPEG2k components (FIG. 26B), and the storage modulus at 25° C. for the PCL3k/PEG2k-GRGDS co-networks (open circle) and PCL3k/MPEG2k co-networks (solid circle) as a function of the weight percent of PEG2k-GRGDS and MPEG2k components, respectively (the black squares show the storage modulus of PCL2k/PEG2k-GRGDS (85/15) co-network at 25° C.). FIG. 26A also includes the storage modulus of PCL2k/PEG2k-GRGDS (85/15) co-network, as shown in the dash line. The data were presented as mean±standard deviation for n=3.

The storage modulus of all the samples gradually reduced by traversing a glass transition ($T_g$) starting around −50° C. and then sharply dropped around the melting temperature between 43° C. and 57° C. The behavior was typical for most semicrystalline networks. The $T_g$ was associated with the amorphous PCL polyester chains, even though it was not clearly revealed in the DSC curves of both PCL3k/PEG2k-GRGDS co-networks and PCL3k network (see FIG. 22). Below $T_g$, the sample was glassy with the storage modulus well above 1 GPa. When reaching $T_g$, the storage modulus began to drop and was gradually decayed to a value below 200 MPa as traversing the glass transition. Upon further heating, the storage modulus kept decaying, dropped dramatically at about 43° C. at the onset of $T_m$ of PCL component, and finally gave rise to a rubbery plateau at ~1 MPa after the temperature was above 60° C. It could be seen that the E values at the incipient melting transition temperature were approximately two orders of magnitude larger than that those at the incipient temperature of the rubbery plateau, implying that the stiffness can be dramatically changed in a narrow range of temperatures. For the PCL3k/MPEG2k co-networks (FIG. 26B), the initial drop in modulus around −50° C. was much the same as that of the corresponding PCL3k/PEG2k-GRGDS co-networks, however the second drop of the modulus of PCL3k/MPEG2k (70/30) and PCL3k/MPEG2k (60/40) co-network took place at about 22° C. and 28° C., respectively, due to the melting of crystalline PEG phase. This agrees with the corresponding DSC data of $T_m$ of PEG fraction in the both co-networks showed in Table 2 and FIG. 22B. Following the second drop, a dramatic drop, associated with the melting of crystalline PCL component at about 43° C., was observed in for both compositions.

Figure 6:
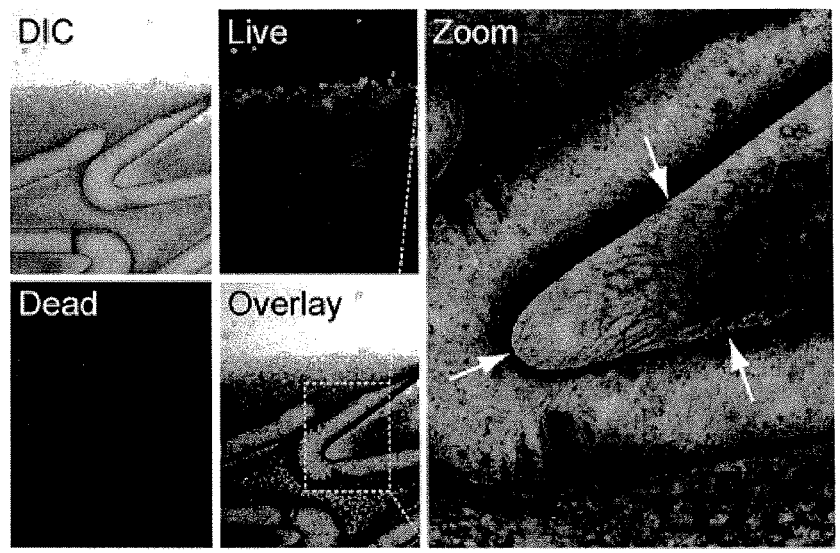
FIG. 6 is an image of cells and ECM between a scaffold strut.

Polymeric devices should have desired mechanical strengths to withstand manipulation during surgical implantation at room temperature. Therefore, the storage modulus of each of PCL3k/PEG2k-GRGDS co-networks at 25° C. is shown in FIG. 26C, compared with that of both PCL3k/MPEG2k co-networks and pure PCL3k network. It was seen that the modulus of PCL3k/PEG2k-GRGDS co-networks decreased with increasing the weight percent of PEG2k-GRGDS component in the co-networks (130.0±18.1, 118.7±15.1, 70.8±5.7 and 36.4±2.6 MPa for the co-networks containing 0, 15, 30, and 40 wt. % PEG2k-GRGDS, respectively). Interestingly, for the PCL3k/MPEG2k co-networks, E at 25° C. depended on the composition of the co-networks, showing an order was PCL3k/MPEG2k (85/15) network (108.1±21.8 MPa)>PCL3k/MPEG2k (60/40) network (93.2±5.6 MPa)>PCL3k/MPEG2k (70/30) network (72.4±2.9 MPa). That is to say, PCL3k/MPEG2k (60/40) co-network, although having the lower gel fraction (67.1±2.5%) compared with that of PCL3k/MPEG2k (70/30) co-network (89.4±2.3%) showed the higher E value than that of PCL3k/MPEG2k (70/30) co-network. Furthermore, the modulus of PCL3k/MPEG2k (60/40) co-network (93.2±5.6 MPa) was much higher than that of both PCL3k/PEG2k-GRGDS (70/30) (70.8±5.7 MPa) and PCL3k/PEG2k-GRGDS (60/40) co-network (36.4±2.6 MPa). The surprisingly high modulus of PCL3k/MPEG2k (60/40) co-network was attributed to both crystalline PCL phase and crystalline MPEG phase forming two sets of physical crosslinks in addition to covalent thio-ether crosslinks. PCL2k/PEG2k-GRGDS (85/15) co-network showed a similar tensile storage modulus versus temperature trace as compared with all PCL3k/PEG2k-GRGDS co-networks and pure PCL3k network (FIG. 6). Its storage modulus at 25° C. was 50.3±2.8 MPa that was comparable with those of PCL3k/PEG2k-GRGDS co-networks (118.7±15.1 MPa for PCL3k/PEG2k-GRGDS (85/15) co-network, 70.8±5.7 MPa for PCL3k/PEG2k-GRGDS (70/30) co-network, and 36.4±2.6 MPa for PCL3k/PEG2k-GRGDS (60/40) co-network).

The E values at rubbery plateau region which is associated with cross linking density decreased with increasing the weight percent of PEG2k-GRGDS and MPEG2k components in both PCL3k/PEG2k-GRGDS and PCL3k/MPEG2k co-networks, as shown in FIG. 29. The results were partially in accordance with those of gel fraction that showed similar trend with the increasing the content of PEG2k-GRGDS and MPEG2k side chains in both co-networks (FIG. 21).

EXAMPLE 14

Shape Memory Behavior

In order to explore the shape memory effects of the PCL3k/PEG2k-GRGDS co-networks, DMA was employed with controlled force mode and ramping temperature system and was performed in the following manner. The sample was equilibrated at 70° C. (>$T_m$) prior to the application of force, then elongated by ramping to a programmed stress (0.5 MPa) at a constant ramping force (0.05 N/min), which leads to an orientation of the amorphous, flexible PCL chain segments. Subsequently, the elongated sample was fixed by cooling at a rate of 2° C./min to 0° C. at constant stress, which was supported by the crystallizable PCL phase. The sample was then unloaded and reheated back to 70° C., so that the elongated sample (a temporary shape) recovered to its original shape which is in a stress-free, equilibrium state. FIGS. 27A and 27B show the repeated 1W-SM cycles of PCL3k/PEG2k-GRGDS (85/15) co-network, PCL3k/PEG2k-GRGDS (70/30) co-network, and PCL2k/PEG2k-GRGDS (85/15) co-network under 500 kPa, compared with those of pure PCL3k network. The remarkably reproducible shape memory behavior of each sample was observed from the repeated three cycles obtained under the same condition. All samples also showed similar 1W-SM behaviors with an increase of strain while cooling/fixing, as indicated by the bold arrow in FIGS. 27A and 27B, resulted from the crystallization of PCL under stress. Both shape fixing and recovery were close to 99% for the three GRGDS-containing co-networks and 100% for pure PCL3k network.

The strain increments on cooling of 1W-SM cycles indicated that PCL/PEG-GRGDS co-networks have the potential of 2W-SM behavior which involves pre-deformed samples reversibly elongating and contracting on cooling and heating through their transition temperature, respectively. The 2W-SM behavior of PCL3k/PEG2k-GRGDS (85/15) co-network, PCL3k/PEG2k-GRGDS (70/30) co-network, and PCL2k/PEG2k-GRGDS (85/15) co-network are shown in FIG. 28A, compared with that of pure PCL3k network. Clearly, a reversible temperature-responsive strain change occurred when a constant stress was applied to maintain equilibrium between semicrystalline and amorphous phase of each sample. During the cooling step, a slight increase of strain was observed with the decreasing temperature, however, at the point of crystallization temperature, the strain increased dramatically. The maximum strain increment in the cooling step was 67.5% for PCL3k network, 79.7% for PCL3k/PEG2k-GRGDS (85/15) co-network, 132.4% for PCL3k/PEG2k-GRGDS (70/30) co-network, and 40.2% for PCL2k/PEG2k-GRGDS (85/15) co-network, provided that the length of the pre-deformed sample at high temperature was the initial length ($R_{act}(\sigma)=0\%$). The elongation event upon cooling was completely reversed through a heating-induced contraction upon heating back to the original temperature where the $R_{act}(\alpha)$ value was close to zero. The recovery ratio was 94.2%, 93.0%, 91.1%, and 95.1%, respectively, for the four samples examined.

Two-way shape memory behavior of PCL3k/PEG2k-GRGDS (85/15) co-network during isothermal process under different temperatures (41, 39, 37, 35, and 33° C.), as an example, is presented in FIG. 28B. The sample was elongated at 70° C. at a constant stress (500 kPa) and was subsequently cooled to each temperature for isothermal crystallization for 90 min, followed by being heated back to high temperature (70° C.) for complete melting. It was found that the strain increased with time for all temperatures. At the isothermal temperatures of 41, 39, and 37° C., the strain increments are limited due to the slow crystallization rate. At 35° C., the strain slowly increased during the isothermal process. The strain increment became much faster with decreasing the isothermal temperature to 33° C. due to increasing the crystallization rate.

Since PCL3k/PEG2k-GRGDS (60/40) co-network showed the lower $T_c$ peak at 9.2° C. with the ending temperature at about −10.0° C. (below 0° C.) when it was compared with the other two GRGDS-containing co-networks and PCL network, both its 1W-SM and 2W-SM cycles were programmed to ramp in the range of 70° C. to −20° C. Interestingly, PCL3k/PEG2k-GRGDS (60/40) co-network exhibited both excellent 1W-SM and 2W-SM property, as illustrated in FIGS. 30A and 30B, although it had the lowest gel fraction (65.3±1.8%, shown in FIG. 21). The shape fixing and recovery obtained from its 1W-SM cycle (FIG. 30A) was 98.5% and 98.3%, respectively, whereas its maximum strain increment was approximately 38.4% in the light of 2W-SM cycle (FIG. 30B). Therefore, it was clear that PCL/PEG-GRGDS co-networks produced from thiol-ene chemistry had not only excellent, reproducible 1W-SM effect which is an actuation between a temporary shape and a permanent shape, but also 2W-SM effect which allows changing reversibly between two permanent shapes through cooling/heating cycles under an applied single force. The latter has the potential to mimic reversible actuation of artificial muscles or actuators. Moreover, it could be used to apply elongational strain to adherent cells while held isothermally under tension, in vitro or in vivo.

EXAMPLE 15

Cell Attachment

FIGS. 31A, 31B, and 31C illustrate the attachment of fibroblasts to PCL3k network, PCL3k/MPEG2k (85/15) hydrogel, PCL3k/PEG2k-GRGDS (85/15) hydrogel, PCL2k/PEG2k-GRGD (85/15) hydrogel, and tissue culture polystyrene (TCPS) at 3 h, 6 h and 12 h after seeding, respectively. The normalized fibroblast attachments on the five substrates were increased with the culture time from 3 h to 12 h. For example, correspondingly, they were increased from 20.9±8.3%, 15.9±4.4%, 25.1±5.9%, 33.3±8.0%, and 55.9±8.4% at 3 h to 31.7±4.2%, 23.9±5.9%, 43.4±14.5%, 44.7±5. %, and 93.5±18.1% at 12 h for PCL3k network, PCL3k/MPEG2k (85/15) hydrogel, PCL3k/PEG2k-GRGDS (85/15) hydrogel, PCL2k/PEG2k-GRGD (85/15) hydrogel, and TCPS, respectively. As expected, both GRGDS-containing hydro gels showed higher fibroblast attachment at each time point than PCL3k/MPEG2k (85/15) hydrogel and pure PCL3k network. At 6 h, for example, 37.0±7.4% and 40.9±5.0% of cells attached on PCL3k/PEG2k-GRGDS (85/15) hydrogel and PCL2k/PEG2k-GRGDS (85/15) hydrogel, respectively, and only 20.4±10.1% and 26.9±6.9% for PCL3k/MPEG2k (85/15) hydrogel and pure PCL3k network, correspondingly. The result indicated that the incorporation of GRGDS molecules into the hydro gels stimulated the fibroblasts adhesion by presenting biospecific bindings with the cells.

Fibroblasts attachment on PCL2k/PEG2k-GRGDS (85/15) hydrogel showed no significant difference than that on PCL3k/PEG2k-GRGDS (85/15) hydrogel at each time point (P>0.05). For example, the normalized cell attachment on PCL2k/PEG2k-GRGDS (85/15) hydrogel and PCL3k/PEG2k-GRGDS (85/15) hydrogel was 33.3±8.0% and 25.1±5.9% at 3 h, 40.9±5.0% and 37.0±7.4% at 6 h, and 44.7±5.0% and 43.4±14.5% at 12 h, respectively. PCL3k/MPEG2k (85/15) hydrogel showed the lowest cell attachment at each time point. This is because the high mobility of the dangling MPEG2k chains sterically hinder proteins (like serum proteins in the medium) from adhesion and, thus, cell attachment to the material. The normalized fibroblast attachments on all the substrates used in this study, including PCL3k network, PCL3k/MPEG2k (85/15) hydrogel, PCL3k/MPEG2k (70/30) hydrogel, PCL3k/PEG2k-GRGDS (85/15) hydrogel, PCL3k/PEG2k-GRGDS (70/30) hydrogel, PCL2k/PEG2k-GRGDS (85/15) hydrogel, and TCPS, are shown in FIGS. 32A, 32B, and 32C. It was found that the GRGDS-functionalized hydro gels promoted cell adhesion and spreading than those corresponding hydro gels without GRGDS peptide and pure PCL3k network. A morphological observation of fibroblasts culturing on the different substrates for 12 h supporting the quantified cell attachment data was shown in FIGS. 32A-C and 33. Distinct differences in cell attachment and spreading were observed between the hydro gels modified with the GRGDS sequence and those without the GRGDS sequence. Fibroblasts seeded on the GRGDS-functionalized hydro gels showed higher cell attachment after 12 h, whereas cell adhesion was significantly limited for the hydro gels lacking the GRGDS moiety and the pure PCL3k network. Furthermore, in the case of the cells seeded on GRGDS-functionalized hydro gels, they showed extensive spreading and were in good contact with those of surrounding cells forming a contiguous cell sheet, suggesting that the adhesion peptide enhanced the cell attachment and spreading. It was apparent that not only few cells were observed, but also the cells exhibited a spherical morphology with very few extension on both PCL3k/MPEG2k (85/15) hydrogel and PCL3k/MPEG2k (70/30) hydrogel due to the remarkable non-adhesive property of PEG spacer arms at the hydro gels surface. In contrast, for the hydro gels incorporating GRGDS via PEG spacer, it was the chain flexibility and mobility of PEG that contribute to cell recognition, in that the spacer arm could facilitate the cells specific interaction with the incorporated peptide medicated by specific receptors on the cell surface.

The morphologies of fibroblasts seeded on the hydro gels with and without GRGDS at 24, 48, and 72 h are shown in FIGS. 34A-G. Those of fibroblasts seeded on PCL3k network and TCPS were examined for comparison. As expected, the cells seeded on TCPS showed the highest cell attachment and most extensive spreading at each time point. The cell density significantly increased with the culture time. Compared with the hydro gels without GRGDS and PCL3k network, GRGDS-functionalized hydro gels showed higher cell attachment after 24 h. Also, cell growth was greatly augmented by the recognition between the cells and the binding sites of the GRGDS ligands on the hydro gels, and proliferated as a result. On the contrary, the cells seeded on the hydro gels without GRGDS and the PCL3k network had a decreased density with the culture time from 24 h to 72 h. Furthermore, the cells on these materials that survived through 72 h became smaller and a more rounded shape than those at 24 h and 48 h. Almost no cells survived over 72 h on PCL3k/MPEG2k (70/30) hydrogel. These results suggested that fibroblasts have only weak, nonspecific interactions with these materials, and further exemplified the importance of GRGDS peptide for cells adhesion, spreading and growth on the material.

EXAMPLE 16

Cellular Behavior in Response to the Shape Memory Effect

In biomedical shape memory polymer devices designed for deployment at body temperature, the recovery behavior is inherently isothermal. FIG. 35 presents the isothermal shape recovery process of the stretched PCL2k/PEG2k-GRGDS (85/15) co-network film at 37.0° C. Here, the film was elongated up to 50% strain by increasing the applied load at a rate of 0.05 N/min at 50° C. ($>T_m$), and cooled down to $-10°$ C. ($<T_m$) at a constant cooling rate (3° C./min) to fix the temporary shape. During the cooling step, the strain increased up to 103.5% due to the crystallization-induced elongation. Then, the sample was unloaded and annealed at 37° C. for 10 h to trigger the shape recovery of the elongated sample. After this isothermal hold, the sample was finally heated to high temperature (60° C.) at 3° C./min to achieve full recovery. It was found that recovery of the stretched sample was triggered at 37.0° C. to a value close to 75.1%, while the recovery ratio during the whole heating process from $-10°$ C. to 60° C. was 98.4%. It should be noted that no significant shape recovery occurred at both 25° C. and 28° C., revealing that the temporary shape of the elongated sample could be kept when seeded with cells or during surgery as a biomedical device at room temperature. The shape recovery of the swollen PCL2k/PEG2k-GRGDS (85/15) hydrogel at 37° C. measured based on the length changes before and after shape recovery was 83.7±2.7% (n=3), which was possibly due to its lower $T_m$ (31.8° C.) than that of the corresponding dry sample (PCL2k/PEG2k-GRGDS (85/15) co-network, $T_m$=32.9° C.). In addition, the hydrogel film did not display significant shape recovery in the isothermal processes of both 25° C. and 28° C.

Dynamic cell behavior on the stretched PCL2k/PEG2k-GRGDS (85/15) hydrogel film was analyzed to understand how cells reacted to the mechanical cues resulting from the shape recovery of the active substrate at body temperature. Interestingly, it was observed that fibroblasts aligned in the direction nearly perpendicular to the reference line, as indicated by the white arrows in certain panels of FIG. 36A, which designated the sample stretched direction. The distribution of the orientation angles (FIG. 36A, panel (b)) was not uniform and the perpendicular direction was favored compared to all other orientations, whereas fibroblasts displayed random orientation on the un-stretched PCL2k/PEG2k-GRGDS (85/15) hydrogel film (control) (FIG. 36A, panels (c) and (d)). These results suggested that the cells could sense the physical changes of the active substrate during cell culture and adopt the elongated morphologies in response to the strain recovery of the stretched sample.

For the experiments depicted in FIG. 36, the bulk film was stretched up to 50% strain at 50° C. ($T>T_m$) and then cooled to $-10°$ C. to fix the strain. During the cooling step, the strain was increased up to 103% due to the crystallization-induced elongation. Cells were seeded on the stretched sample at room temperature, cultured at 28° C. for 5 h, and then further cultured at 37° C. for another 5 h before being observed using live/dead assay and CellMask membrane staining. The reference line was drawn on each sample using a razor blade to indicate the direction of the sample stretch. The cells aligned proximately in the direction perpendicular to the reference line. Panels (c) and (d) of FIG. 36A show the morphology and the orientation angle distribution of fibroblasts cultured on the un-stretched PCL2k/PEG2k-GRGDS (85/15) hydrogel film, respectively. The cell culture procedure is the same as described above, and the cells displayed random orientation. Panels (e) and (f) of FIG. 36A show the morphology and the orientation angle distribution of fibroblasts cultured on the stretched (a) sample only at 28° C. for 5 h (control experiment) before observation, respectively. The cells preferred to align parallel to the reference line. Panels (g) and (h) if FIG. 36B show the morphology and the orientation angle distribution of fibroblasts cultured on the stretched PCL3k/PEG2k-GRGDS (85/15) hydrogel film ($T_m$=43.2° C.), respectively. The film is stretched up to 50% strain at 70° C. ($T>T_m$) and then cooled to 0° C. to fix the strain. During the cooling step, the strain increases up to 98.1% due to the crystallization-induced elongation. The cell culture procedure is the same as mentioned above. The cells proximately aligned parallel to the reference line (the stretching direction).

To further illustrate the influence of tuning appropriate $T_{trans}$ of the active substrate between room and body temperature on cells behavior, two other control experiments were carried out. When fibroblasts cultured on the same sample as used in FIG. 36A, panel (a) (the stretched PCL2k/PEG2k-GRGDS (85/15) hydrogel film) only at 28° C. for 5 h, the cells preferred to align parallel to the reference line (the stretching direction) (FIG. 36A, panels (e) and (f)). In addition, it was also found that fibroblasts approximately aligned parallel to the sample stretching direction, when they were cultured on the stretched PCL3k/PEG2k-GRGDS (85/15) hydrogel film that having a relatively high $T_m$ at about 43.2° C. (FIG. 36B, panels (g) and (h)). It should be noted that the stretched PCL3k/PEG2k-GRGDS (85/15) hydrogel film was prepared in the same way as preparing the stretched PCL2k/PEG2k-GRGDS (85/15) hydrogel film mentioned above. Specifically, a PCL3k/PEG2k-GRGDS (85/15) hydrogel film was stretched up to 50% strain at 70° C. ($T>T_m$) and then cooled down to 0° C. to fix the strain. During the cooling step, the strain increased up to 98.1% due to the crystallization-induced elongation.

For the both control experiments mentioned above, the strain is static, since no shape recovery occurred during cell culture, thus cells align parallel to the direction of applied strain. Whereas for the experimental group, about 75.1% of shape recovery could achieve at 37° C. in only 15 min (FIG. 35, which is a graph of isothermal shape recovery process of the stretched PCL2k/PEG2k-GRGDS (85/15) co-network film at 37° C., where the sample was heated to 50° C. and then stretched, followed by cooling to $-10°$ C. under loading to fix the strain (temporary shape), and then the sample was heated to 37° C. to induce the recovery of its temporary shape and annealed at 37° C. for 10 h, before heated to 60° C. to trigger full recovery to its original shape), thus, in response to the active strain, cells prefer to reorient to an angle way from the direction of applied stretch and align nearly perpendicular to the strain direction. These results indicated that tuning the transition temperature of PCL2k/PEG2k-GRGDS (85/15) hydrogel between room and body temperature offered a potential to dynamically control cell orientation and cell-material interactions during cell culture in vitro.

The cell culture substrates and scaffolds of the present invention are preferably adhered, bonded, or supplied in connection with a supporting material using known techniques. For example, the scaffolds of the present invention may be provided in combination with a culture dish, a petri dish, a culture flask, a permeable support, a microplate, a membrane, a multiwell tissue culture plate, and other conventional cell culture supporting materials.

The cell culture substrates and scaffolds of the present invention are useful because they have the unprecedented ability to change architecture, thereby providing control of many physical aspects of tissue engineering through design of the scaffold material itself. Once such scaffolds are used for culturing cells, these materials will offer an entirely new mechanism for mimicking natural processes, for facilitating construct preparation in the lab or in the operating room, and for non-invasive delivery of scaffolds that deploy once in situ. Thus, important advances in regenerative medicine could be expected.

In addition, the biomimetic, architecture-changing scaffolds will provide in vitro models of tissue development and repair for quantitative studies of cell-matrix interactions, cell mechanics, matrix mechanics, and mechanobiology. It is also expected that what is learned will contribute to improved understanding of the materials science of SMPs, in turn leading to further innovations in scaffold design. Furthermore, the invention may have catalytic impact on other fields in which SMPs are being applied, which include medical applications such as dialysis, tumor therapy, self-deploying neuronal electrodes, thrombus, and coronary stents.

For example, the present invention may be used to improve the treatment of musculoskeletal disorders through the development and clinical translation of advanced tissue-engineering scaffolds that undergo programmed changes in architecture as a means of mimicking natural processes, of facilitating construct preparation in the lab or in the operating room, and of allowing non-invasive delivery of scaffolds that deploy once in situ. The scaffolds of the present invention may be used to mimic normal tissue formation or repair during heart, cartilage, bone, and tendon engineering.

Although the present invention has been described in connection with a preferred embodiment, it should be understood that modifications, alterations, and additions can be made to the invention without departing from the scope of the invention as defined by the claims.

What is claimed is:

1. A method of culturing cells comprising the steps of:
providing a cell culture substrate comprising a thermoplastic shape memory polymer having a poly(ε-caprolactone) macromer cross-linked with a poly(ethylene glycol) peptide monomer;
seeding said cell culture substrate with a cell;
promoting the growth of said cell; and
applying a stimulus to transition said cell culture substrate from a first configuration to a second configuration.

2. The method of claim 1, wherein said substrate further comprises a supporting material to which said shape memory polymer is adhered.

3. The method of claim 2, wherein said supporting material is from a support selected from the group consisting of a culture dish, a petri dish, a culture flask, a permeable support, a microplate, a membrane, a medical device, and a multiwell tissue culture plate.

4. The method of claim 1, wherein said cell culture substrate applies stress to said cell when said substrate is in said second configuration.

5. The method of claim 1, wherein the peptide in the poly (ethylene glycol) peptide monomer is Gly-Arg-Gly-Asp-Ser (SEQ ID NO: 1).

6. The method of claim 1, wherein the thermoplastic shape memory polymer has the formula PCL3k/PEG2k-GRGDS (85/15).

7. The method of claim 1, wherein the thermoplastic shape memory polymer has the formula PCL3k/PEG2k-GRGDS (70/30).

8. The method of claim 1, wherein the thermoplastic shape memory polymer has the formula PCL2k/PEG2k-GRGDS (85/15).

9. The method of claim 1, wherein said first configuration comprises a grooved topography and said second configuration comprises a smooth topography.

10. The method of claim 9, wherein said cells are elongated and aligned in a parallel configuration in combination with said grooved topography and said cells are randomly oriented in combination with said smooth topography.

11. The method of claim 9, wherein said cells have microfilaments aligned with said grooved topography in said first configuration and said cells have randomly distributed microfilaments in said second configuration.

12. The method of claim 1, wherein said cell culture substrate has a first surface area in contact with said cells when said cell culture substrate is in said first configuration and a second surface area in contact with said cells that is different than said first surface area when said cell culture substrate is in said second configuration.

13. The method of claim 12, wherein said first surface area is greater than said second surface area.

* * * * *